US010130371B2

(12) United States Patent
Dehdashtian et al.

(10) Patent No.: US 10,130,371 B2
(45) Date of Patent: Nov. 20, 2018

(54) AORTIC OCCLUSION DEVICE

(71) Applicant: Edwards Lifesciences Corporation, Irvine, CA (US)

(72) Inventors: Mark Dehdashtian, Irvine, CA (US); Teodoro S. Jimenez, Irvine, CA (US); Nathan Satter, San Diego, CA (US); Fabian D. Schroeder, San Diego, CA (US); Raffaele Mazzei, Carlsbad, CA (US); Jeff Kosmoski, San Diego, CA (US); Shaun Zamani, Irvine, CA (US); Adam Yestrepsky, Irvine, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 878 days.

(21) Appl. No.: 14/276,795

(22) Filed: May 13, 2014

(65) Prior Publication Data
US 2014/0350523 A1 Nov. 27, 2014

Related U.S. Application Data

(60) Provisional application No. 61/822,796, filed on May 13, 2013.

(51) Int. Cl.
A61B 17/12 (2006.01)
A61M 1/34 (2006.01)
(Continued)

(52) U.S. Cl.
CPC .... A61B 17/12109 (2013.01); A61B 17/1204 (2013.01); A61B 17/1215 (2013.01);
(Continued)

(58) Field of Classification Search
CPC ........ A61B 17/12109; A61B 17/12036; A61B 17/12122; A61B 17/12136;
(Continued)

(56) References Cited

U.S. PATENT DOCUMENTS 5,618,266 A * 4/1997 Liprie ............... A61M 25/1002
600/3
5,738,652 A 4/1998 Boyd et al.
(Continued)

FOREIGN PATENT DOCUMENTS

WO 97/048436 A2 12/1997
WO 9929363 A1 6/1999

OTHER PUBLICATIONS

European Supplementary Search Report for EP14797277, completed Dec. 5, 2016.
International Search Report, dated Feb. 3, 2015.

Primary Examiner — Theodore Stigell
(74) Attorney, Agent, or Firm — Richard Cates

(57) ABSTRACT

Embodiments of aortic occlusion devices are described herein that include radially expandable and collapsible proximal and distal end portions, such as annular self-expanding stents or frames, that are configured to radially expand within an aorta to secure the device within the aorta. The devices can also include a catheter extending axially between the distal end portion and the proximal end portion and a porous covering, or filter, positioned around the catheter and between the proximal end portion and the distal end portion and configured to filter emboli from blood flowing into upper-body arteries. The device can further include a one-way valve positioned at or adjacent to the distal end portion of the device and configured to restrict retrograde blood flow through the device toward the heart.

15 Claims, 55 Drawing Sheets

(51) Int. Cl.
*A61M 1/36* (2006.01)
*A61F 2/01* (2006.01)

(52) U.S. Cl.
CPC .. *A61B 17/12122* (2013.01); *A61B 17/12136* (2013.01); *A61B 17/12145* (2013.01); *A61F 2/01* (2013.01); *A61M 1/34* (2013.01); *A61M 1/3666* (2013.01); *A61F 2002/011* (2013.01); *A61M 2205/3331* (2013.01)

(58) Field of Classification Search
CPC .......... A61B 17/12145; A61B 17/1215; A61B 17/1204; A61M 1/3666; A61M 1/34; A61F 2/01; A61F 2002/011
See application file for complete search history.

(56) References Cited

U.S. PATENT DOCUMENTS

| | | | |
|---|---|---|---|
| 6,547,760 B1* | 4/2003 | Samson | A61B 17/12045 604/101.01 |
| 6,579,259 B2 | 6/2003 | Stevens et al. | |
| 8,118,859 B2 | 2/2012 | Tenne | |
| 8,460,368 B2 | 6/2013 | Taylor et al. | |
| 2005/0228438 A1* | 10/2005 | Sachar | A61F 2/013 606/200 |
| 2006/0253148 A1 | 11/2006 | Leone et al. | |
| 2010/0179585 A1 | 7/2010 | Carpenter et al. | |
| 2010/0228280 A1* | 9/2010 | Groothuis | A61F 2/013 606/200 |

* cited by examiner

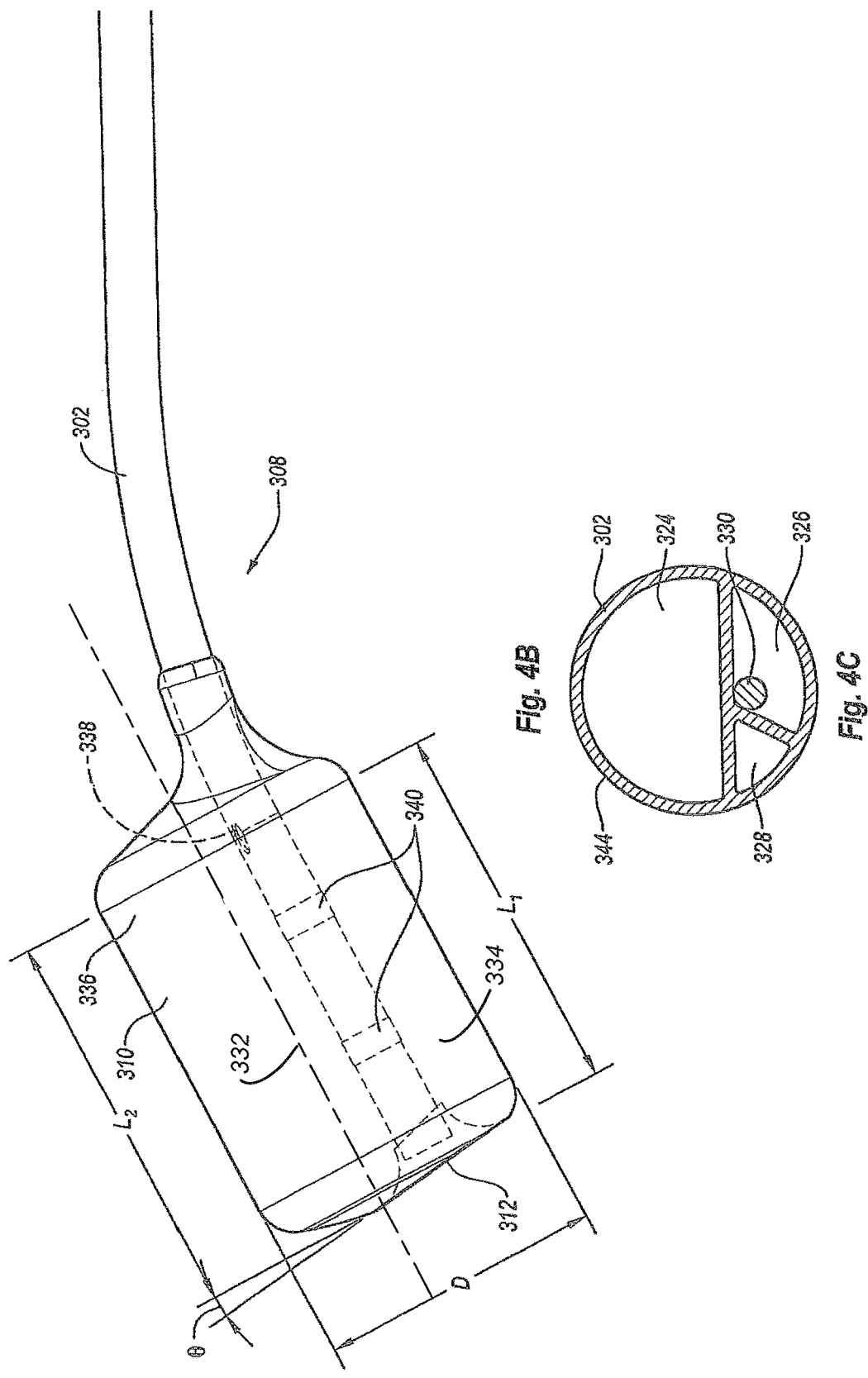

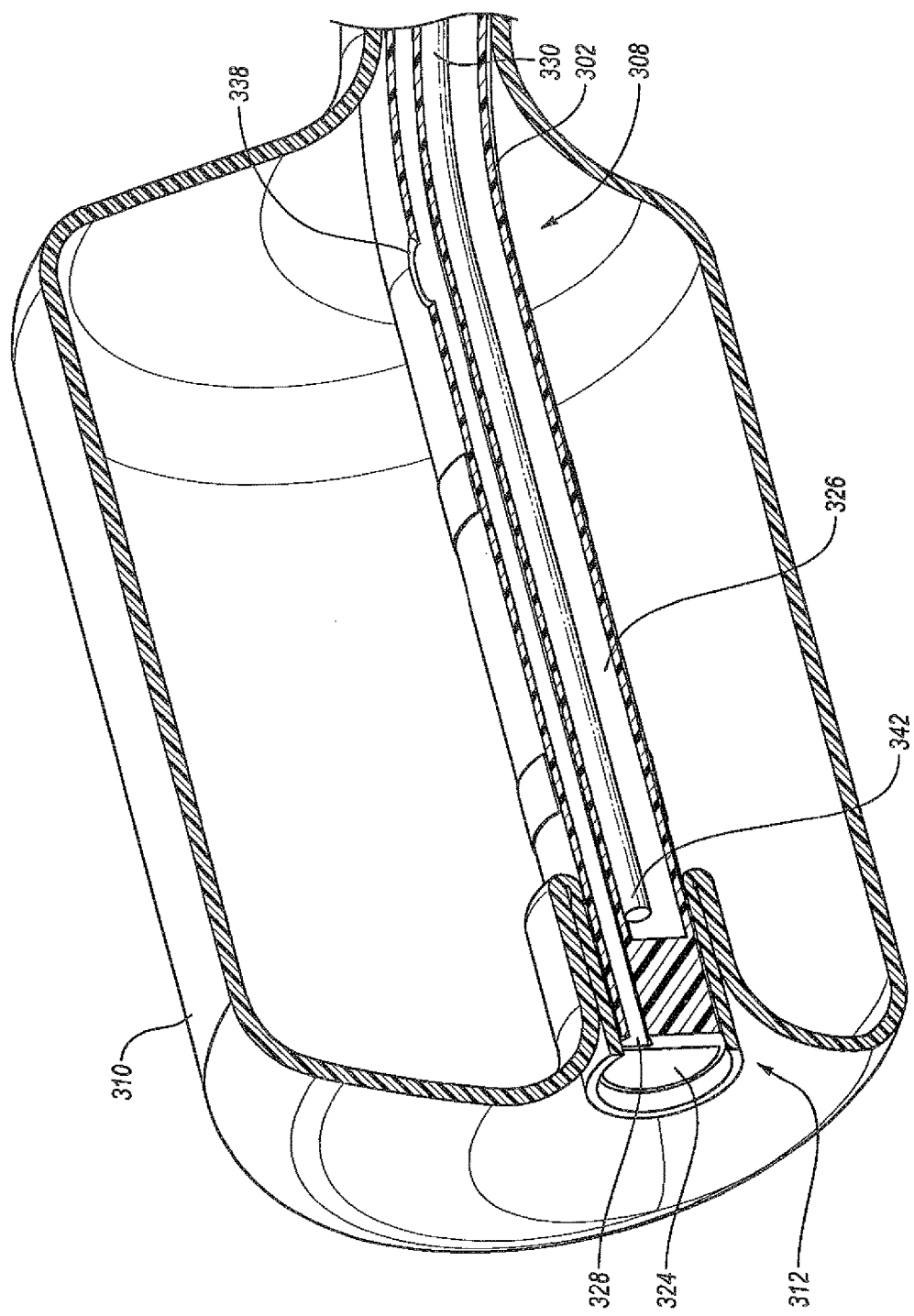

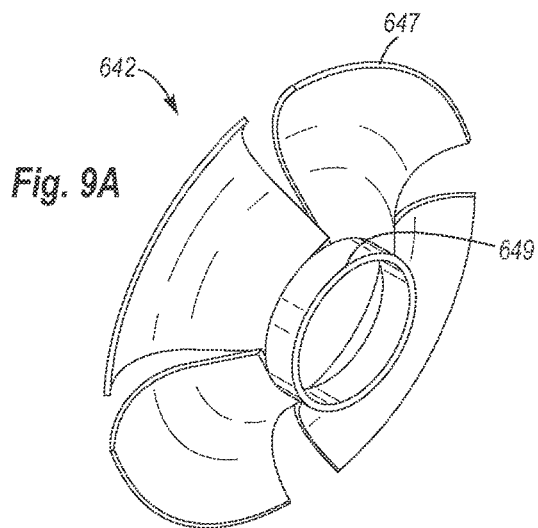
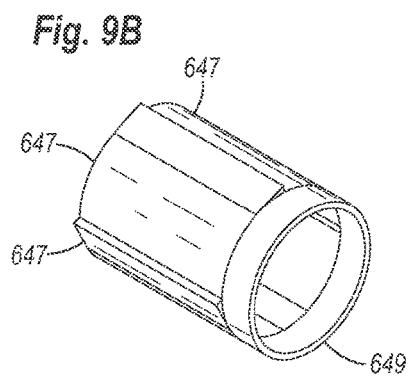
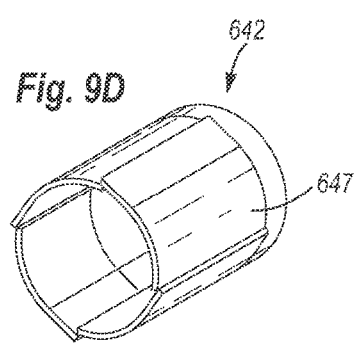
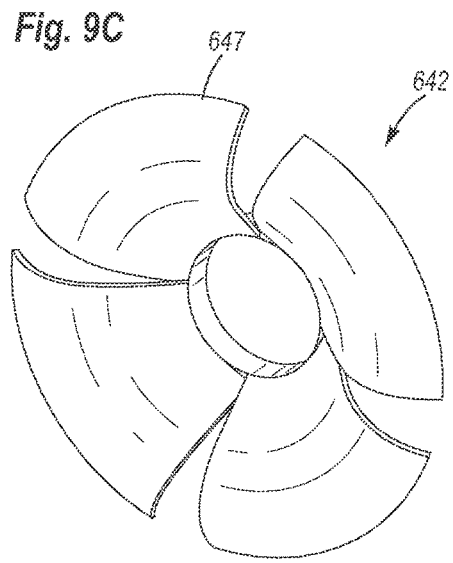

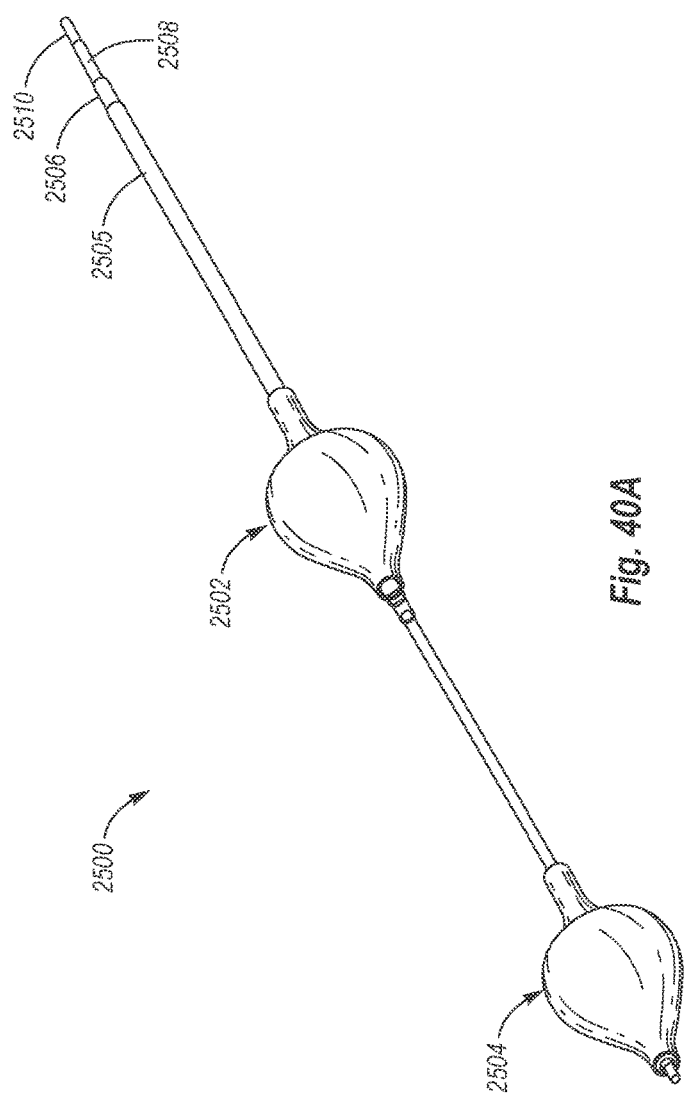
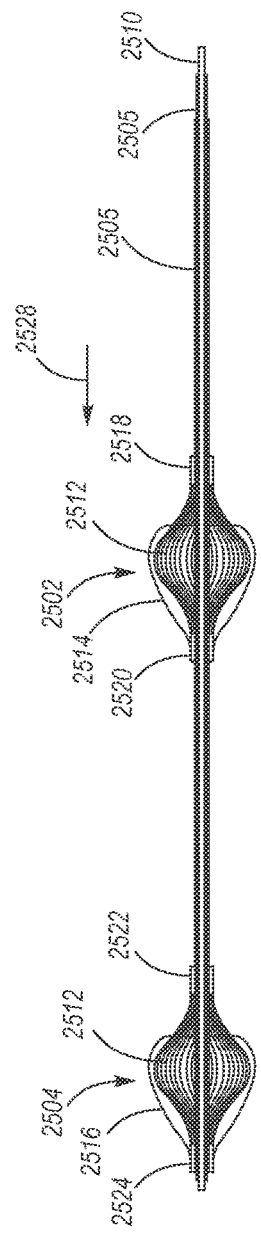

AORTIC OCCLUSION DEVICE

CROSS REFERENCE TO RELATED APPLICATION

This application claims the benefit of U.S. Provisional Patent Application No. 61/822,796 filed on May 13, 2013, which is incorporated herein by reference in its entirety.

FIELD

This disclosure relates generally to devices and techniques for performing cardiac procedures and particularly to catheter systems and methods for inducing cardioplegic arrest to facilitate the performance of cardiac procedures.

BACKGROUND

Techniques for performing major surgeries such as coronary artery bypass grafting and heart valve repair and replacement generally require open access to the thoracic cavity through a large open wound, known as a thoracotomy. Typically, the sternum is cut longitudinally (i.e., a median sternotomy), providing access between opposing halves of the anterior portion of the rib cage to the heart and other thoracic vessels and organs. An alternate method of entering the chest is via a lateral thoracotomy, in which an incision, typically 10 cm to 20 cm in length, is made between two ribs. A portion of one or more ribs may be permanently removed to optimize access.

In procedures requiring a median sternotomy or other type of thoracotomy, the ascending aorta is readily accessible for placement of an external cross-clamp, and for introduction of a cardioplegic fluid delivery cannula and venting cannula through the aortic wall. However, such surgery often entails weeks of hospitalization and months of recuperation time, in addition to the pain and trauma suffered by the patient. Moreover, while the average mortality rate associated with this type of procedure can be significant for first-time surgery, mortality and morbidity can be significantly increased for reoperation. Further, significant complications may result from such procedures. For example, application of an external cross-clamp to a calcified or atheromatous aorta may cause the release of emboli into the brachiocephalic, carotid or subclavian arteries with serious consequences such as strokes.

Methods and devices have therefore been developed for isolating the heart and coronary arteries from the remainder of the arterial system, arresting cardiac function, and establishing cardiopulmonary bypass without the open-chest access provided by a median sternotomy or other type of thoracotomy. In particular, methods and devices have been developed which facilitate the delivery of cardioplegia sufficiently to allow the heart to be placed under cardioplegic arrest with full cardiopulmonary bypass, without requiring open-chest access to the heart and without requiring an incision or puncture in the aorta, in the pulmonary artery, or in the heart wall.

SUMMARY

Embodiments of aortic occlusion devices are described herein that include radially expandable and collapsible proximal and distal end portions, such as annular self-expanding stents or frames, that are configured to radially expand within an aorta to secure the device within the aorta. The devices can also include a catheter extending axially between the distal end portion and the proximal end portion and a porous covering, or filter, positioned around the catheter and between the proximal end portion and the distal end portion and configured to filter emboli from blood flowing into upper-body arteries. The device can further include a one-way valve positioned at or adjacent to the distal end portion of the device and configured to restrict retrograde blood flow through the device toward the heart.

In another representative embodiment, a method of occluding blood flow through the aorta comprises inserting an aortic occlusion device in a radially collapsed state into a patient's vasculature, and positioning the aortic occlusion device in the aorta such that a distal end portion of the device is located substantially adjacent the ascending aorta and a proximal end portion of the device is located substantially adjacent the descending aorta. The method can further comprise causing the aortic occlusion device to radially expand such that the device is retained in the aorta and configured to restrict retrograde blood flow through the device toward the heart. The device can also be configured to filter emboli from blood flowing from the aorta into at least one of the brachiocephalic artery, the carotid artery, or the subclavian artery.

In another representative embodiment, a system for occluding the aorta comprises an aortic occlusion device including a radially expandable and collapsible proximal end portion and a radially expandable and collapsible distal end portion. The aortic occlusion device can further include a catheter extending axially between the distal end portion and the proximal end portion, a porous covering positioned around the catheter and between the proximal end portion and the distal end portion, and can be configured to restrict retrograde blood flow through the device toward the heart when deployed in the aorta. The system can further comprise a cardiopulmonary bypass machine configured to provide a flow of oxygenated blood to the aortic occlusion device via the descending aorta in a retrograde flow direction, such that the oxygenated blood can be filtered by the porous covering. The system can also include a source of cardioplegia fluid in fluid communication with the catheter.

The foregoing and other objects, features, and advantages of the disclosed technology will become more apparent from the following detailed description, which proceeds with reference to the accompanying figures.

BRIEF DESCRIPTION OF THE DRAWINGS

FIG. 4B is side view of the distal end of the antegrade cardioplegia delivery catheter of FIG. 4A.

FIG. 4C is a cross-sectional view of a catheter shaft of the antegrade cardioplegia delivery catheter of FIG. 4A.

FIG. 4D is a perspective cross-sectional view of an atraumatic tip of the antegrade cardioplegia delivery catheter of FIG. 4A.

FIGS. 9A-9D are perspective views of a sealing member of the embodiment of FIG. 8A.

FIG. 35C is a side elevation view of the embodiment of FIG. 35a.

FIG. 40A is a perspective view of another embodiment of an aortic occlusion device.

FIG. 40B is a side elevation view of the embodiment of FIG. 40A.

FIG. 40G is a perspective view of a second enclosure of the embodiment of FIG. 40a.

DETAILED DESCRIPTION

Exemplary embodiments of the present disclosure are directed to accessing a body lumen in order to perform a medical procedure. For instance, during a minimally invasive surgical procedure, a surgeon may access a body lumen such as the femoral artery or jugular artery, and extend one or more elements through the vasculature of the patient so as to access a location remote from the access site. Devices that may be extended through the access site and to a remote location of the surgical procedure include catheters, stents, guidewires, other surgical devices, or any combination of the foregoing. Thus, a variety of surgical procedures may be performed within the cavities of the body, particularly including minimally invasive and less invasive surgical procedures in which surgical instruments are introduced through an access site, and thereafter extended through body lumens to a desired location.

Figure 1:
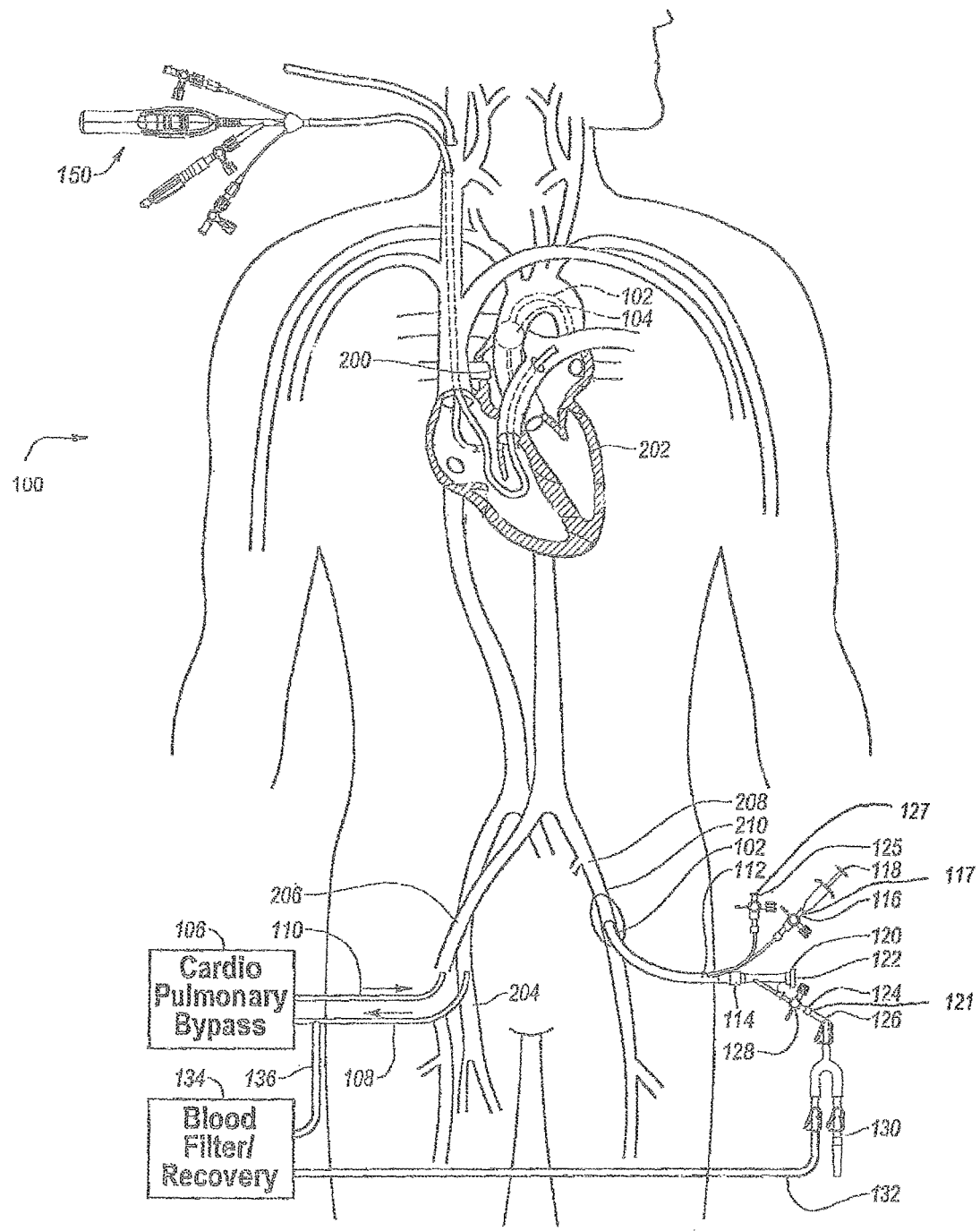
FIG. 1 schematically illustrates an exemplary cardiac access system.

FIG. 1 schematically illustrates an exemplary cardiac access system 100 and various individual components thereof. The cardiac access system 100 may also be referred to as a cardiac occlusion system as, in some embodiments, the cardiac access system 100 may occlude the aorta, coronary sinus, and/or other cardiac vasculature or lumens. The cardiac access system 100 illustrated in FIG. 1 is intended to provide a general overview of one example of a suitable system for accessing a patient's heart or a portion thereof, and is not intended to be an exhaustive illustration of all components or mechanisms that may be in use during a cardiac procedure.

The cardiac access system 100 can include a first delivery catheter 102. In this embodiment, the first delivery catheter 102 is elongated and is used to access the aorta, although the first delivery catheter 102 may optionally be used to occlude or access other lumens within the body. In the illustrated embodiment, an expandable member 104 located at a distal portion of the delivery catheter 102. When the expandable member 104 is inflated or otherwise expanded, such as is illustrated in FIG. 1, the expandable member 104 may occlude the ascending aorta 200, thereby separating the left ventricle 202 and the upstream portion of the ascending aorta 200 from the rest of the patient's arterial system. Expansion of the expandable member 104 may also be used to securely position the distal end of the delivery catheter 102 within the ascending aorta 200, as the exterior of the expandable member 104 may expand to engage the interior surface of the ascending aorta 200.

In the illustrated embodiment, a cardiopulmonary by-pass system 106 may be used to remove venous blood from the body by, for instance, being placed in fluid communication with the femoral vein 204. A blood withdrawal catheter 108 may connect to the femoral vein 204 and the cardiopulmonary by-pass system 106 and be used to remove blood so as to allow the cardiopulmonary by-pass system 106 to remove carbon dioxide from the blood, oxygenate the blood, and then return the oxygenated blood to the patient. The oxygenated blood may be returned through a return catheter 110 that accesses the femoral artery 206. The oxygenated blood may be returned at sufficient pressure so as to flow throughout the patient's arterial system except for the portion blocked by the expanded occluding member 104 on the aortic occluding catheter 102.

The first delivery catheter 102 of the illustrated embodiment extends through the descending aorta to the left femoral artery 208 and out of the patient through an access site 210, which may be formed as a cut down or in any other suitable manner. A proximal section 112 of the catheter 102 may extend out of the patient through the access site 210. In this embodiment, an adapter 114 may connect to the proximal section 112 of the catheter 102. The adapter 114 is illustrated as having four arms, although a suitable adapter may have more or less than four arms. In one embodiment, a first arm 116 with a first access port 117 may be adapted for use with the expandable member 104. For instance, an inflation device 118 may be used to inject air or some other fluid that can inflate the expandable member 104. A second arm 120 optionally includes a main access port 122 through which instrumentation or other materials or components may pass. For instance, endovascular devices, valve prostheses, angioscopes, irrigation or cardioplegic fluids, or other components or materials, or any combination of the foregoing, may pass through the main access port 122, through the catheter 102, and out of a distal port 123 (FIG. 2) of the catheter 102. In one example embodiment, the main access port 122 is coupled to a source of cardioplegic fluid (not shown) which is delivered through the catheter 102 to arrest the patient's heart.

The adapter 114 of FIG. 1 also includes a third arm 124 with a third access port 121 connected to a by-pass line 126 that is provided to direct blood, irrigation fluid, cardioplegia solution, and the like to or from the system. A suitable valve 128 may also be provided to open and close the by-pass line 126 and/or direct fluid passing through the by-pass line to a discharge line 130 or a line 132 to a blood filter and recovery unit 134. A return line 136 may be provided to return any filtered blood to the cardiopulmonary by-pass system 106. In this embodiment, the adapter 114 also includes a fourth arm 125. The fourth arm 125 with fourth access portion 127 may, in some embodiments, be in fluid communication with the aortic root (e.g., through a pressure port in the distal end of the catheter 102) and/or a pressure monitoring device (not shown) proximate the adapter 114. Thus, the fourth arm 125 may facilitate measuring of the root pressure within the patient's aorta.

Figure 2:
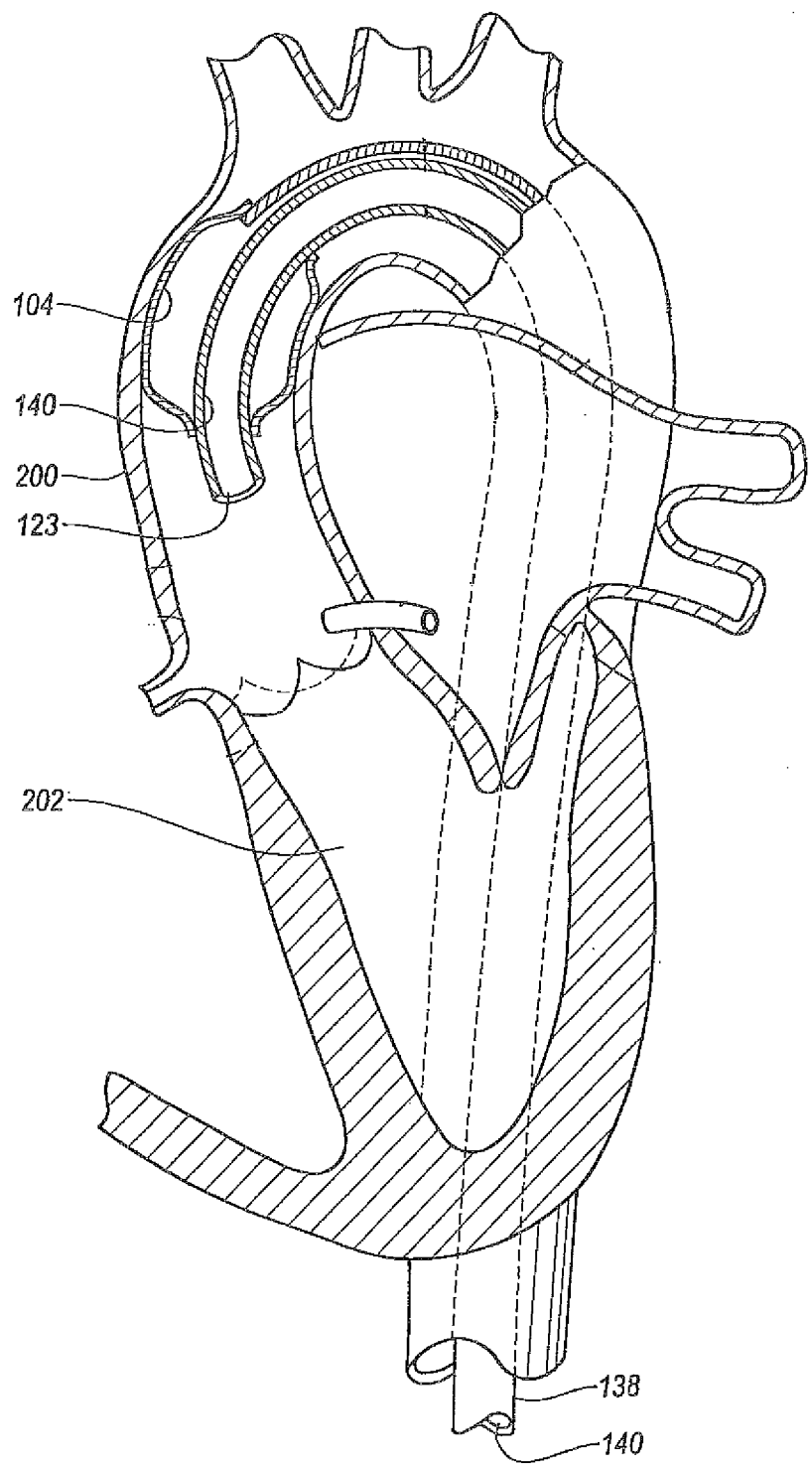
FIG. 2 is an enlarged partial section view of the cardiac access system of FIG. 1, particularly illustrating an occluding catheter disposed within the aorta.
Figure 3:
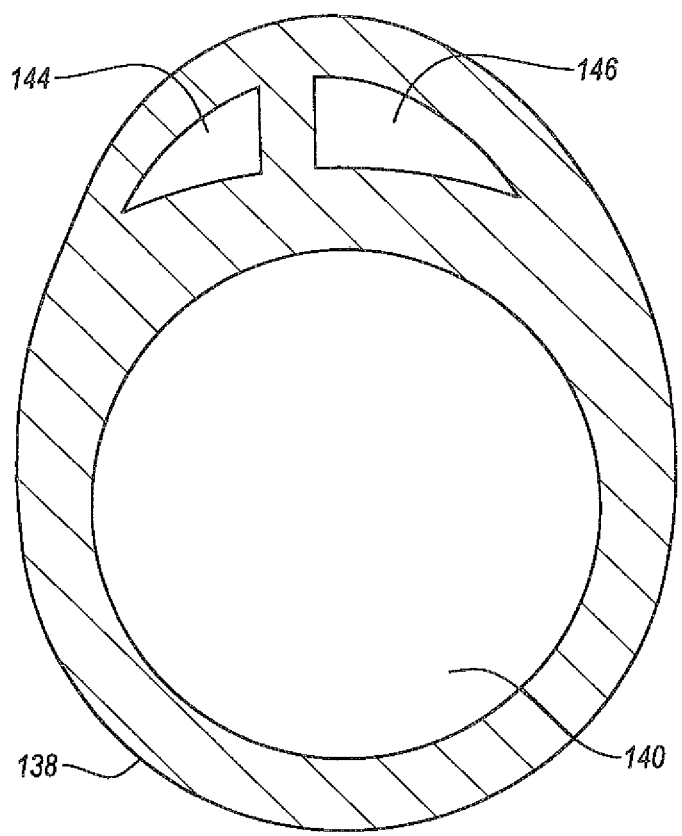
FIG. 3 is a transverse cross-sectional view of the exemplary occluding catheter of FIG. 2.

The operation of the first delivery catheter 102 may be understood more completely upon a description of the operation of the catheter 102 within the patient's heart and related vasculature. With reference now to FIGS. 2 and 3, the first delivery catheter 102 may include an elongated body in the form of a shaft 138 having an interior lumen 140 accessible through the main access port 122 (see FIG. 1). At the distal end of the shaft 138, there may be a coil.

The shaft 138 may include second and/or third interior lumens 144, 146 in some embodiments. The second interior lumen 144 may, for instance, be in fluid communication with the interior of the expandable member 104, which can be an occluding balloon. To inflate the balloon, a gaseous or liquid fluid may pass from the inflation device 118 (FIG. 1) and through the second interior lumen 144 to the expandable member 104. Similarly, a fluid may pass through the second interior lumen 144 and from the expandable member 104, towards the proximal end of the shaft 138 as the expandable member 104 is deflated. The third interior lumen 146 may be in fluid communication with a pressure port at or near the distal end of the shaft 138, as well as with a pressure sensor (e.g., coupled to the fourth arm 125 of the adapter 114 in FIG. 1). Through the third interior lumen 146, pressure in the aortic root and between the aortic annulus and sinotubular junction may be measured.

The shaft 138 and/or expandable member 104 can be shaped and sized in a manner to facilitate insertion and removal of the catheter 102, and or occlusion of the ascending aorta 200 by the expandable member 104. As discussed in greater detail herein, the shaft 138 may have a pre-determined and manufactured contour at the distal end thereof, such that the shaft 138 may have an internal bias causing the shaft 138 to have the desired contour when in an unstressed state. Such contour may generally conform to the shape of all or a portion of the aortic arch and thereby facilitate positioning of the expandable member 104 in the ascending aorta 200, and between the coronary ostia and the brachiocephalic artery. The pre-determined contour at the distal end can be manually or otherwise straightened for introduction of the aortic occlusion catheter 102 in a peripheral artery (e.g., the femoral artery 208 of FIG. 1). Alternatively, the shaft 138 may be manufactured as having a generally straightened configuration, and such shaft 138 may be positioned once inside the patient to obtain the pre-determined contour. Such positioning may occur automatically or may be manually performed by a surgeon. Particular example embodiments of a suitable first delivery catheter 102 are described in greater detail herein.

With reference to FIGS. 1-3, set-up of the cardiac access system 100 will be described in additional detail. More particularly, to set up the cardiac access system 100, the patient may initially be placed under light general anesthesia. The withdrawal catheter 108 and the return catheter 110 of the cardiopulmonary by-pass system 106 can be percutaneously introduced into the right femoral vein 154 and the right femoral artery 156, respectively. An incision 210 may be made in the left groin to expose the left femoral artery 208, and the aortic occluding catheter 102 is inserted into the left femoral artery 208 through the incision 210 and advanced upstream until the expandable member 104 of the occluding catheter 102 is within the ascending aorta 200. Antegrade cardioplegic fluid may then pass through the occluding catheter 102 and into the aorta. In one embodiment, an initial volume of about 1000-1500 ml of cardioplegic fluid is delivered through the interior inner lumen 140 of the aortic occlusion catheter 102, and such delivery may initiate cardioplegic arrest, after which cardioplegic arrest may be maintained by retrograde delivery through the delivery catheter 150.

The operation of the cardiopulmonary by-pass unit 106 can be initiated to withdraw blood from the femoral vein 204 through the catheter 108, remove $CO_2$ from the withdrawn blood, add oxygen to the withdrawn blood, and then pump the oxygenated blood through the return catheter 110 to the right femoral artery 206. The expandable member 104 may then be inflated or otherwise expanded to occlude the ascending aorta 200, causing the blood pumped out of the left ventricle to flow through a discharge port 123 into the first interior lumen 140 of the occluding catheter 102. The blood may flow through the interior lumen 140 and out the third arm 124 of the adapter 114 into the by-pass line 126 and then into a blood filter and recovery unit 134 through the valve 128 and line 132. For blood and irrigation fluids containing debris and the like, the position of the valve 128 may be changed to direct the fluid through the discharge line 130.

With the cardiopulmonary by-pass system in operation, the heart may become completely paralyzed and stop pumping. The left atrium may become decompressed and the ascending aorta can be blocked by the expandable member 104 on the occluding catheter 102. At such point in time, the heart may be appropriately prepared for a cardiac procedure. The procedures with which the system and method of the present disclosure are useful include thoracoscopic coronary artery bypass grafting, thoracoscopic or endovascular repair or replacement of the mitral, aortic and other valves, thoracoscopic repair of atrial or ventricular septal defects and other congenital defects, transmyocardial laser revascularization, electrophysiological mapping and ablation, and various other procedures which require or would benefit from the inducement of cardioplegic arrest. The present disclosure may also be utilized to induce cardioplegic arrest in conventional open surgical procedures as a substitute for conventional external aortic cross-clamps and conventional cardioplegia cannula introduced directly into the heart and/or aorta.

Figure 4A:
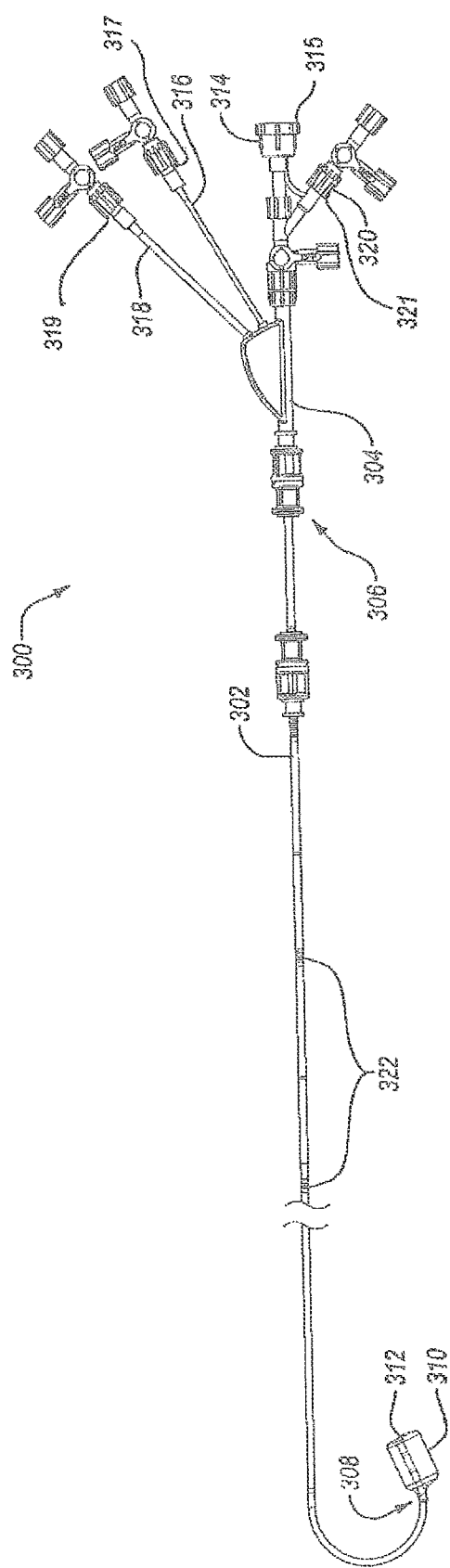
FIG. 4A is a side perspective view of an exemplary antegrade cardioplegia delivery catheter.

Turning now to FIG. 4A, an exemplary embodiment of a delivery catheter 300, and more particularly an antegrade cardioplegia delivery catheter or aortic occlusion catheter, is illustrated and described in additional detail. In the illustrated embodiment, the delivery catheter 300 includes a catheter shaft 302 that can be inserted into a patient and located at a desired location, such as within the ascending aorta of the patient. Accordingly, the shaft 302 may have a length such that when a distal end 308 of the shaft 302, including an expandable member 310, is at a desired location within the patient, a proximal end 306 of the shaft 302 may remain exterior to the patient. The proximal end 306 of the shaft 302 may be positioned, for instance, adjacent a peripheral access site, such as in the femoral artery to facilitate a minimally invasive procedure. A hub 304 may also be attached to the shaft 302. The hub 304 may serve any number of purposes. For instance, in the embodiment shown in FIG. 4A, the hub 304 may have various extension arms 314, 316, 318, 320 that serve various purposes. Such extension arms may, for instance, facilitate expansion of the expandable member 310, delivery of cardioplegic fluid, monitoring of pressure or characteristics within the vasculature at the distal tip 312, insertion of guidewires, stents, replacement valves, other devices or components, or any combination of the foregoing.

Similar to the manner discussed above with regard to the system 100 of FIGS. 1-3, and more particularly with respect to the delivery device 102 of FIGS. 1-3, the delivery catheter 300 may be used to occlude a portion of a patient's vasculature at or near the heart, while also supplying cardioplegic fluid to the heart. An exemplary manner in which the delivery catheter 300 can be used to occlude vasculature is may be understood particularly with reference to FIG. 4B-4D.

In particular, to facilitate such occlusive functions, the delivery catheter 300 may include an expandable member 310. The expandable member 310 may be generally positioned at the distal end 308 of the shaft 302, and may be proximate or adjacent a distal tip 312 of the shaft 302. The expandable member 310 may be configured to vary its size, diameter, or other dimension in any suitable manner. In some embodiments, the expandable member 310 is an expandable balloon. By way of illustration, the expandable member 310 may be formed of a flexible material. The expandable member 310 may, for instance, be polyurethane, PTFE, or other material that is blow-molded, dip-molded, or otherwise formed. The expandable member 310 may also be formed of other materials, formed in other manners, or take other forms. For instance, the expandable member 310 need not be a balloon, and could be any other suitable type of selectively expandable element.

The expandable member 310 of FIGS. 4B and 4D is illustrated in an expanded state. It should be appreciated, however, that the expandable member 310 may be inserted into a patient while in a collapsed, partially collapsed, or other state that may allow the expandable member 310 to pass more easily through the patient's vasculature. In some embodiments, as the expandable member 310 moves through the vasculature, the expandable member 310 does not substantially occlude the vasculature, at least not until the distal tip 312 of the shaft 302 is at or near an intended location. Once at the desired location, the expandable member 310 may be expanded.

Expansion of the expandable member 310 may be performed in any suitable manner. For instance, where the expandable member 310 is an expandable balloon, a fluid may be selectively passed through the shaft 302 and into the expandable member 310. In FIG. 4A, for instance, the shaft 302 may connect to the hub 304, and may be in fluid communication with one or more of the various extension arms 314, 316, 318, 320. The shaft 302 may have one or more lumens therein to receive fluid, instruments, or other items. For instance as best shown in FIGS. 4C and 4D, the shaft 302 may have a multi-lumen design. Each of the multiple lumens 324, 326, 328 may be in communication with the one or more extension arms 314, 316, 318, 320 (FIG. 4A) with access ports 315, 317, 319, 321, which may act as access ports to the respective lumens 324, 326, 328.

In the illustrated embodiment, the shaft 302 may include a primary lumen 324 and multiple secondary lumens 326, 328. The secondary lumen 326 may, for instance, extend along a length of the shaft 302 and terminate at a location within the expandable member 310. As shown in FIG. 4D, for instance, the secondary lumen 326 may terminate near the distal tip 312 of the shaft 302. The secondary lumen 326 may be in fluid communication with an inflation port 338 that extends through a sidewall of the shaft 302. The inflation port 338 can be within the expandable member 310, such that as fluid is inserted through the lumen 326 and exits the shaft 302 through the inflation port 338, the expandable member 310 may inflate or otherwise expand. Conversely, fluid dispelled from the expandable member 310 may pass through the inflation port 338 and into the shaft 302 as the expandable member 310 contracts.

The expandable member 310 may have any number of suitable constructions or configurations. For instance, in FIG. 4B, the expandable member 310 is illustrated as an inflated balloon having a generally elongated, hexagonal side profile, and with the shaft 302 being eccentric relative to the central axis 332 of the expandable member 310. The particular dimensions and configuration of the expandable member 310 can vary as desired to, for example, occlude an ascending aorta of a patient. In some embodiments, the dimension D corresponds to a diameter or width of the expandable member 310 and can generally correspond to the width of the ascending aorta at a desired occlusion location. For instance, the ascending aorta in an average adult may measure between about 3.5 and about 3.8 cm. Accordingly, in some embodiments, the expanded diameter D is about 3 cm to about 4 cm. The working length $L_1$ may also correspond to a length of the expandable member 310 that can engage the lower surface of the aorta to facilitate occlusion. In general, an increased working length $L_1$ increases the surface area for contact with the aorta and favors stabilizing the position of the expandable.

The expandable member 310 may generally be considered has being divided by the shaft 302 into a lower portion 334 and an upper portion 336. In this embodiment, the upper and lower portions 334, 336 have different lengths $L_1$, $L_2$. The eccentric profile of the shaft 302 may provide differing sizes of portions 334, 336; however, the general shape of the expandable member 310 may additionally or alternatively be varied. In this embodiment, for instance, the upper portion 336 may have a side surface extending at an angle φ from the distal tip 312, and to an upper contact surface, such that the length of the upper contact surface has the length $L_2$. The length $L_2$ may be greater or smaller than the working length $L_1$. In the illustrated embodiment, for instance, the angle φ may be between about ten and about twenty-five degrees, and more particularly between about thirteen and about twenty-one degrees. For instance, the angle φ may be between about fifteen and about eighteen degrees, such that the length $L_1$ is greater than the length $L_2$.

The expandable member 310 is but one example of a suitable expandable member, and other expandable members may be used. For instance, in other embodiments, the expandable member 310 may be spherical, trapezoidal, cylindrical, barrel-shaped, or otherwise configured. Moreover, the degree of eccentricity of the shaft 302 relative to the central axis 332 may also be varied. For instance, the shaft 302 may be concentric with the axis 332 (i.e., 0% eccentricity) or may vary up to nearly 100% eccentricity (i.e., the shaft at the upper or lower surface of the expandable member). In one embodiment, the eccentricity of the shaft 302 may be between about 5% and about 36%.

To facilitate cardioplegic functions of the delivery catheter 300, the delivery catheter 300 may allow cardioplegic fluid to be passed from a fluid source or reservoir and into the ascending aorta or other location within a patient. FIGS. 4C and 4D illustrate a particular manner in which such features can be provided. For instance, as noted previously, the shaft 302 optionally includes multiple fluid conduits, channels, lumens, or other features. In particular, in the illustrated embodiment, the shaft 302 may include a primary lumen 324 that is optionally in fluid communication with an extension arm 314 that acts as a port to allow the introduction of cardioplegic fluid, guidewires, surgical instruments, or other elements. Cardioplegic fluid may be pressurized and passed through the lumen 324 towards the distal tip 312 of the shaft 302. As best shown in FIG. 4D, the distal end of the shaft 302 may include an opening generally corresponding to the lumen 324. For instance, the lumen 324 may be open at the distal tip 312 such that the pressurized cardioplegic fluid exits the shaft 302 distal to the expandable member 310.

Figure 6A:
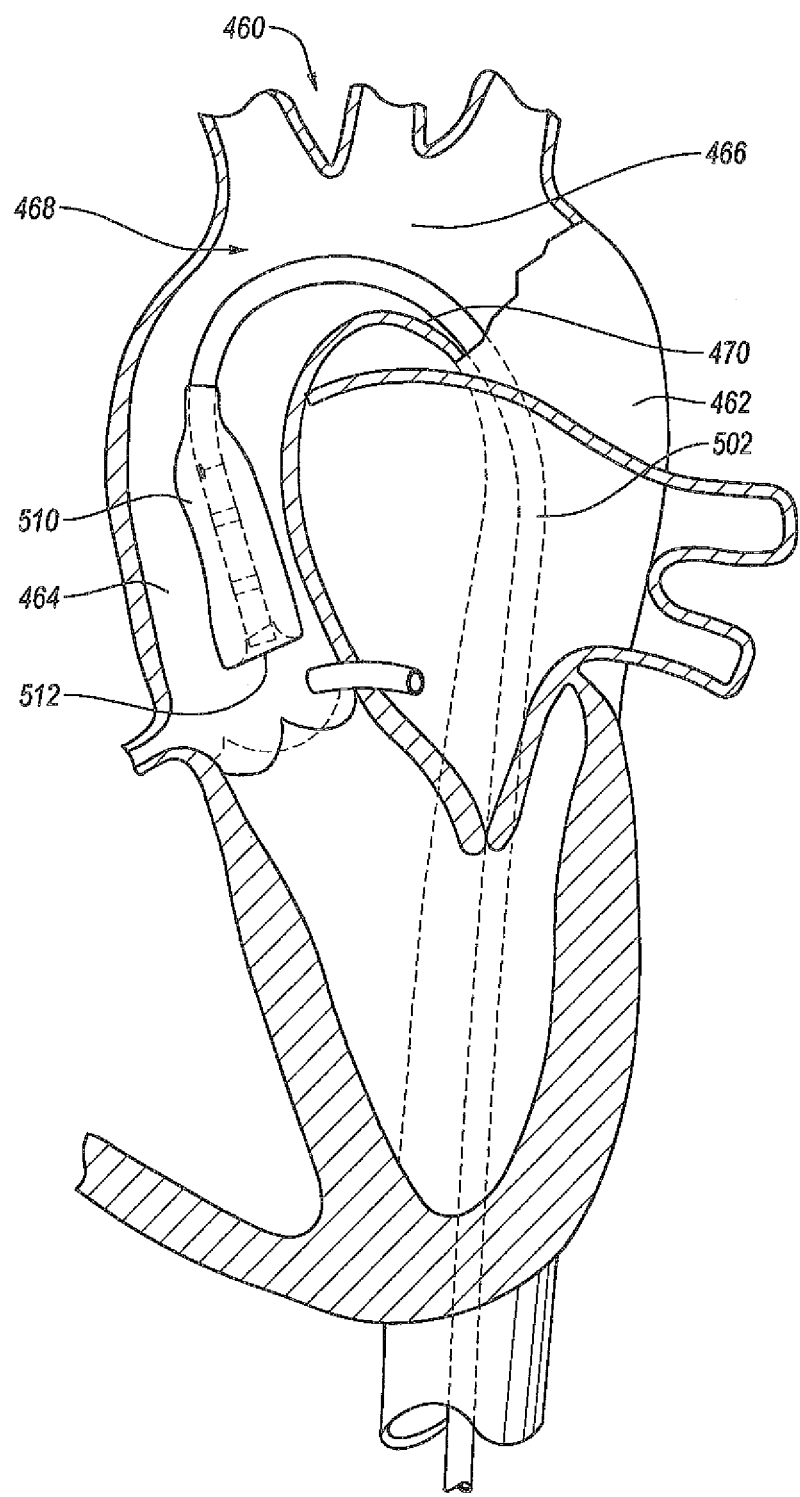
FIGS. 6A-6C are partial cross-sectional views of the distal end of an antegrade cardioplegia delivery catheter used to occlude a portion of the ascending aorta.

In some embodiments, the distal tip 312 may be integrally formed with the shaft 302, although in other embodiments the distal tip 312 and shaft 302 are separate components that are bonded together. For instance, the distal tip 312 may be a molded, extruded, or otherwise formed component that is bonded to the shaft 302 using a thermal, adhesive, laser welding, overmolding, or other procedure. As best shown in FIG. 6A, in some embodiments, the expandable member 510 may extend at least slightly distal relative to the distal tip 512. In such an embodiment, the lumens at the distal tip 512 may be protected by the expandable member 510. For instance, a distal leg of the expandable member 510 may connect to the distal tip 512 of the shaft 502. If the distal tip 512 is lodged into a vascular wall, the lumens of the distal tip may remain patent and able to deliver fluid, monitor cardiac or vascular characteristics, receive fluid, or the like.

The delivery catheter 310 may provide still other features and uses. For instance, cardiac and/or vascular characteristics can be monitored using the delivery catheter 310. Such characteristics may include, for instance, flow rates, beat rates (if any), pressure, or dimensions, or other characteristics. In one embodiment, such as where the delivery catheter 310 is configured to occlude the ascending aorta, the delivery catheter 310 may be adapted to measure a pressure within the aorta, such as the aortic root pressure. As shown in FIGS. 4C and 4D, for instance, a secondary lumen 328 may extend to a vent at or near the distal tip 312 of the shaft 302. The secondary lumen 328 may be in fluid communication with a pressure monitoring device (e.g., through a connection at extension arm 318 of FIG. 4A), thereby allowing root aortic pressure to be monitored throughout a surgical or other procedure.

The delivery catheter 300 may be configured to provide any number of features. In accordance with some embodiments, the shaft 302 may be adapted to provide still other features and aspects. For instance, as shown in FIG. 4A, the shaft 302 may include one or more markings 322 thereon. Such markings may be bands, ink, radiopaque markers, or otherwise structured to facilitate visualization inside or outside the patient. For instance, in one embodiment, the markings 322 are radiopaque markings that are visible under transesophageal echocardiography visualization or other visualization techniques, so as to facilitate positioning of the shaft within a patient. Where an expandable member 310 is to be placed at a particular location, the expandable member 310 may optionally include additional markings (e.g., platinum iridium markers) to facilitate visualization. For instance, as best shown in FIG. 4B, one or more markings 340 may be placed on, within, or proximate the expandable member 310 to thereby allow identification of a position of the expandable member 310 when a particular visualization technique is used.

The shaft 302 may be otherwise structured to facilitate insertion, removal, and/or placement of the delivery catheter 300 during a surgical procedure. For instance, as shown in FIGS. 4C and 4D, the shaft 302 may include two components. Such components include, in this embodiment, a body element 344 and a core element 330. The body element 344 may, for instance, generally define the shape of the shaft 302 and the lumens 324, 326, 328 within the shaft. In one embodiment, the body element 344 may be formed of any suitable material and using any number of different manufacturing processes. For instance, the body element 344 may be formed from a flexible material that can bend as the shaft 318 translates through a patient's vasculature, to thereby match contours within the patient's body. Suitable materials may include, for instance, ethylene tetrafluoroethylene (ETFE) or polytetrafluoroethylene (PTFE). In another embodiment, the outer shell 305 is formed from a biocompatible material such as Pebax®. A body element 344 is produced from Pebax® which may be extruded and can even be extruded to simultaneously define multiple lumens. Accordingly, the body element 344 is optionally a multi-lumen extrusion, although in other embodiments the body element 344 may be formed as a separate fluid lines layered together with a heat shrink wrap holding them together. In at least some embodiments, the durometer of the body element 344 may be between about 20 to about 80 Shore D. Such durometer may also change along the length of the body element 344. For instance, the durometer of the distal tip 312 may be lower relative to the durometer at a proximal end of the shaft 302.

In at least some embodiments, the body element 344 is a solid extrusion, rather than a wrap that includes coils or a supporting exoskeleton, wire frame, or the like. In at least one embodiment, such as that shown in FIGS. 4C and 4D, the shaft 302 may include a core 330 within the secondary lumen 326. The secondary lumen 326 may, as discussed previously, be used for facilitating expansion of the expandable member 310, or for any other desired feature. The core 330 may be a wire extending along all or a portion of the length of the shaft 302. The core 330 may have a stiffness and strength that provides additional column stiffness to facilitate placement of the shaft 302. The core 330 may additionally, or alternatively, provide kink resistance or define a desired shape of the shaft 302.

For instance, as reflected in FIG. 4A, the distal end 308 of the shaft 302 may have a bend, curve, or other shape. In some embodiments, the shaft 302 may be configured to pass through the descending aorta and into the ascending aorta. To do so, the curved distal end 308 may pass around a relatively tight curve radius, namely the curve radius defined by the aortic arch.

While curvature of the distal end 308 may be produced by allowing the body element 344 and/or core 330 to be made of a flexible material, in other embodiments the core is pre-designed and manufactured to maintain a specific curved profile. In still other embodiments, such curved profile may be selectively activated in the shaft 302. To obtain these and other characteristics, in one embodiment, the core 330 can be comprised of biocompatible materials that are at least temporarily deformable. Suitable biocompatible materials can include, for example, superelastic and/or shape memory materials (e.g., copper-zinc-aluminum; copper-aluminum-nickel; nickel-titanium alloys known as Nitinol; cobalt-chromium-nickel alloys, cobalt-chromium-nickel-molybdenum alloys, nickel-titanium-chromium alloys, and the like). In addition, other suitable materials may include stainless steel, silver, platinum, tantalum, palladium, cobalt-chromium alloys, niobium, iridium, any equivalents thereof, alloys thereof or combinations thereof.

Where the core 330 is formed of a shape memory material, the core 330 can be shaped in a manner that allows deformation from a pre-determined curved memory shape while the core 330 is outside the body lumen of a patient, but which can automatically retain the curved memory shape while within a body lumen. Shape memory materials have a shape memory effect in which they can be made to remember a particular shape. Once a shape has been remembered, the shape memory material may be bent out of shape or deformed and then returned to its original shape by unloading from strain or by heating. In one embodiment, for instance, the core 330 is formed of a shape memory material manufactured to remember, over at least a portion of the core 330, a curved shape generally corresponding to the curvature of an aortic arch. Such curvature need not correspond directly to the aortic arch, or may generally correspond to any of various portions of the aortic arch. For instance, the curvature of the core 330 may correspond to an upper curvature or central curvature of the aortic arch. As discussed in greater detail herein, the core 330 may alternatively have a memory shape configured to correspond to the bottom curvature of the aortic arch.

Activation of the core 330 to transition from a deformed state to a remembered shape may be performed in any manner, such as by applying a force on the core 330 (e.g., to induce a strain), or by placing the core 330 at a desired temperature. For instance, in one embodiment, the core 330 is trained to be thermally activated and transition from a deformed shape to a pre-determined shape when the core 330 is placed at about body temperature (e.g., about 37° C.). As the core 330 may be placed within the body element 344, the change in shape of the core 330 may also cause the body element 340 to change shape, thereby changing the shape and profile of the distal end 308 of the shaft 302. At body temperature, or when activated in another manner, the core 330 may move to the trained shape such that the radial strength increases, whereas at room temperature or another non-activated state, the core 330 may be relatively weak in the radial direction and may be readily deformable.

In some embodiments, the core 330 may be a wire, although the core 330 may take other forms. As best illustrated in FIG. 4D, the core 330 may be a wire having a variable cross-sectional shape. In particular, in at least one embodiment, the core 330 may have a distal end 342 at least proximate the distal end 308 of the shaft 302. As the core 330 approaches the distal tip 312 of the shaft 302, the size of the core 330 may, in some embodiments, decrease, such as by having a tapered, stepped, or other configuration. In such a manner, the strength of the core 330 at the distal tip 312 may be decreased, thereby also reducing the force that the core 330 can exert at the distal tip 312. With reduced force at the distal tip 312, trauma to a patient's vasculature may be decreased.

The shaft 302 and the hub 304 may be formed in any number of manners, or have any other number of features or configurations. For instance, the size of the shaft 302 may be varied as desired. In accordance with one embodiment, the shaft 302 may have an outer diameter of between about eight and ten French, so as to be passable from a peripheral artery through the descending aorta, and into the ascending aorta as described herein. Depending on other uses of the delivery catheter 300, the patient with whom the catheter 300 is used, or other factors, the size of the shaft 302 may be larger than ten French, or smaller than eight French.

The shaft 302 may be connected to the hub 304 in any suitable manner. For instance, in one embodiment, the shaft 302 and the hub 304 are an integral unit and are molded together. In another embodiment, the shaft 302 may be formed separate from the hub 304 and thereafter attached to the hub. For instance, the shaft 302 may be extruded and the hub 304 may be molded and then bonded to the shaft 302. Such bonding may be performed by a thermal bonding, overmolding, adhesive, or other attachment procedure. The extension arms 314, 316, 318, 320 may be similarly formed. For instance the extension arms 314, 316, 318, 320 may be molded and integrally formed with the hub 304. In some embodiments, the extension arms 314, 316, 318, 320 are flexible, but may be rigid. In at least one embodiment, some extension arms (e.g., arms 316, 318) may be flexible while other extension arms (e.g., arms 314, 320) are substantially rigid. As discussed herein, the extension arms 314, 316, 318, 320 with access ports 315, 317, 319, 321 may serve as ports and facilitate balloon inflation, aortic root pressure monitoring, cardioplegia delivery, aortic root venting, or other aspects.

In at least one embodiment, the hub 304 may further facilitate proper positioning of the distal end 308 of the shaft 302 within a patient. For instance, as discussed previously, the shaft 302 may have a predetermined curve or other profile. The predetermined curve or other profile may be fixed in relation to the orientation of the hub 304. Indicia (not shown) may be placed on the hub 304 to indicate the direction of the curved profile of the shaft 302 such that once the distal end 308 of the shaft 302 is within a patient, the surgeon or other operator will be aware by glancing at the hub 304 as to what direction the shaft 302 will bend or curve. In other embodiments, the hub 304 may be asymmetric. A direction of asymmetry may correspond with the curve of the shaft 302, thereby allowing the surgeon to glance at the hub 304, view the asymmetry, and know which direction the shaft 302 curves.

Turning now to FIGS. 5A-5C and FIGS. 6A-6C, various exemplary aspects of embodiments of the present disclosure are illustrated and described in greater detail, particularly with regard to the manner of use of an antegrade cardioplegia delivery catheter that occludes the ascending aorta of a patient. For instance, FIGS. 5A-5C generally illustrate a process of inserting a shaft 402 and expandable member 410 of a delivery catheter into a patient's aorta 460, expanding the expandable member 410, and retracting expandable member 410 to secure the expandable member in an occluding position.

Figure 5A:
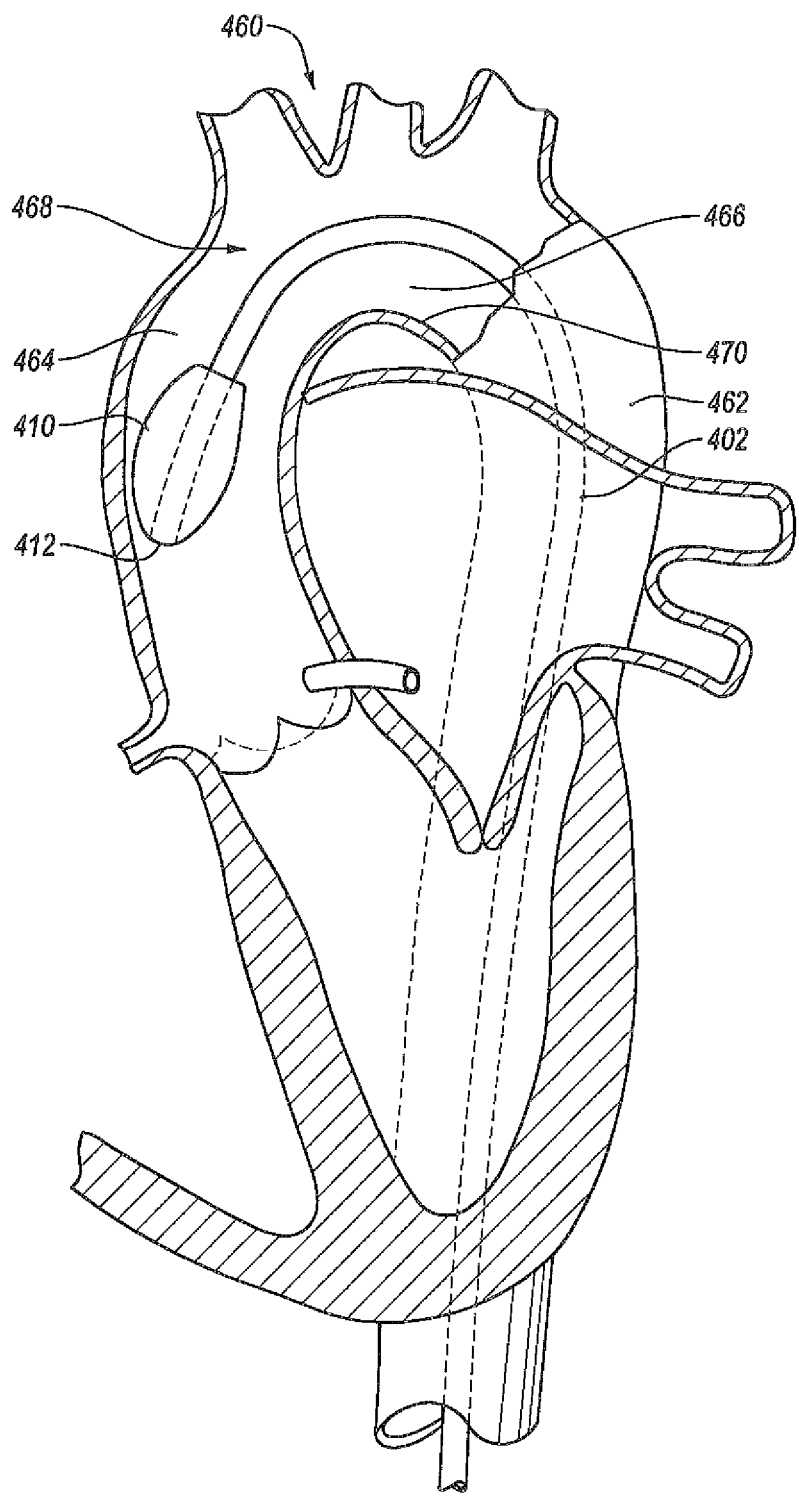
FIGS. 5A-5C are partial cross-sectional views of the distal end of an antegrade cardioplegia delivery catheter used to occlude a portion of the ascending aorta.

More particularly, in FIG. 5A, a shaft 402 and expandable member 410 may be passed through the descending aorta 462, around the aortic arch 466, and into the ascending aorta 464. During such movement, the expandable member 410 may be in a deflated or otherwise contracted state. In order to facilitate placement of the expandable member 410 and a distal tip 412 within the ascending aorta 464, the shaft 402 may be flexible. In particular, the shaft 402 may bend to generally correspond to a curve of the aortic arch 466. For instance, the aortic arch 466 may have an upper profile 468 and a lower profile 470. The shaft 402 may bend so as to generally have a curve that extends partially between the upper and lower profiles 468, 470 of the aortic arch 466.

Figure 5B:
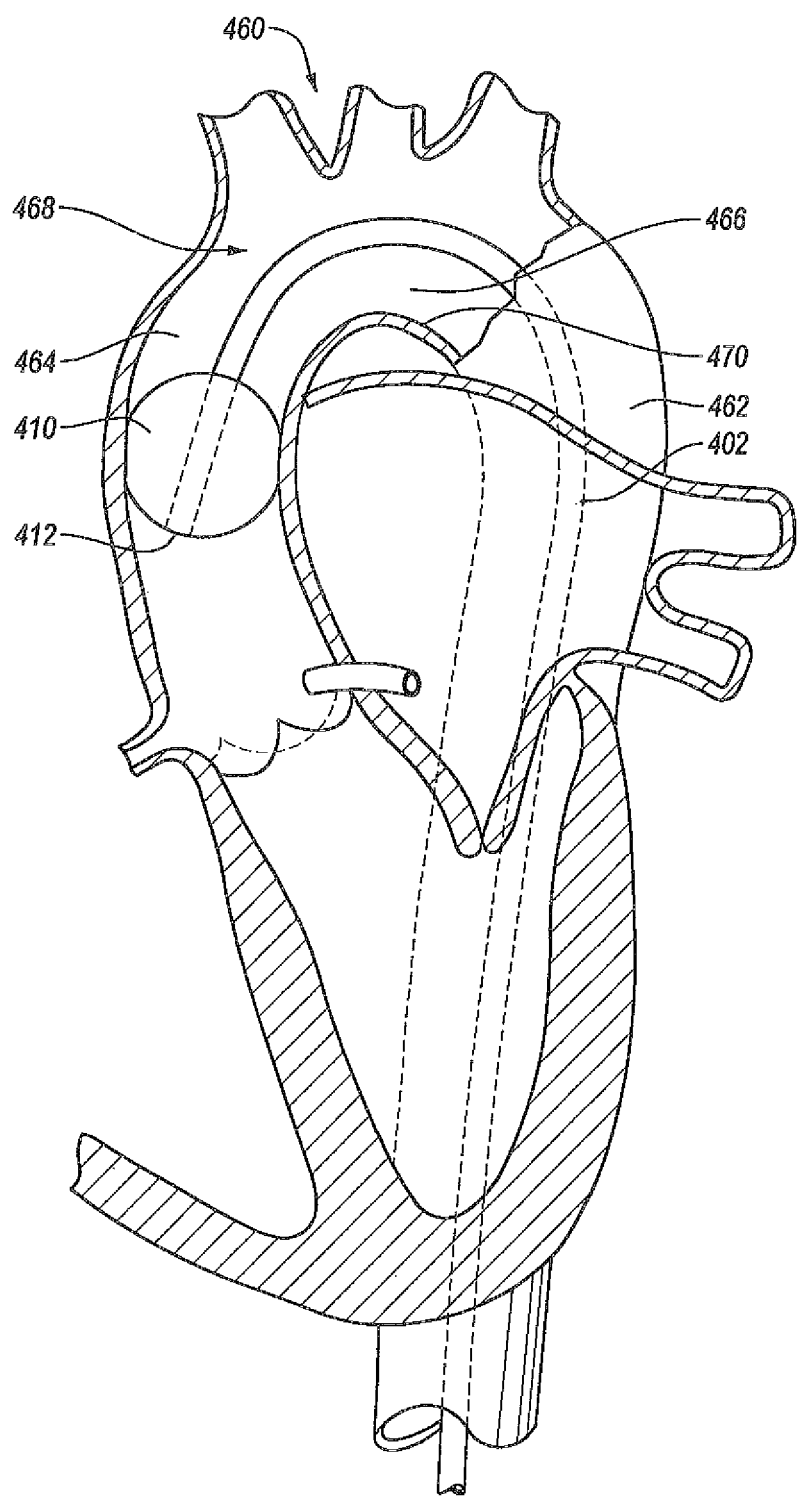

The expandable member 410 and distal tip 412 may be located using any suitable visualization technique. Once positioned in the desired location, the expandable member 410 may be expanded using any suitable manner, including those described herein. For instance, the expandable member 410 may be a balloon that is inflated to substantially occlude the ascending aorta 464. In FIG. 5B, for instance, the expandable member 410 has a generally spherical shape and the shaft 402 is generally concentric within the expandable member 410.

Inflation of the expandable member 410 on the distal end of the shaft 402 can fix the distal tip 412 of the shaft 402 within the ascending aorta 464 and isolate the left ventricle of the heart and the upstream portion of the ascending aorta 464 from the rest of the arterial system downstream from the expandable member 410. The passage of any debris or emboli, solid or gaseous, generated during a cardiovascular procedure to regions downstream from the site can be substantially prevented by the expanded expandable member 410. Fluid containing debris or emboli can be removed from the region between the aortic valve and the occluding expandable member 410 through an interior lumen of the shaft 402. A clear, compatible fluid (e.g., an aqueous based fluid such as saline) delivered through an interior lumen or the cardioplegic fluid may be maintained in the region wherein the cardiovascular procedure is to be performed to facilitate use of an angioscope or other imaging means that allows for direct observation. Such use of a delivery catheter may be particularly useful in the removal of an aortic heart valve and replacement thereof with a prosthetic heart valve which procedure is described in U.S. Pat. No. 5,738,652, which patent is hereby expressly incorporated herein by this reference, in its entirety.

The expandable member 410 may have forces applied thereto that cause the expandable member 410 to shift position. For instance, as cardioplegic fluid is expelled from the distal tip 412, the fluid flow may generally cause the expandable member 410 to move upward through the ascending aorta 464 and towards the aortic arch 466. Other forces may also be applied, for instance, a decrease in perfusion pressure may also cause the expandable member 410 to move towards the aortic arch 466. In contrast, the systemic blood pressure, increases in root vent suction, or increases in perfusion pressure may tend to cause the expandable member 410 to move further into the ascending aorta 464 and away from the aortic arch 460.

Migration of the expandable member 410 may be particularly likely where slack is present in the shaft 402. Accordingly, to minimize migration of the expandable member 410, a surgeon may pull on the delivery catheter so as to at least partially retract the shaft 402. For instance, a surgeon may pull two to three inches of slack out of the shaft 302. As a result, the expandable member 410 may move towards the aortic arch 466. In retracting the expandable member 410, external surfaces of the expandable member 410 may also more fully engage the upper and lower portions of the ascending aorta 464, thereby more securely positioning the expandable member 410 as it occludes the aorta.

Figure 5C:
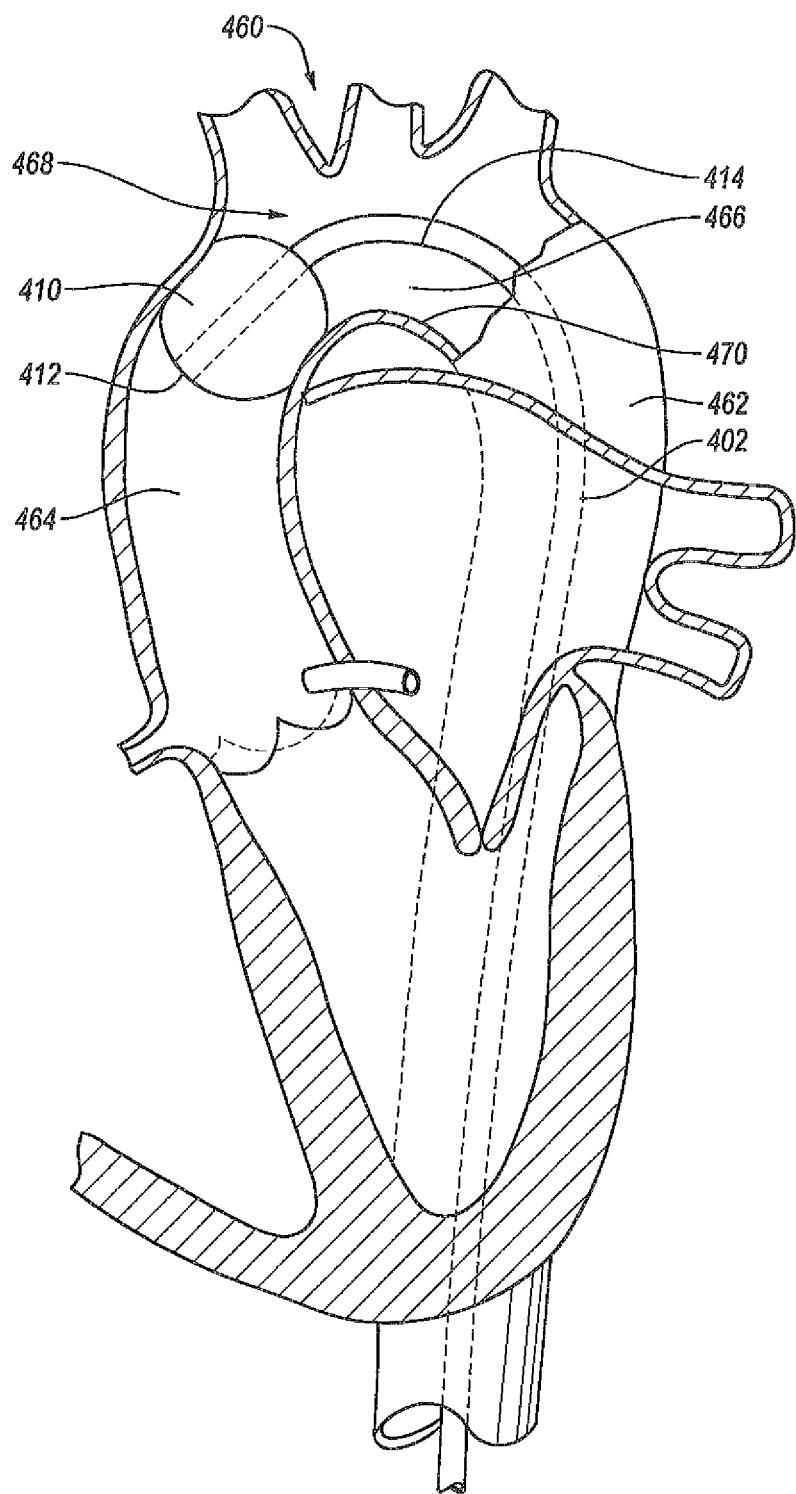

As shown in FIG. 5C, the shaft 402 may have a curved profile 414 that generally corresponds to a portion of the aortic arch 466. In this embodiment, for instance, the curved profile 414 allows the shaft 402 to curve around the aortic arch 466 generally between the upper profile 468 and lower profile 470 of the aortic arch 466. The shaft 402 may be generally mid-way between the upper and lower profiles 468, 470, although such is not necessary. For instance, the shaft 402 may be generally flexible such that the profile 414 adapts to a suitable geometry that allows the expandable member 410 to remain at the illustrated occluding position.

When the slack is pulled from the shaft 402, such that the expandable member 410 is secured within the ascending aorta 464, the distal tip 412 of the shaft 402 may migrate and change orientation within the ascending aorta 464. More particularly, in the illustrated embodiment, the distal tip 412 may be positioned at an angle relative to the ascending aorta 464. As noted herein, cardioplegic fluid may, in some instances, be perfused to the ascending aorta 464 through the distal tip 412. Where the distal tip 412 is angled, pressurized fluid may exit the distal tip 412 and be directed at the upper wall of the ascending aorta 464. In some cases, such delivery may be undesirable as the pressurized fluid may cause trauma or other damage to the interior wall of the ascending aorta 464. Generally speaking, the shape of the expandable member 410, curvature of the shaft 402, and location of the shaft 402 within the expandable member 410 may each contribute to the orientation of the distal tip 412.

Figure 6B:
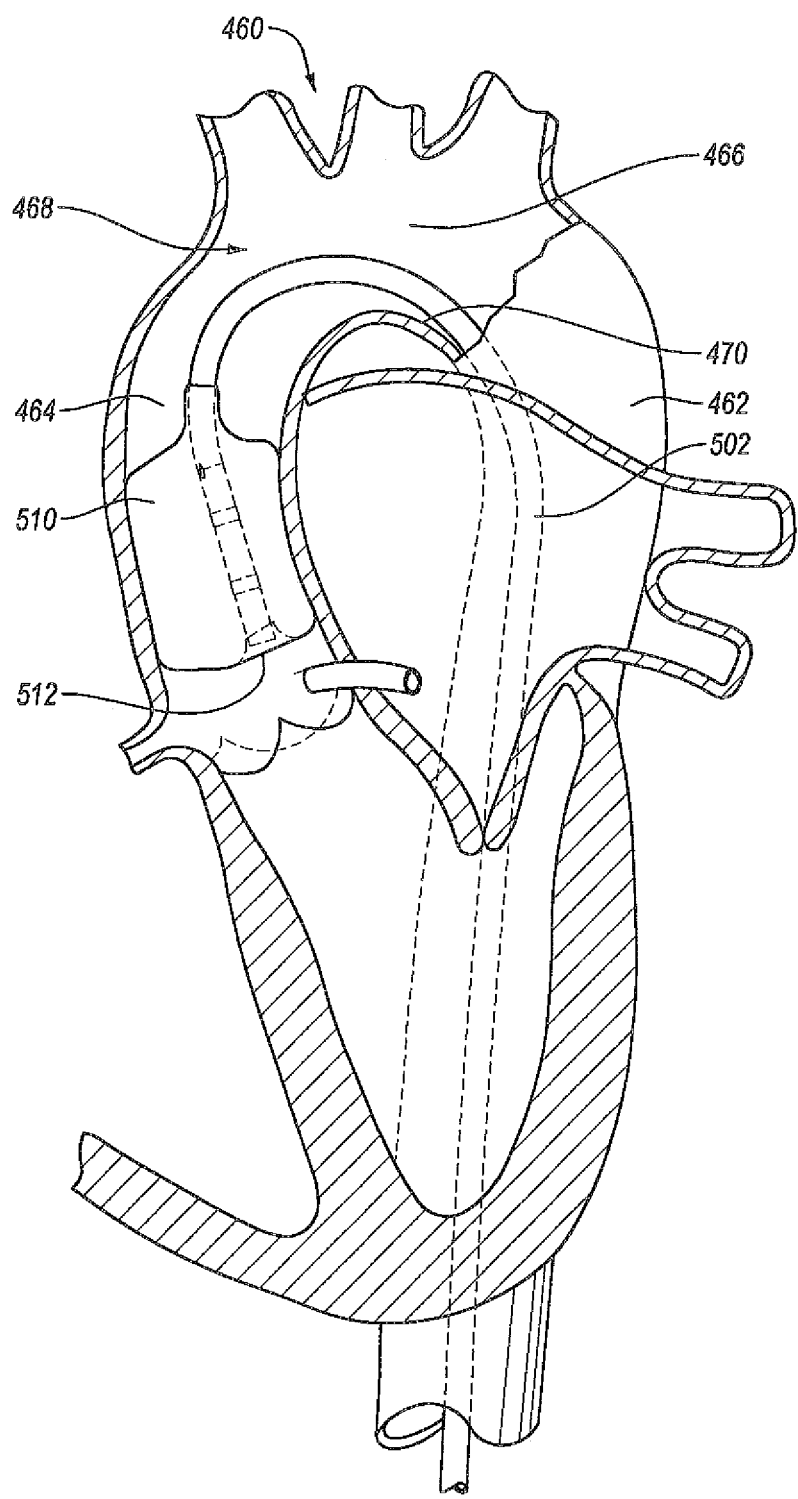
Figure 6C:
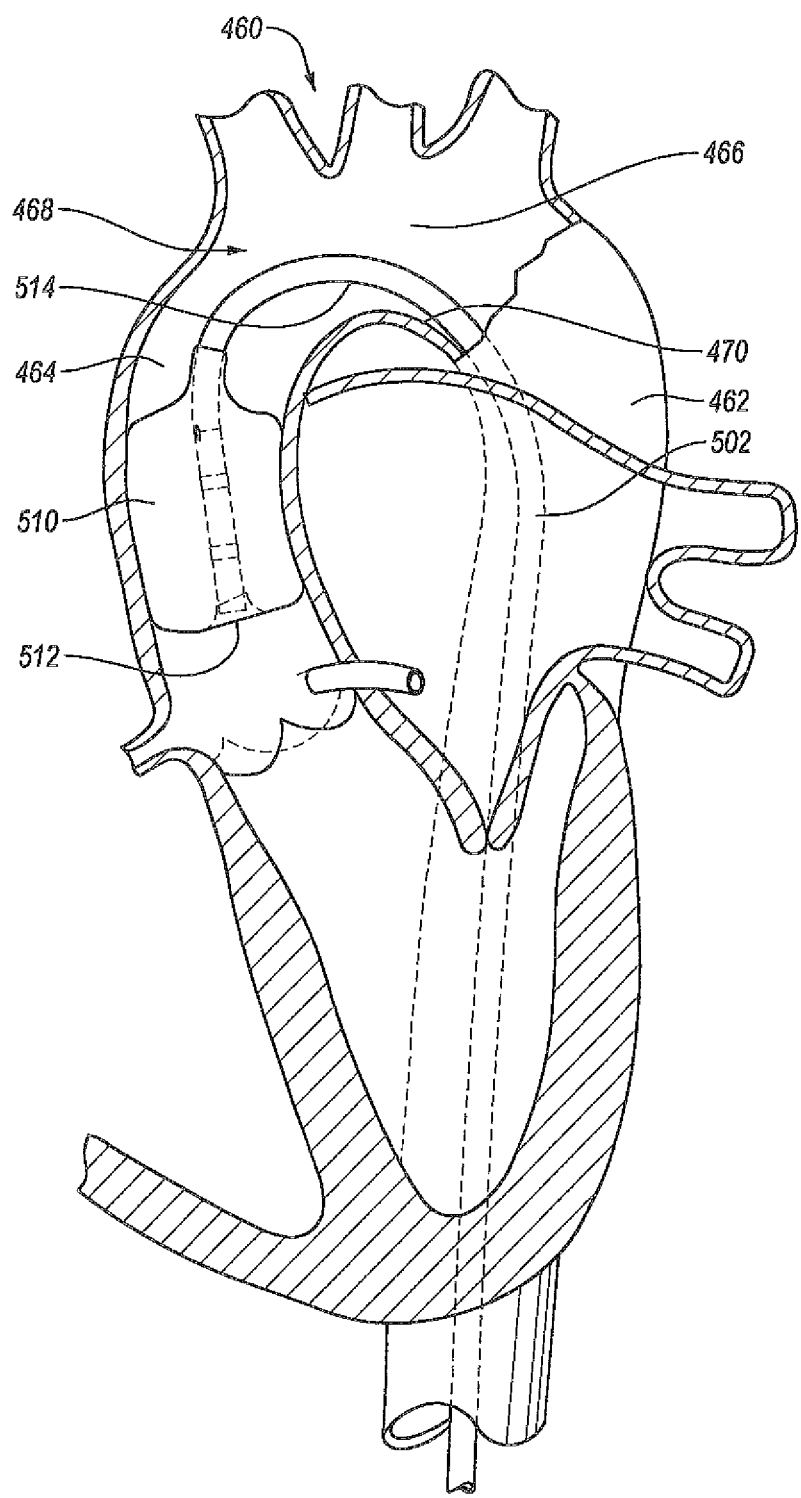

FIGS. 6A-6C illustrate an alternative embodiment of a delivery catheter that may be used to occlude the aorta 460 and deliver cardioplegic fluid to the ascending aorta 464. In particular, FIG. 6A illustrates an embodiment similar to that shown in FIG. 5A. More particularly, a shaft 502 is connected to an expandable member 510 and passed through the descending aorta 462, around the aortic arch 466, and into the ascending aorta 464 while the expandable member 510 is in a deflated or other contracted state.

Once within the ascending aorta 464, the expandable member 510 may be inflated or otherwise expanded as shown in FIG. 6B. In the illustrated embodiment, the expandable member 510 has an elongated construction. The particular shape of the expandable member 510 may vary. For instance, the expandable member 510 may be hexagonal, trapezoidal, cylindrical, barrel-shaped, or have another suitable configuration.

As further shown in the illustrated embodiment, the shaft 502 may be eccentrically positioned relative to the expandable member 510. As a result, an upper portion of the expandable member 510 may be larger in at least one dimension that a lower portion of the expandable member 510. The upper portion of the expandable member 510 may be adapted to engage the upper surface 468 of the aorta 460, while the lower portion of the expandable member 510 may be adapted to engage the lower, or bottom surface 470 of the aorta 460. By engaging the upper and lower surfaces 568, 470 of the aorta 460, the expandable member 510 may substantially occlude the aorta 460.

In some embodiments, the expandable member 510 may also be retracted so as to secure the expandable member 510 in a position that reduces migration of the expandable member 510. As shown in FIG. 6C, the shaft 502 may be at least partially retracted so as to move the expandable member 510 within the ascending aorta 464 and towards the aortic arch 466. In some embodiments, retracting the shaft 502 may require only a minor amount of slack to be removed from the shaft 502. For instance, in the illustrated embodiment, the shaft 502 has a curved profile 514 generally corresponding to the contour of the aortic arch 466. In at least one embodiment, the curved profile 514 is specifically configured to generally correspond to the size and contour of the lower or bottom surface 470 of the aortic arch 466. Consequently, as the shaft 502 is inserted into the aorta 460, the shaft 502 tracks along the bottom surface 470; this can minimize the travel distance of the shaft 502. With reduced travel distance, there may be less slack in the shaft 502. Moreover, as the shaft 502 can mirror the contour of the bottom surface 470, retraction of the shaft 502 also causes the shaft 502 to track along the bottom surface 470 of the aorta 460. The retraction distance, and thus the amount of slack that is pulled out, may thus be reduced. For instance, less than two inches, and potentially less than one inch of slack may be removed in order to securely position the expandable member 510 in a desired position. For instance, in some embodiments, about three centimeters of slack may be removed from the shaft 502.

As further shown in FIG. 6C, once the slack has been pulled out and the expandable member 510 secured in an occluding position within the ascending aorta 464, the distal tip 512 may remain positioned within the ascending aorta 464. In this embodiment, the distal tip 512 is generally oriented to be about parallel with the ascending aorta 464. Consequently, in embodiments in which cardioplegic fluid is passed out of the distal tip 512 and perfused to the ascending aorta 464, the cardioplegic fluid may be directed along the pathway of the ascending aorta 464, rather than into a sidewall of the ascending aorta 464. The substantially parallel alignment of the distal tip 512 may thus reduce a risk of trauma to the ascending aorta 464 during a surgical procedure.

The positioning of the distal tip 412 in a parallel or substantially parallel position within the ascending aorta 464 may result from a combination of one or more factors, including shape of the expandable member 510, eccentric positioning of the shaft 502 relative to the expandable member 510, the curve profile 514 of the shaft 502, material properties of the shaft 502, or other factors, or any combination of the foregoing. For instance, in one embodiment, the expandable member 510, eccentric position of the shaft 502, and material properties of the shaft 502 may be similar to those described above with respect to delivery catheter 300 of FIGS. 4A-4D. The curve profile 514 of the shaft 502 may also be similar to those previously described. By way of illustration, in some embodiments, the shaft 502 may include a core (not shown) that is formed at least partially of a memory material that has a pre-determined and manufactured curve profile. Such profile may vary as desired based on the patient, size of the aorta, or other factors. In one example embodiment, the curve profile 514 is configured to have a radius of curvature of between about ten and about twenty five millimeters. More particularly, in some embodiments, the radius of curvature at the curve profile 514 of the shaft 502 may be between about fifteen and about twenty one millimeters. In a still more particular embodiment, the radius of curvature at the curve profile 514 of the shaft 502 may be between about seventeen and about nineteen millimeters.

Figure 7:
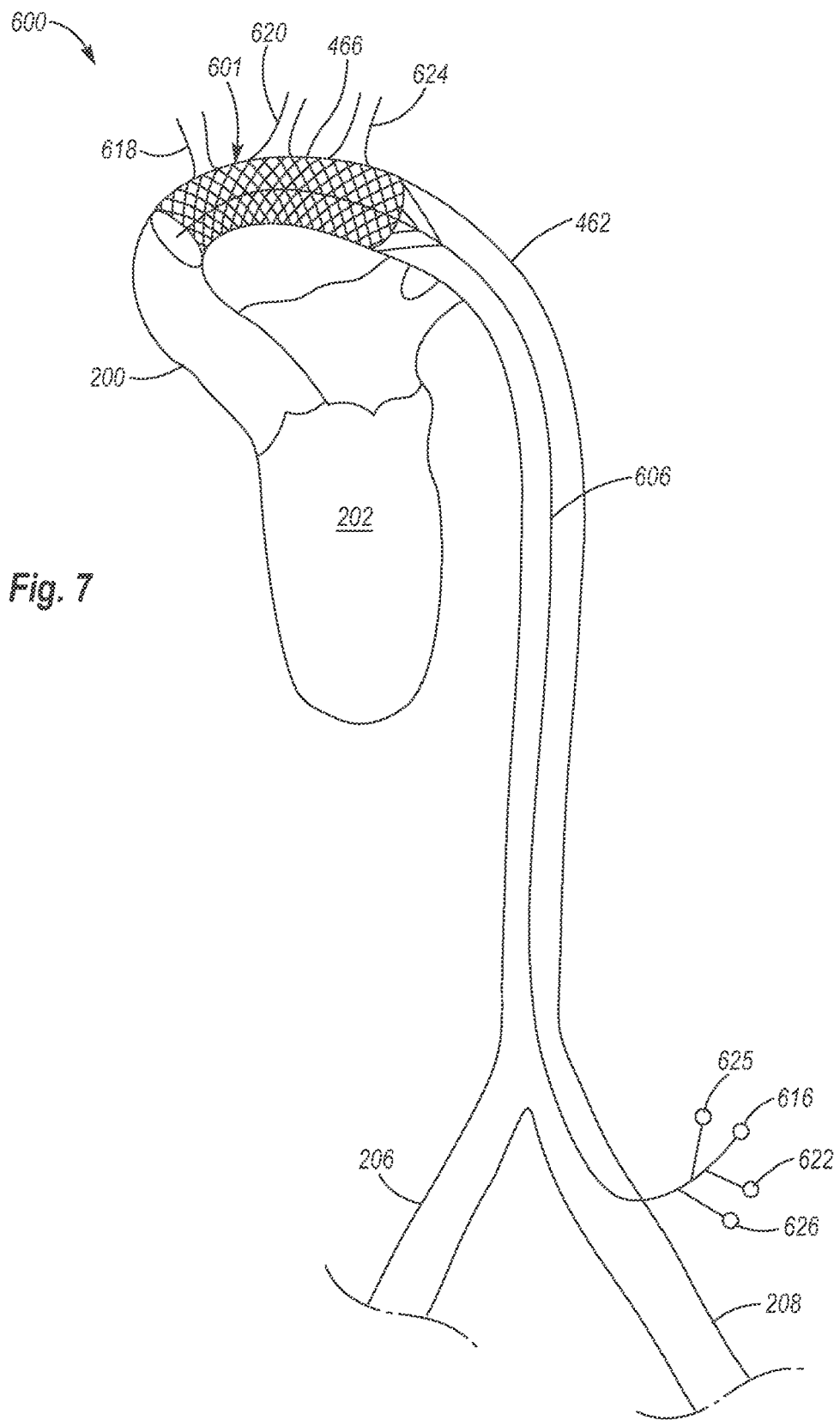
FIG. 7 schematically illustrates an aortic occlusion device located in the aortic arch.

Referring now to FIG. 7, there is shown another exemplary embodiment of an aortic occlusion device 600 for occluding the aorta, such as during cardiopulmonary bypass, as well as a schematic illustration of a cardiac access system similar to the system 100 of FIG. 1. The aortic occlusion device can be positioned in the aortic arch 466 and can be configured to occlude the ascending aorta 200 such that retrograde blood flow provided by a cardiopulmonary bypass system, such as the system of FIG. 1, is substantially prevented from entering the left ventricle 202 of the heart during cardiopulmonary bypass. In this manner, the device 600 can help to prevent blood from entering the heart after cardioplegia is induced without damaging the tissue of the aorta. The device 600 can also be configured to act as a filter for blood entering the device through the descending aorta 462 during retrograde circulation induced attendant to cardiopulmonary bypass. As such, the device 600 can be configured to filter or remove emboli (e.g., plaque, etc.) from blood passing through the device. As shown in FIG. 7, the device 600 can be positioned in the aortic arch 466 such that it is substantially adjacent to, or covering, the ostia of the brachiocephalic artery 618, the carotid artery 620, and/or the subclavian artery 624. In this manner, the device 600 can filter or remove emboli from blood entering the arteries 618, 620, 624 during cardiopulmonary bypass.

Figure 8A:
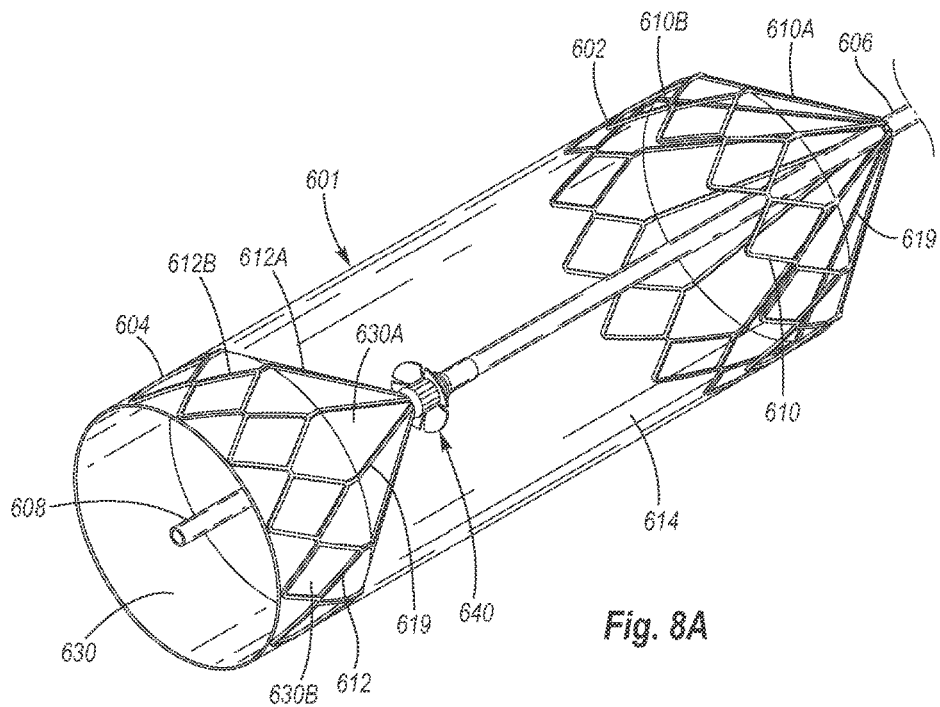
FIG. 8A is a perspective view of an aortic occlusion device.
Figure 8B:
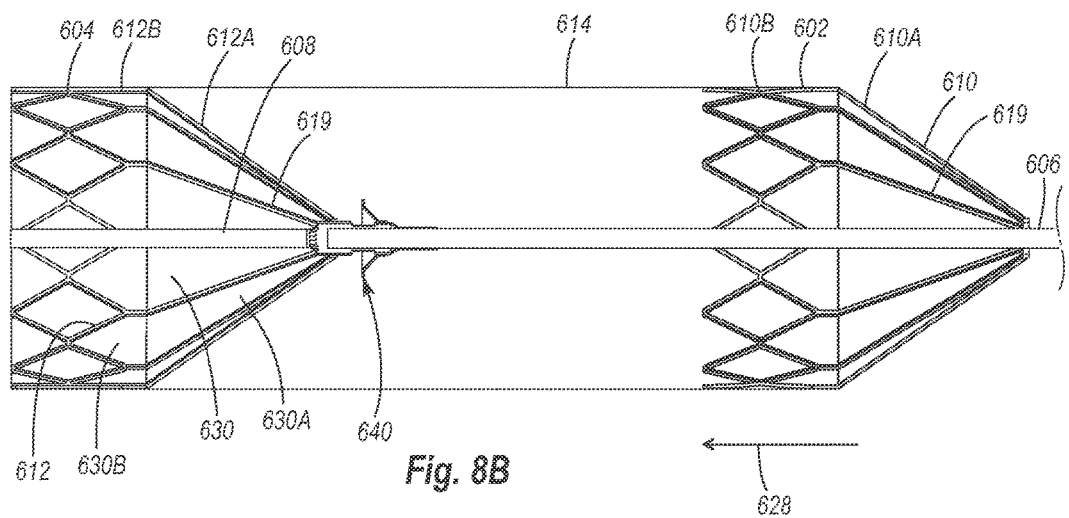
FIG. 8B is a cross-sectional view of the aortic occlusion device of FIG. 8A.

As shown in FIGS. 8A-8B, the aortic occlusion device 600 can comprise a generally tubular body 601 having a proximal end portion 602, a distal end portion 604, and a porous covering or membrane 614 extending between the proximal and distal end portions 602, 604. The porous covering 614 can be configured to allow blood to flow across the covering 614 to perfuse the brain and other important structures served by the arteries 618, 620, 624. The covering 614 can also filter or remove emboli from the blood flow, and particularly emboli of a size likely to cause an embolic stroke of clinical significance. In some embodiments, the porous covering 614 can have pores that range in size from about 50 µm to about 200 µm. In some embodiments, the pores can be about 50 µm or less.

The covering 614 can be made of any of a variety of biocompatible materials, including, without limitation, polyurethane, polyethylene terephthalate (PET), polytetrafluoroethylene (PTFE), polypropylene, polyacrylamide, silicone, polymethylmethacrolate, GoreTex®, or ePTFE with a high internodal distance. In some embodiments, the wall thickness of the porous covering 614 can be from about 0.0001-0.005 inches, or from about 0.0005-0.0015 inches. The wall thickness can vary depending on the material selected. The porous covering 614 can be either elastic or non-elastic. The porous covering 614 can also have either uniform or non-uniform pore sizes, and areal distribution patterns. In some embodiments, the porous covering 614 can be filled or coated with a radiopaque material, and may be woven, extruded or otherwise film-formed, or air-laid. In some embodiments, the porous covering 614 can be substantially similar to the membrane described in U.S. Patent Application Publication 2010/0179585, which is incorporated herein by reference. Referring to the figures generally, the porous covering 614, and the porous coverings of the various other embodiments described herein, are primarily shown transparent for purposes of illustration.

The proximal and distal end portions 602, 604 can comprise respective substantially rigid zones for anchoring the device within the aortic arch 466. For example, the proximal and distal end portions 602, 604 can comprise radially expandable and collapsible frames or stents 610, 612, respectively. The frames 610, 612 can have a lattice-like configuration and/or can be formed from a plurality of angled struts 619 allowing radial compression and expansion of the frames. In this manner, the frames 610, 612 can expand from a collapsed delivery state to contact the inner surfaces of the aortic arch, thereby anchoring the device 600. In some embodiments, the frames 610, 612 can be radially self-expandable when released from within a delivery catheter or other type of radial restrictor. In other embodiments, the frames 610, 612 can be mechanically expanded using controls located at the proximal portion of the cardiac access system. In some embodiments, the device 600 can include one or more inflatable balloons positioned within one or both the frames 610, 612 for radial expansion of the frames. In some embodiments, the frames 610, 612 can comprise substantially conical portions 610A, 612A, respectively, and substantially cylindrical portions 610B, 612B, as shown in FIGS. 8A-8B. In the embodiment of FIGS. 8A-8B, the frames are oriented such that the conical portions 610A, 612A are positioned proximal to the respective cylindrical portions 610B, 612B, and taper in the proximal direction. However, the frames 610, 612 may be oriented in any suitable orientation. Additionally, although the porous covering 614 is shown disposed around the cylindrical portions 610B, 612B of the respective frames 610, 612, the porous covering 614 can also extend to cover the conical portion 610A of the proximal frame 610, as desired.

The struts 619 of respective frames 610, 612 can be made of any of various suitable plastically-expandable materials (e.g., stainless steel, etc.) or self-expanding materials (e.g., Nitinol) as known in the art. When constructed of a plastically-expandable material, the frames 610, 612 (and thus the device 600) can be crimped to a radially compressed or collapsed state on a delivery catheter and then expanded inside a patient by one or more inflatable balloons positioned within the frames, or an equivalent expansion mechanism. When constructed of a self-expandable material, the frames 610, 612 (and thus the device 600) can be crimped to a radially collapsed state and restrained in the collapsed state by insertion into a sheath or equivalent mechanism of a delivery catheter, such as the delivery catheter 102 of FIG. 1. Once inside the body, the device can be advanced from the delivery sheath, which allows the frames 610, 612 to self-expand to their functional size and engage within the aortic arch.

Suitable plastically-expandable materials that can be used to form the struts 619 of the frames 610, 612 include, without limitation, stainless steel, a nickel based alloy (e.g., a nickel-cobalt-chromium alloy), polymers, or combinations thereof. In particular embodiments, frames 610, 612 can be made of a nickel-cobalt-chromium-molybdenum alloy, such as MP35N™ (tradename of SPS Technologies), which is equivalent to UNS R30035 (covered by ASTM F562-02). MP35N™/UNS R30035 comprises 35% nickel, 35% cobalt, 20% chromium, and 10% molybdenum, by weight.

As shown in FIGS. 8A-8B, the distal end portion 604 can further comprise a liner 630 configured to block the flow of blood through the distal end portion of the device. The liner 630 can include a substantially conical portion 630A and a substantially cylindrical portion 630B, corresponding to conical and cylindrical portions 612A, 612B of the frame 612. The liner 630 can be positioned within the frame 612, outside of the frame 612, and/or the frame 612 can be at least partially embedded in the liner 630. In some embodiments, the liner 630 can be fabricated from a flexible polymeric material, and can be mounted or attached to the interior of the frame 612 by, for example, adhesives, sutures, etc. In this manner, the liner 630 can be configured to prevent blood from flowing out through the distal frame 612 and into the heart during cardiopulmonary bypass.

The device 600 can also comprise a first catheter or shaft 606 and a second catheter or shaft 608. As shown in FIGS. 8A-8D, the first catheter 606 can extend from adjacent a proximal end of the distal end portion 604, through the proximal end portion 602, and out of the body, such as through the descending aorta 462 and the femoral artery 208 (see, e.g., FIG. 7). In this manner, retrograde blood flow through the descending aorta (and/or other associated arteries, such as the femoral artery) from the cardiopulmonary bypass machine can pass outside of the first catheter 606. This flow arrangement can be applicable to any of the embodiments described herein.

Referring again to FIG. 7, the first catheter 606 can comprise various attachments at a proximal end, such as a main port 622, a first arm 616 for manipulating the device in the aorta, a bypass line 626, and an aortic pressure sensor 625, and can comprise one or more internal lumens. In some embodiments, the first catheter 606 can serve as a central guide member around which at least a portion of the device 600 can be radially collapsed before insertion into the body. In some embodiments, the second catheter 608 can extend from adjacent the distal end of the first catheter 606, through the distal end portion 604 of the device 600.

Figure 8C:
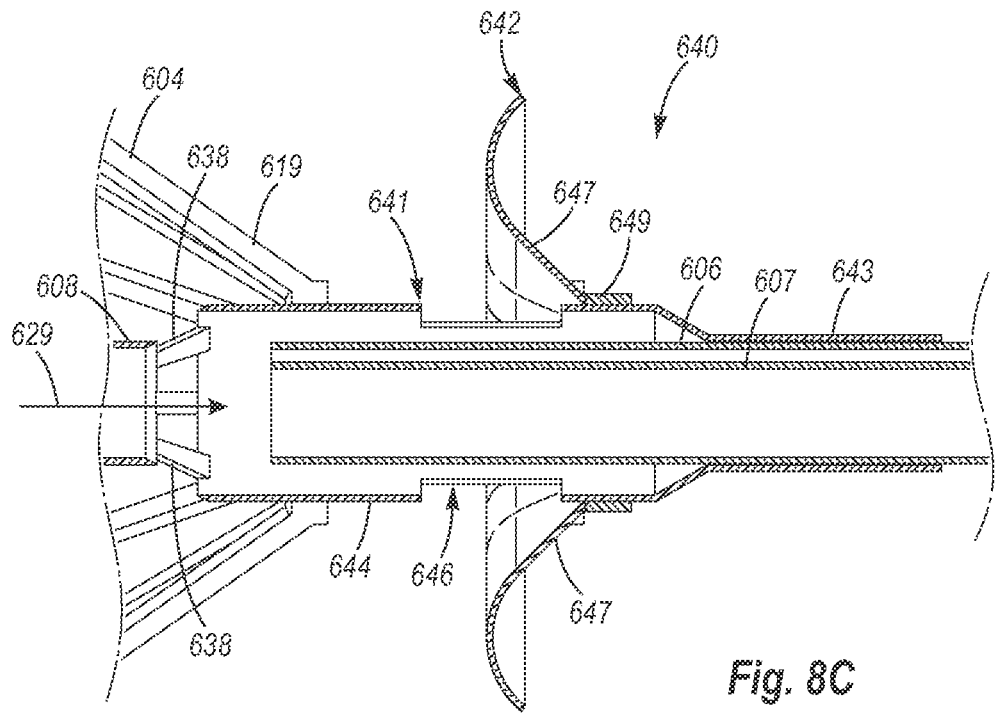
FIGS. 8C-8D are cross-sectional views of a valve of the embodiment of FIG. 8A.
Figure 8D:
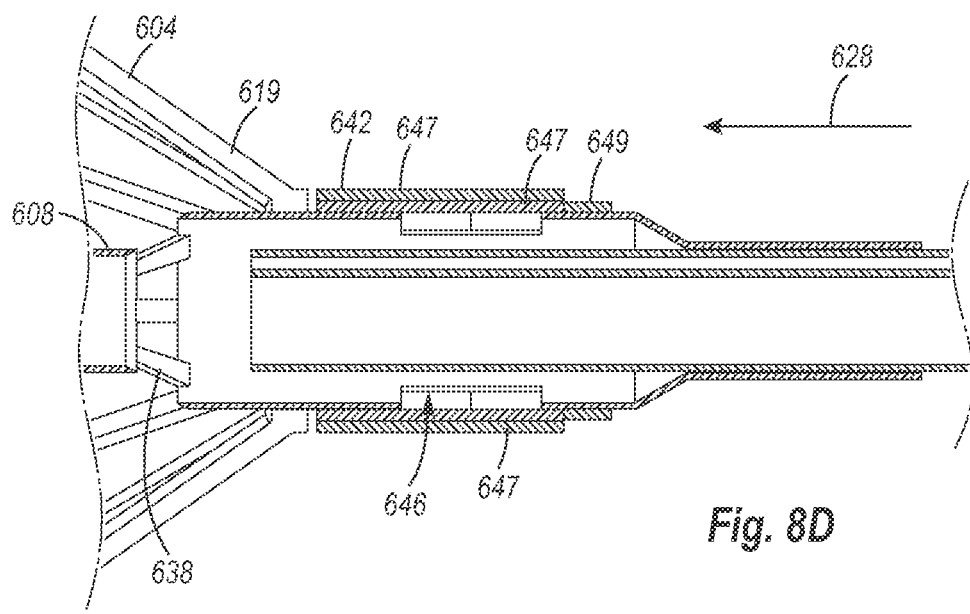

The device 600 can also include a one-way valve, such as the exemplary valve 640, as shown in FIGS. 8A-8D. Referring to FIGS. 8C and 8D, the valve 640 can comprise a housing 641 having a proximal end portion 643 and a distal end portion 644. The distal end portion 644 of the housing 641 can define one or more radial openings 646. The proximal end portion 643 of the housing can be positioned securely around the first catheter 606 such that the housing 641 is retained on the first catheter 606. In the embodiment shown, the first catheter 606 terminates inside the distal end portion 644 of the housing 640. Alternatively, the first catheter 606 can terminate at any suitable location proximate to or inside the housing 640. A proximal end of the second catheter 608 can be rigidly connected to the distal end portion 644 of the housing 640 by struts 638, as shown in FIGS. 8C and 8D.

The radial openings 646 can be covered by a flexible sealing member 642 that is movable between an open position (FIG. 8C) and a closed position (FIG. 8D). In some embodiments, the sealing member 642 can have a plurality of flexible leaflets 647 mounted to an annular base 649, as shown in FIGS. 9A-9D. The leaflets 647 can be configured such that when the sealing member 642 is in the open position the leaflets 647 flare radially outwardly, allowing blood to flow out of the openings 646. Conversely, when the sealing member 642 is in the closed position, the leaflets 647 overlap to seal the openings 646, as shown in FIGS. 9B and 9D. In this manner, during cardioplegia, blood flowing into the device 600 in the retrograde direction indicated by arrow 628 can cause the leaflets 647 of the sealing member 642 to move into the closed position (FIG. 8D), thereby preventing blood from flowing into the distal end portion 604 of the device 600 and into the heart. This, in turn, can promote the flow of blood radially outwardly through the porous covering 614 and into the arteries 618, 620, and 624. When cardioplegia is reversed, such as at the end of the cardiopulmonary bypass procedure, the relatively high pressure in the ascending aorta caused by the beating heart can cause blood to flow in the antegrade direction indicated by arrow 629, into the distal end portion 604, between the struts 638, and into the housing 641. This can cause the leaflets 647 of the sealing member 642 to open radially outwardly to uncover the openings 646 (FIG. 8C), thereby restoring antegrade circulation through the vasculature.

Figure 10A:
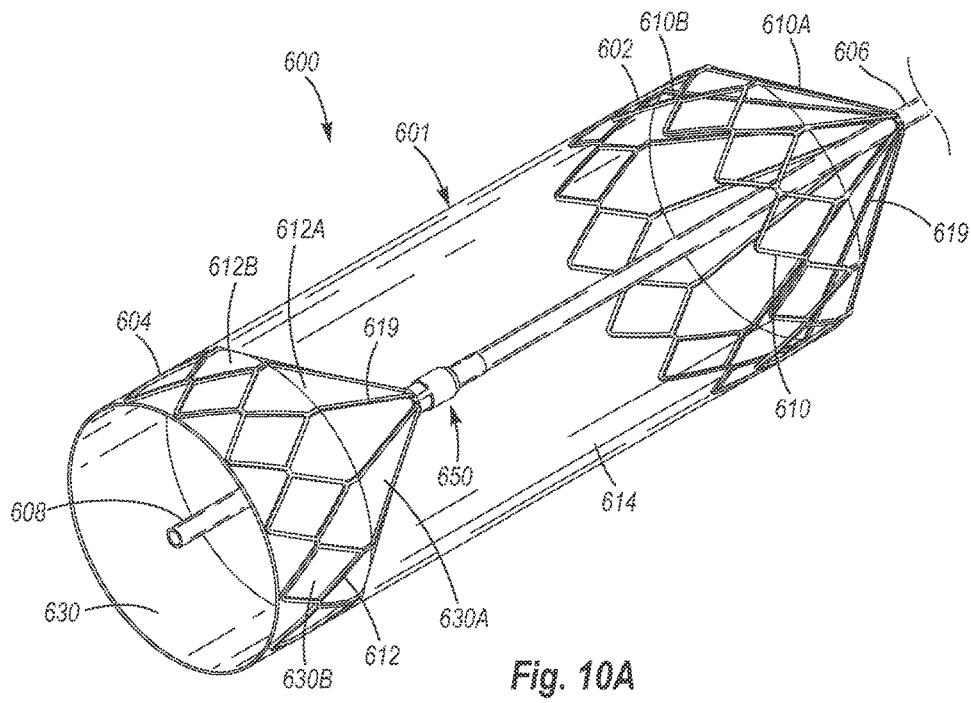
FIG. 10A is a perspective view of the aortic occlusion device of FIG. 8A including an alternative embodiment of a valve.
Figure 10B:
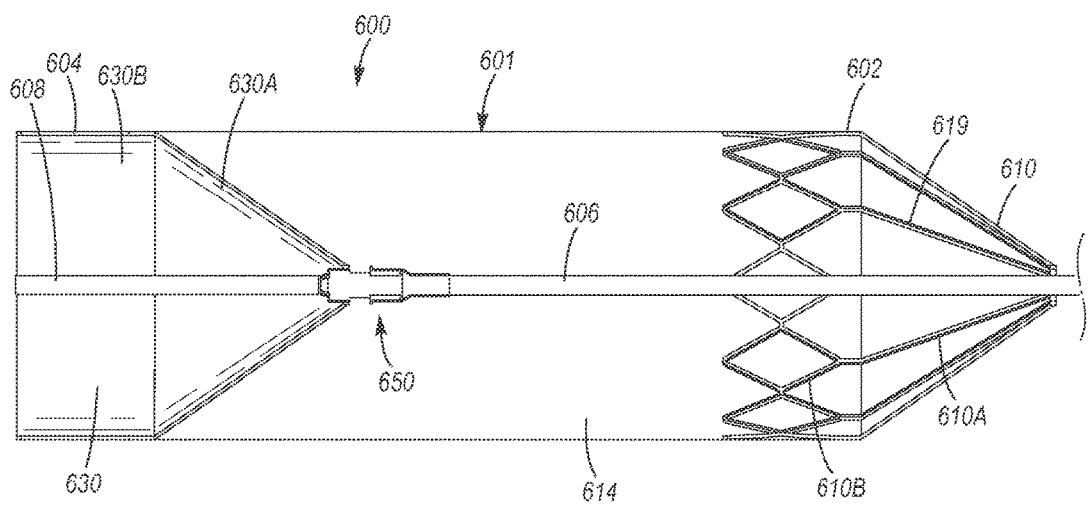
FIG. 10B is a cross-sectional view of the aortic occlusion device of FIG. 10A.
Figure 11A:
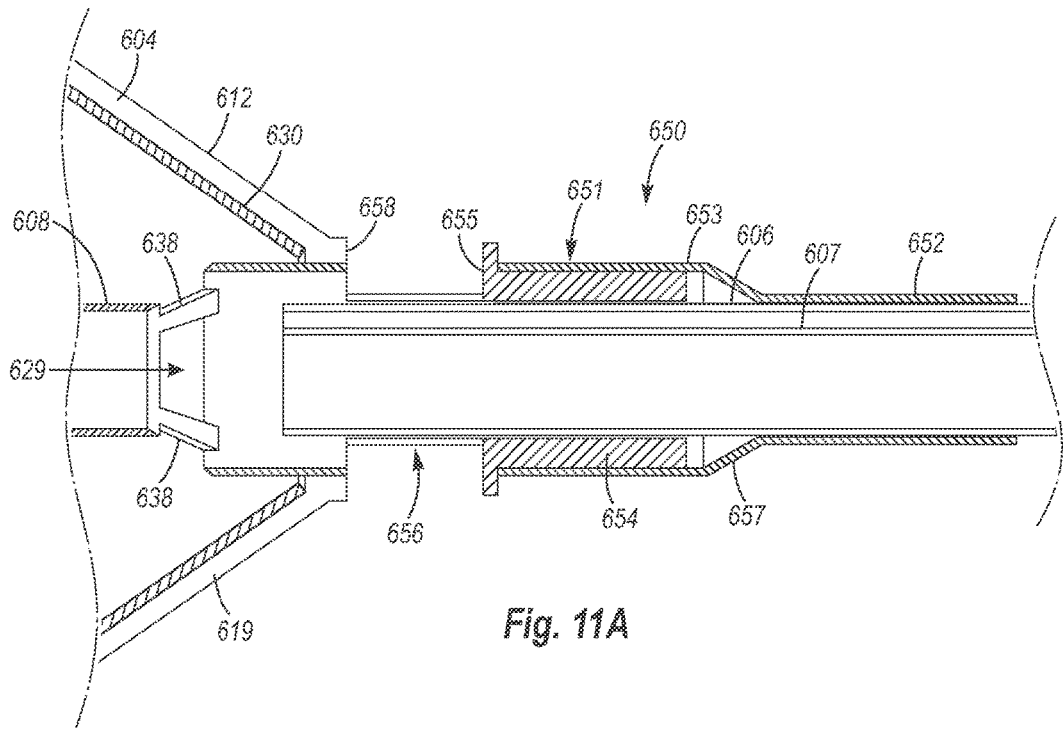
FIGS. 11A-11B are cross-sectional views of the valve of FIG. 10A.
Figure 11B:
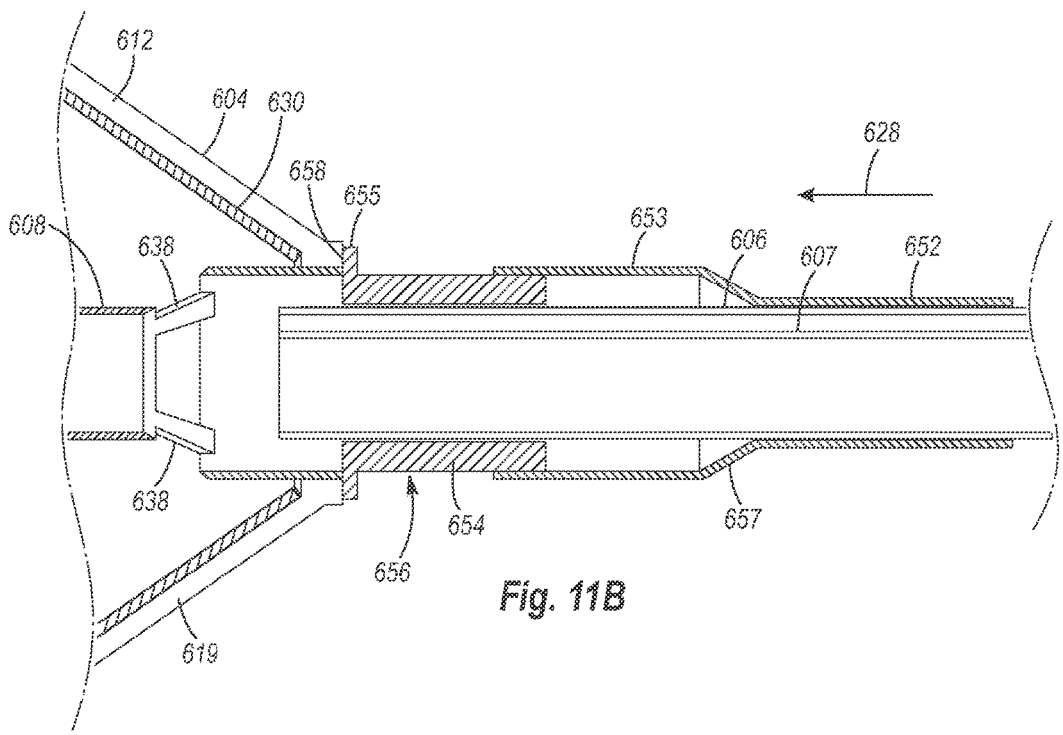

Referring now to FIGS. 10A-10B and 11A-11D, there is shown another embodiment of a valve 650 for the device 600. As best illustrated in FIGS. 11A and 11B, the valve 650 can be a one-way valve, and can comprise a housing 651 having a proximal end portion 652 and a distal end portion 653, similar to the housing of the valve 640. The distal end portion 653 can define one or more radial openings 656, and the proximal end portion 652 can be secured around the first catheter 606 such that the housing 651 is retained on the first catheter. In the embodiment shown, the first catheter 606 terminates inside the distal end portion 653 of the housing 650. Alternatively, the first catheter 606 can terminate at any suitable location proximate to or inside the housing 650. A proximal end of the second catheter 608 can be rigidly connected to the distal end portion 653 of the housing by the struts 638, as shown in FIGS. 11A and 11B.

Figure 11C:
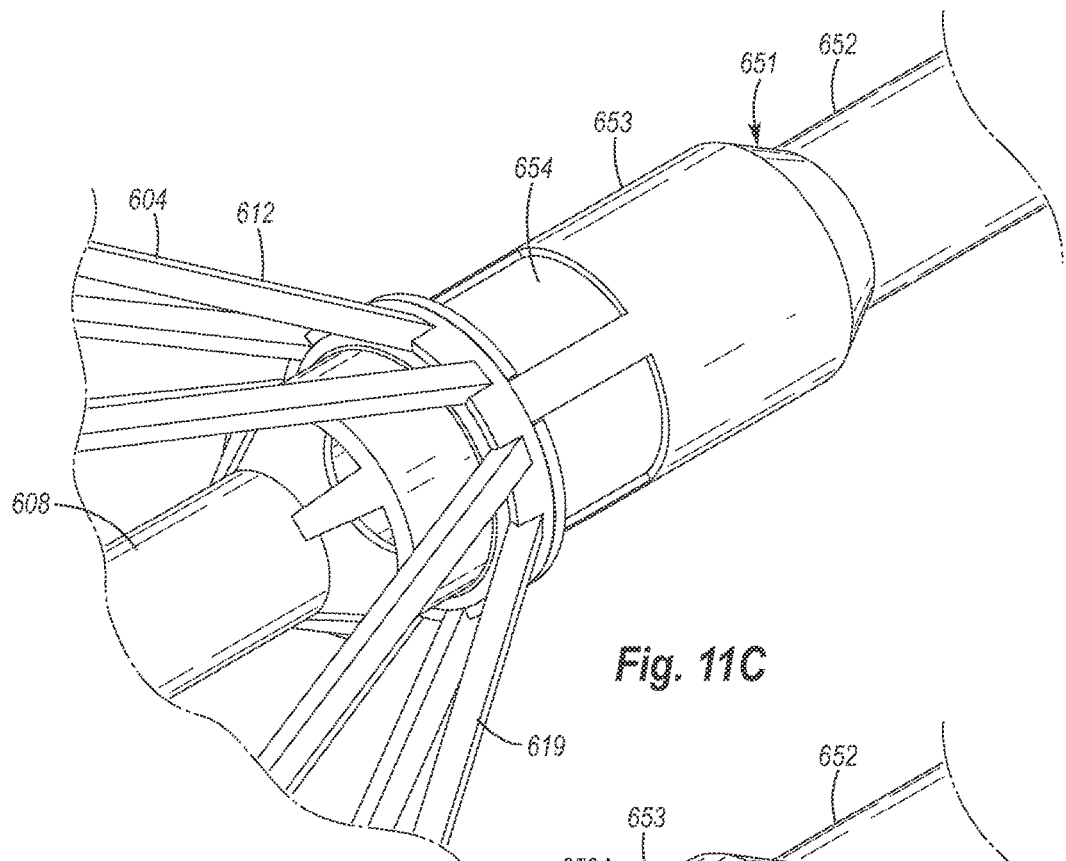
FIGS. 11C-11D are perspective views of the valve of FIG. 10A.
Figure 11D:
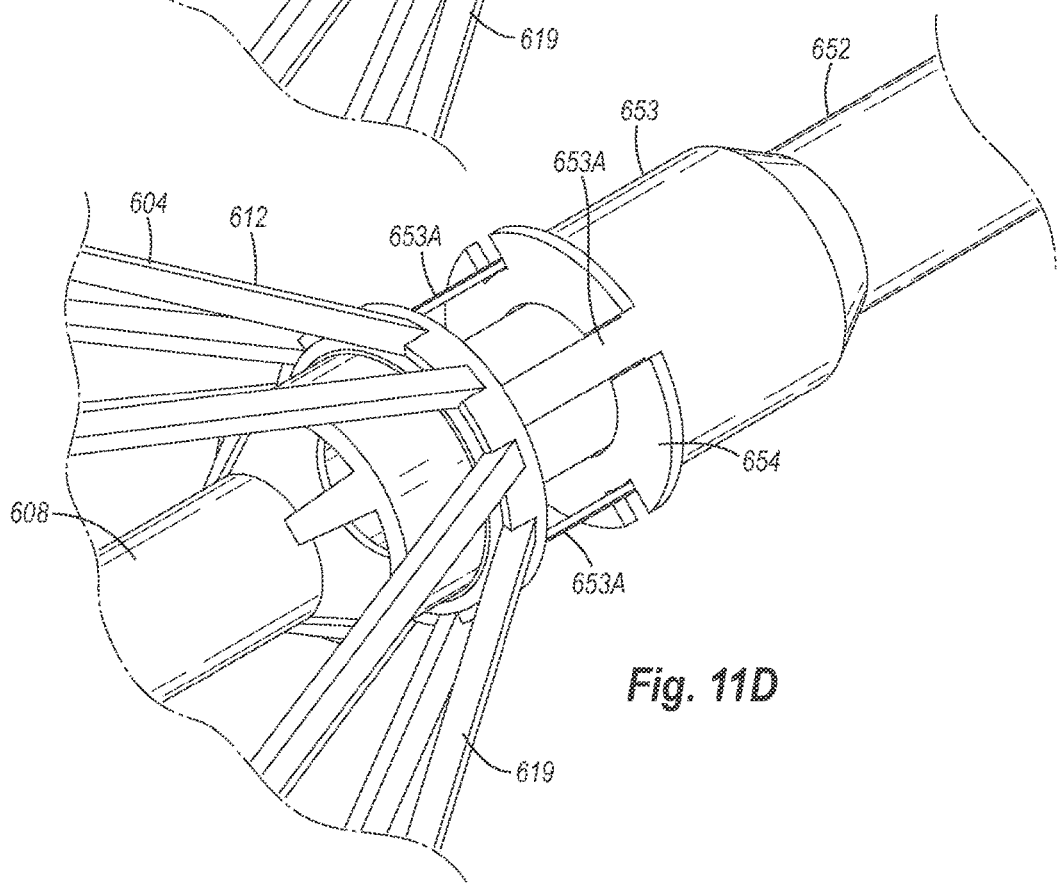

The valve 650 can comprise a sealing member 654 which can be slidably disposed around the distal end of the first catheter 606 and axially movable between an open position (FIGS. 10A, 11A, and 11D) and a closed position (FIGS. 10B, 11B, and 11C). For purposes of illustration, the distal end portion 604 is shown without the liner 630 in FIGS. 11C and 11D. In some embodiments, the sealing member 654 can comprise a radially extending flange 655 configured to form a seal with a proximally-facing surface 658 of the frame 612 when the sealing member 654 is in the closed position. The sealing member 654 can be configured such that pressure exerted against the radially extending flange 655 by blood entering the device in the retrograde direction indicated by arrow 628 (see, e.g., FIGS. 10B and 11B) during cardiopulmonary bypass causes the sealing member 654 to move distally into the closed position, as shown in FIG. 11B, thereby preventing retrograde blood flow into the distal end portion 604 of the device and into the heart. When cardioplegia is reversed, such as at the end of the cardiopulmonary bypass procedure, the relatively high pressure in the ascending aorta caused by the beating heart can cause blood to flow in the antegrade direction indicated by arrow 629 and into the distal end portion 604, between the struts 638, and into the housing 651. This can cause the sealing member 654 to move proximally and uncover the openings 656 (see, e.g., FIGS. 11A and 11D), thereby restoring antegrade circulation through the vasculature. For purposes of illustration, the distal end portion 604 of the device 600 is shown without the frame 612 in FIG. 10B.

Figure 12A:
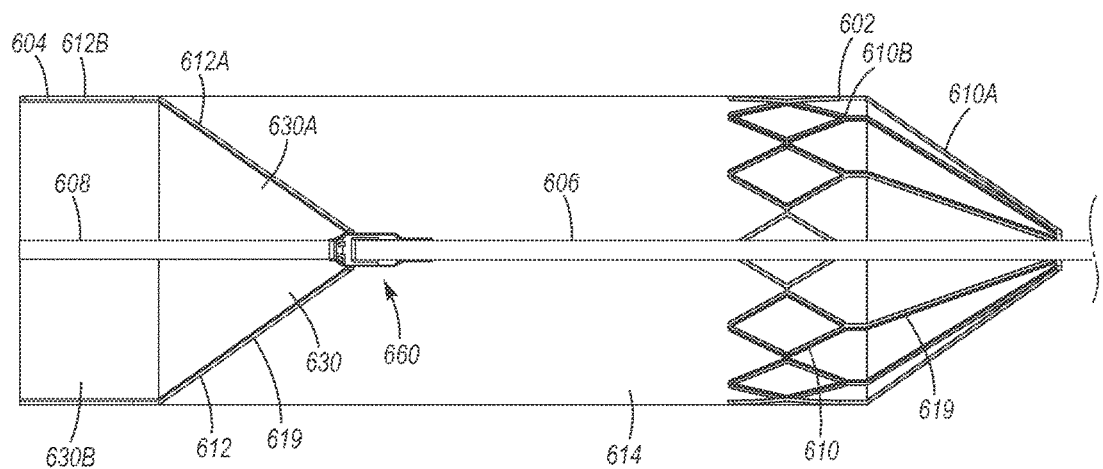
FIG. 12A is a cross-sectional view of the embodiment of FIG. 8A having an alternative embodiment of a valve.
Figure 12B:
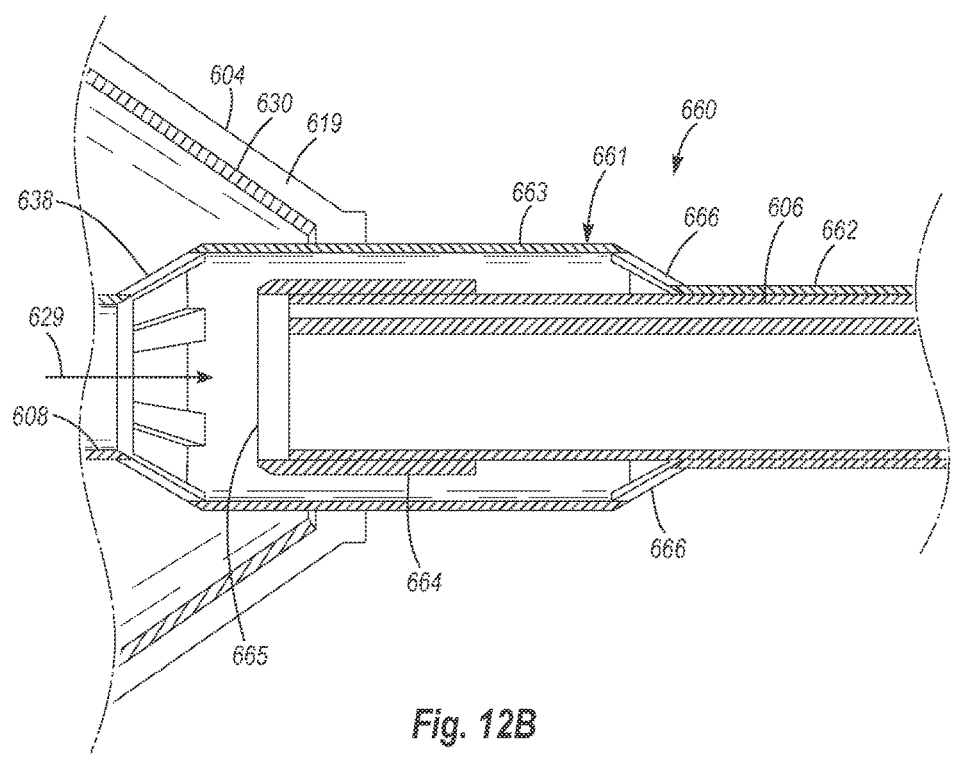
FIGS. 12B-12C are cross-sectional views of the valve of FIG. 12A.
Figure 12C:
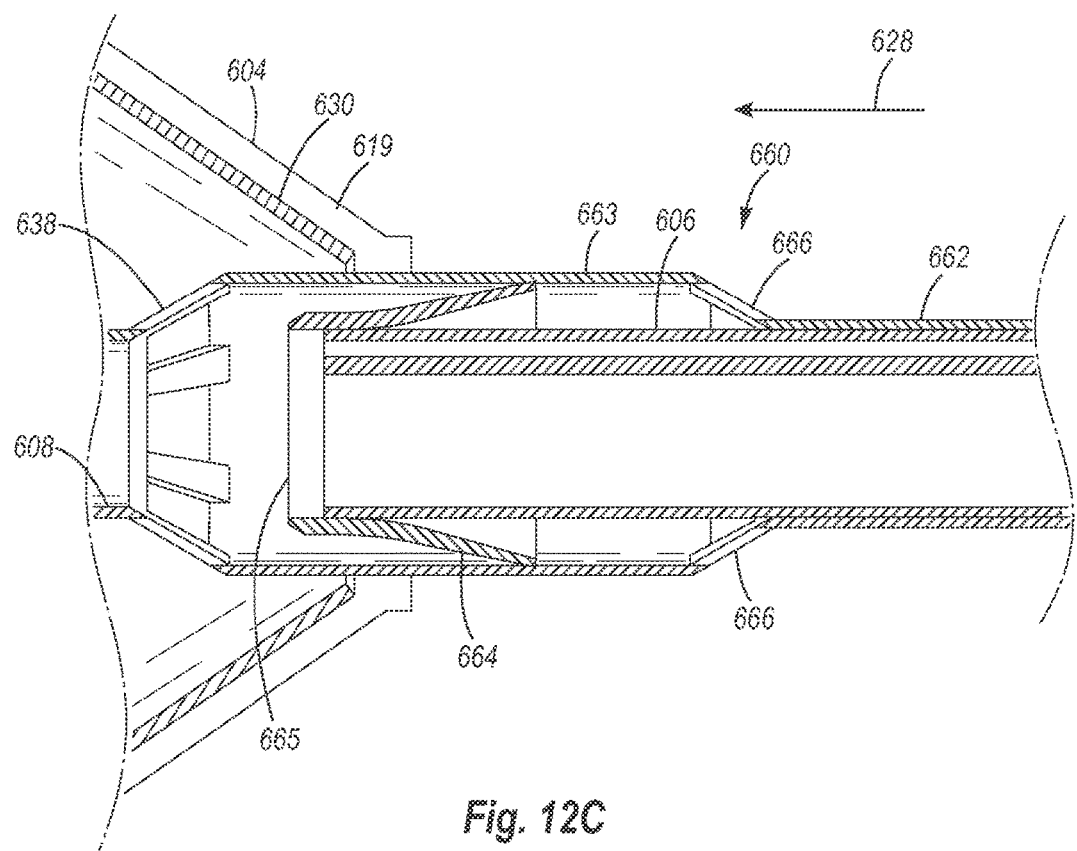

Referring now to FIGS. 12A-12C, there is shown another embodiment of a valve 660 for the device 600. The valve 660 can be a one-way valve, and can comprise a housing 661 having a proximal end portion 662 and a distal end portion 663, similar to the valves 640 and 650. The proximal end portion 662 can be secured around the first catheter 606 such that the housing 661 is retained on the first catheter 606. The proximal and distal end portions 662, 663 of the housing 661 can be connected by elongated members or struts 666 defining a plurality of openings between the proximal and distal end portions 662, 663.

The first catheter 606 can comprise a sealing member 665 having a flexible liner 664 extending circumferentially around the distal end of the first catheter 606 and movable between an open position (FIG. 12B) and a closed position (FIG. 12C). The sealing member 665 can be configured such that blood flowing in the retrograde direction of arrow 628 (see, e.g., FIGS. 12A and 12C) can cause the liner 664 of the sealing member 665 to lift radially away from the first catheter 606 and seal against the inner surface of the distal end portion 663 of the housing 661, occluding the axial passage between the distal end portion 663 and the first catheter 606. This can reduce or prevent retrograde blood flow into the distal end portion 604 of the device. When cardiac flow is reversed at the end of the cardiopulmonary bypass procedure, the relatively high pressure in the ascending aorta caused by the beating heart can cause blood to flow in the antegrade direction indicated arrow 629, into the distal end portion 604, between the struts 638, and into the distal end portion 663 of the housing 661. This can cause the liner 664 to collapse radially inwardly against the first catheter 606 (FIG. 12B), thereby allowing antegrade blood flow through the openings between the struts 666.

Figure 13A:
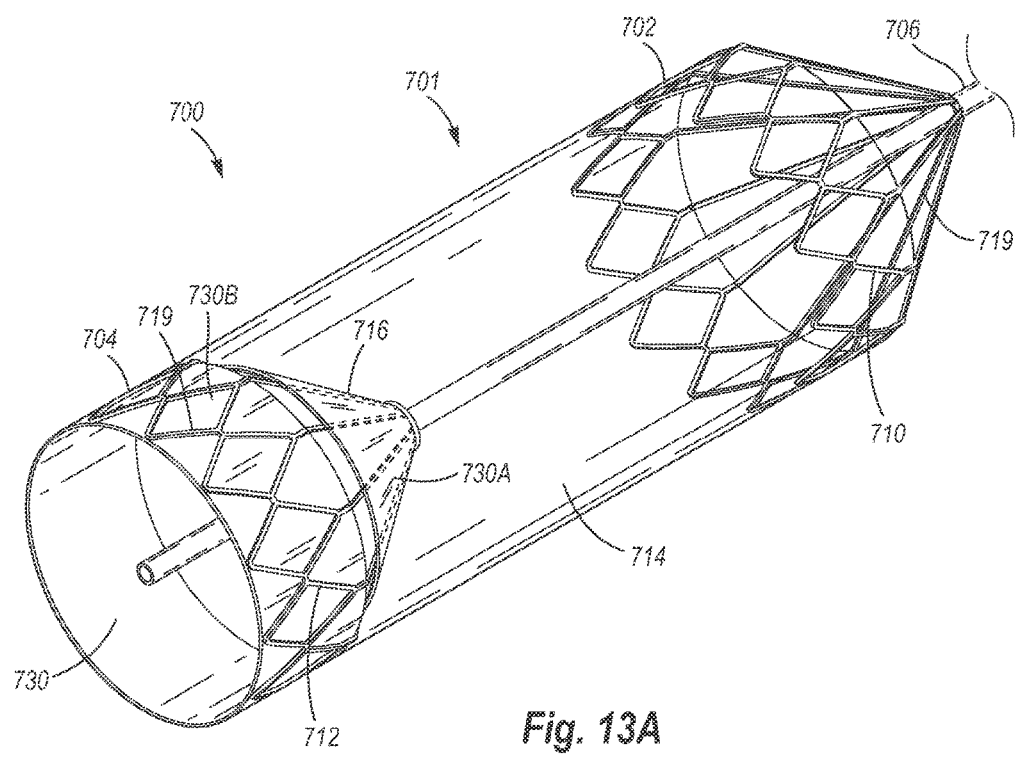
FIG. 13A is a perspective view of the embodiment of FIG. 8A including an alternative embodiment of a valve.
Figure 13B:
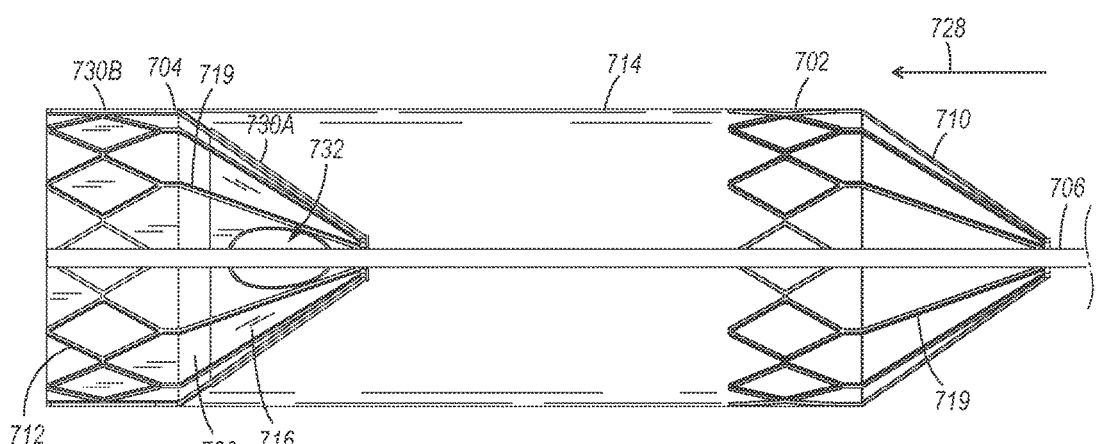
FIG. 13B is a cross-sectional view of the embodiment of FIG. 13A.
Figure 13C:
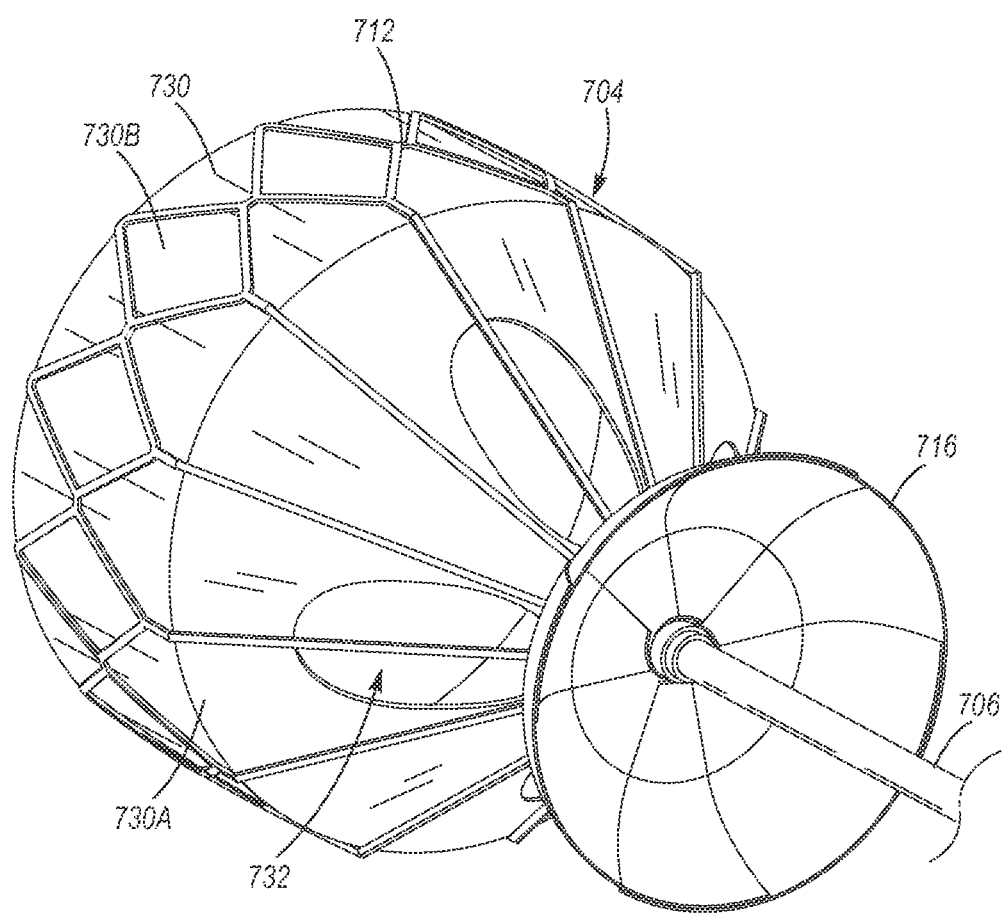
FIG. 13C is a partial perspective view of the embodiment of FIG. 13A.

Referring now to FIGS. 13A-13C, there is shown another embodiment of an aortic occlusion device 700 having a generally tubular body 701 comprising a proximal end portion 702, a distal end portion 704, and a porous membrane or covering 714 extending therebetween. The proximal and distal end portions 702, 704 can comprise radially expandable frames or stents 710, 712, respectively, formed from a plurality of angled struts 719 similar to the frames of FIGS. 8A-8D described above. The device 700 can comprise a catheter or shaft 706 extending through the distal end portion 704, through the proximal end portion 702, and out of the body through, for example, the femoral artery.

Figure 14A:
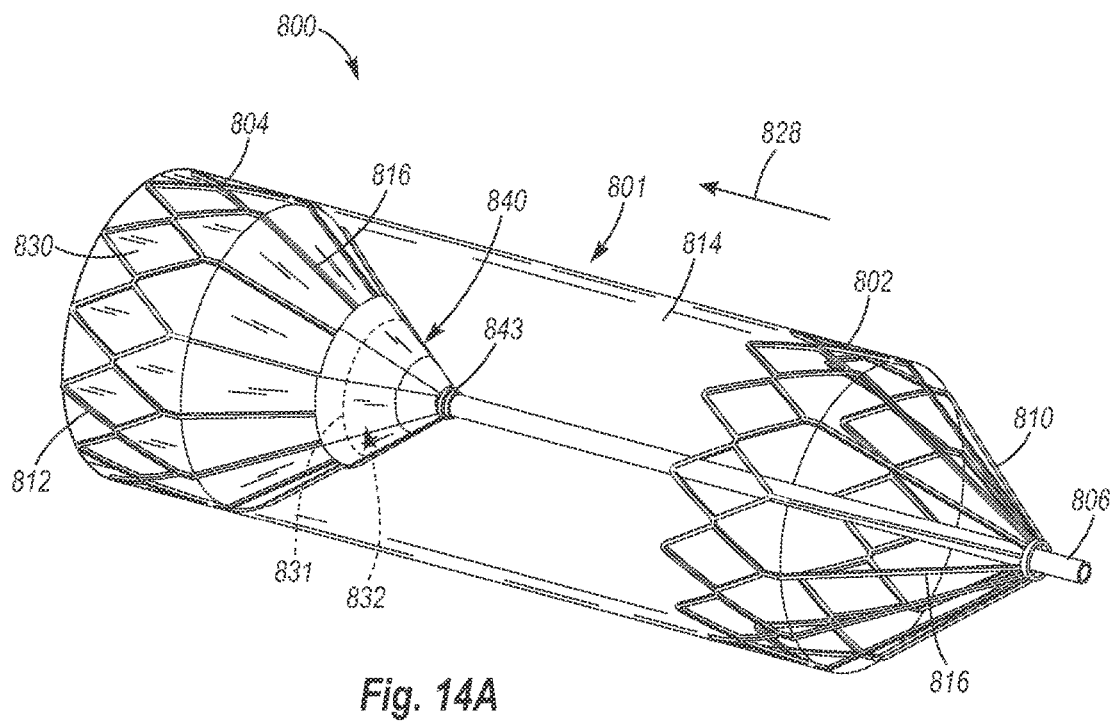
FIG. 14A is a perspective view of an alternative embodiment of an aortic occlusion device.
Figure 14B:
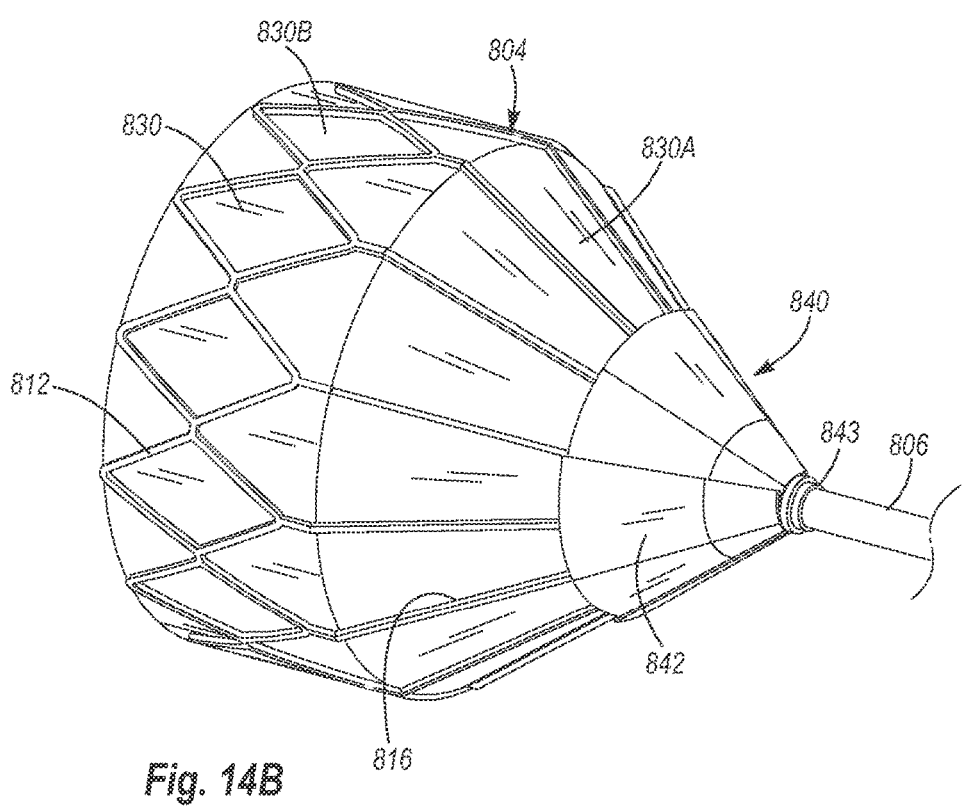
FIGS. 14B-14C are partial perspective views of the embodiment of FIG. 14A.
Figure 14C:
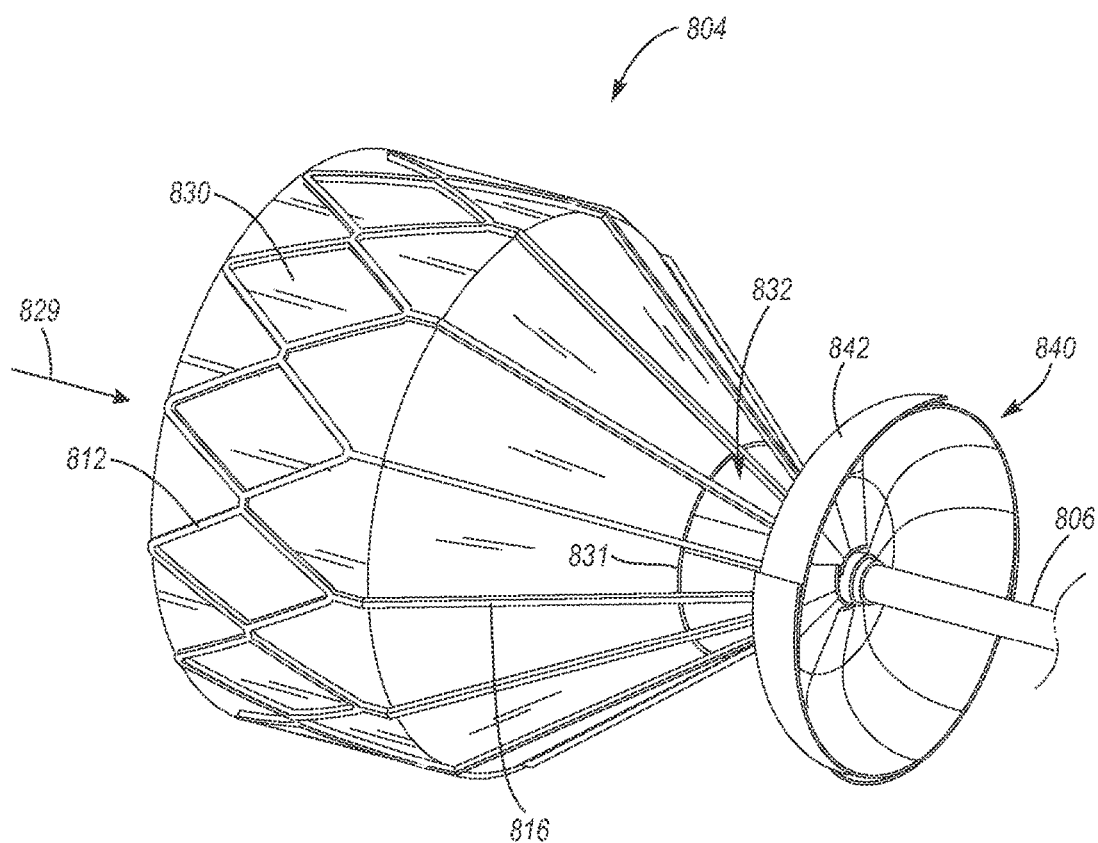

The distal end portion 704 can comprise a flexible liner 730 mounted on the frame 712 and which can have a substantially conical portion 730A and a substantially cylindrical portion 730B, similar to the liner 630. As shown in FIGS. 13B and 13C, the conical portion 730A of the liner 730 can define a plurality of openings 732, which can be covered by a flexible sealing member 716 overlaying conical portion 730A of the liner 730 on the outside of the frame 712. The sealing member 716 can be movable between an open position (FIG. 13C) and a closed position (FIG. 13A), and can be configured such that blood flowing in the retrograde direction of arrow 728 (FIG. 13B) causes the sealing member 716 to lie flush against the outside of the frame 712 and the liner 730 when in the closed position so as to cover the openings 732. In this manner, blood is prevented from flowing into the distal end portion 604 of the device and into the heart. When cardiac flow is reversed, the relatively higher blood pressure within the distal end portion 704 can cause the sealing member 716 to be lifted radially away from the liner 730 and/or moved proximally away from the frame 712 (similar to the configuration shown in FIG. 14C), thereby allowing blood to flow in the antegrade direction through the openings 732. Referring now to FIGS. 14A-14C, there is shown another embodiment of an aortic occlusion device 800 comprising a generally tubular body 801 having a proximal end portion 802, a distal end portion 804, and a porous covering 814 extending therebetween. The proximal and distal end portions 802, 804 can comprise radially expandable frames or stents 810, 812, respectively, formed from a plurality of angled struts 816 similar to the frames of FIGS. 8A-8D described above. The device can comprise a catheter 806 extending through the distal end portion 804, through the proximal end portion 802, and out of the body through, for example, the femoral artery.

The distal end portion 804 of the device 800 can comprise a flexible liner 830 mounted on the frame 812. The liner 830 can have a substantially conical portion 830A and a substantially cylindrical portion 830B similar to the liner 630. The conical portion 830A of the liner 830 can terminate at edge 831 (see FIGS. 14A and 14C) a distance distal to the proximal end of the frame 812. In this manner, openings 832 can be defined between the proximal ends of the struts 816 of the conical portion 830A and the edge 831 of the conical portion 830A.

The openings 832 can be covered by a flexible sealing member 840, which can be overlaid on the outside of the conical portion 830A of the frame 812 in a manner similar to the embodiment of FIGS. 13A-13C. The sealing member 840 can be movable between an open position (FIG. 14C) and a closed position (FIGS. 14A and 14B), and in some embodiments can comprise a plurality of overlapping leaflets or flaps 842 arrayed about an annular base or collar 843 that is secured to the first catheter 806. The sealing member 840 can be configured such that blood flowing in the retrograde direction of arrow 828 (see FIG. 14A) causes the leaflets 842 of the sealing member 840 to lie flush against the frame 812 and the proximal end portion of the liner 830 when in the closed position so as to cover the openings 832. In this manner, blood is prevented from flowing into the distal end portion 804 of the device and into the heart. When cardiac flow is reversed, the relatively higher blood pressure within the distal end portion 804 causes the sealing member 840 to lift away from the liner 830 (as shown in FIG. 14C), thereby allowing blood to flow in the antegrade direction through the openings 832, as indicated by arrow 829.

Figure 15A:
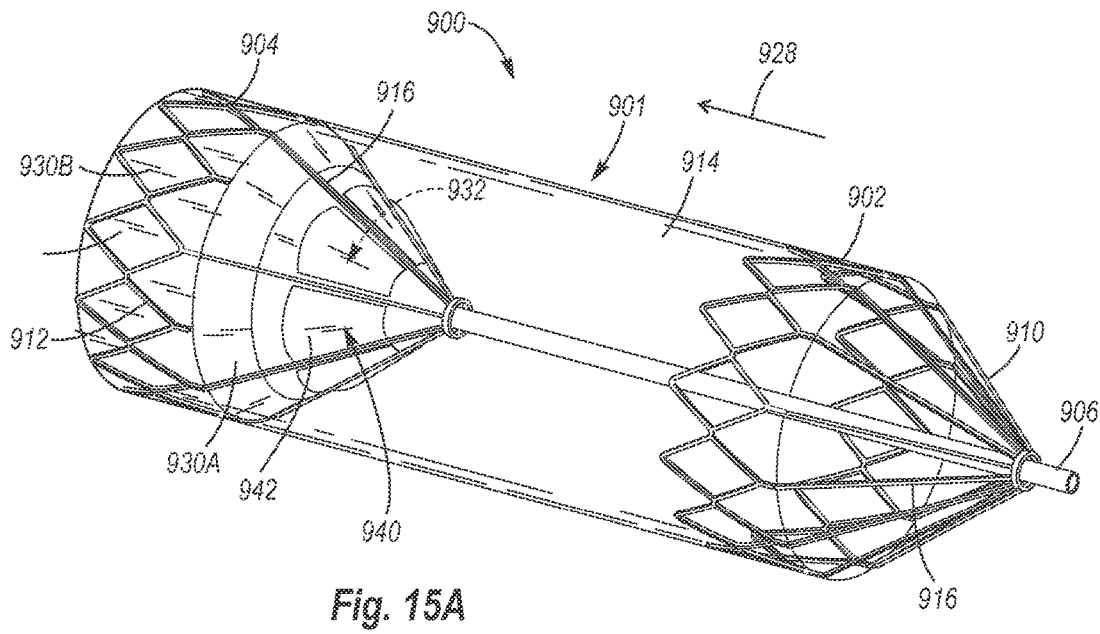
FIG. 15A is a perspective view of another embodiment of an aortic occlusion device.
Figure 15B:
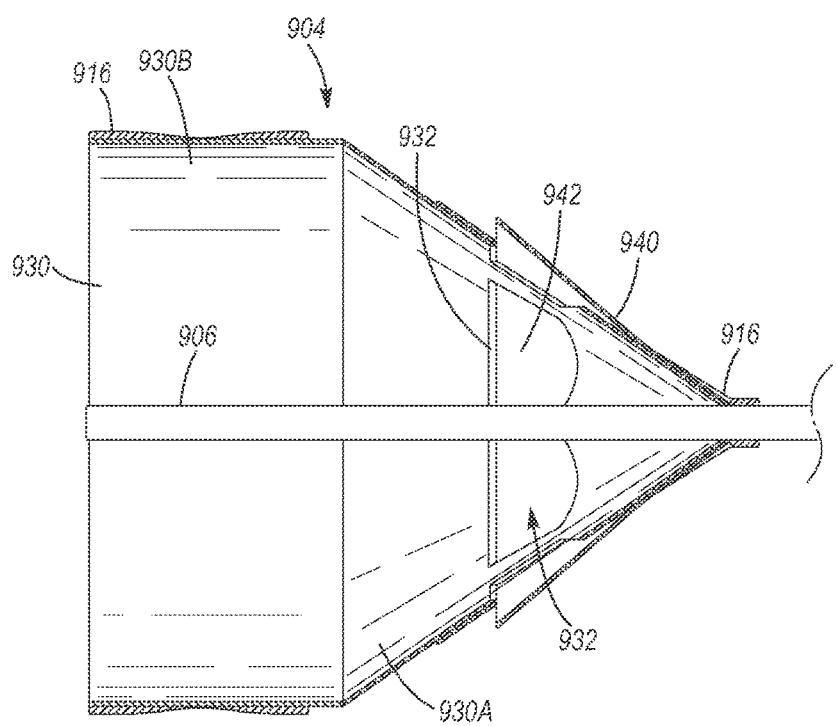
FIG. 15B is a partial cross-sectional view of the embodiment of FIG. 15A.
Figure 15C:
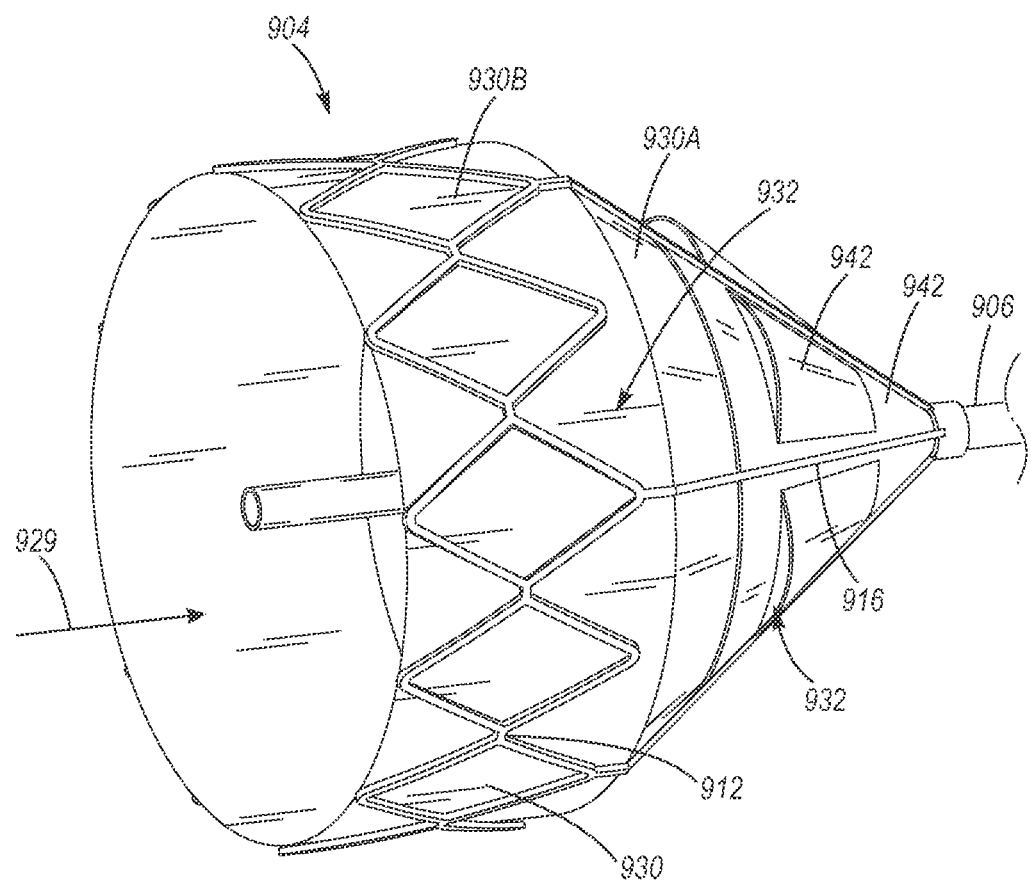
FIG. 15C is a partial perspective view of the embodiment of FIG. 15A.
Figure 16A:
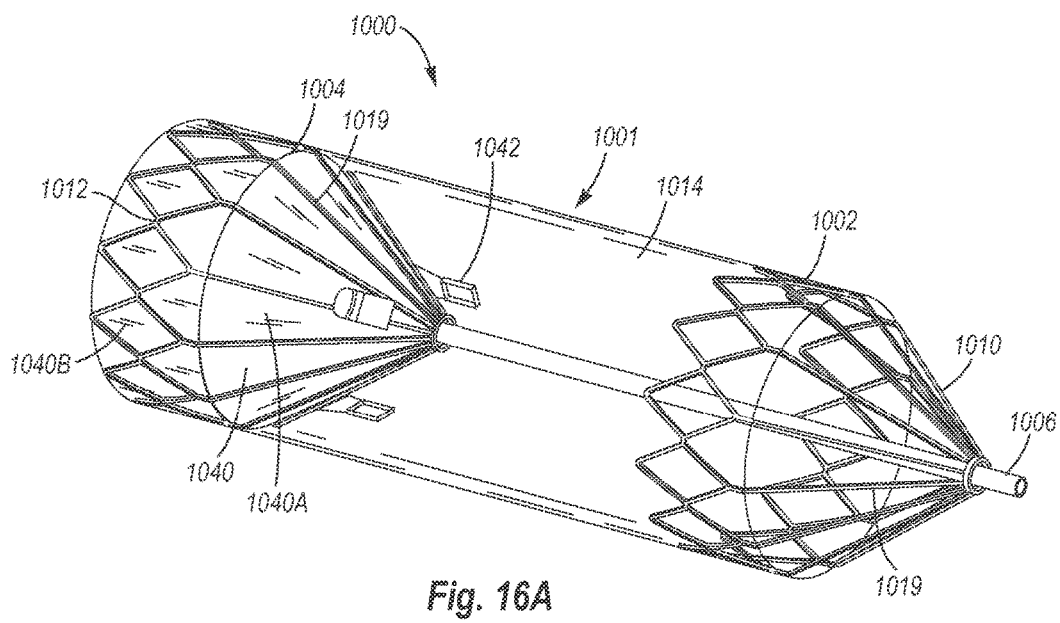
FIG. 16A is a perspective view of another embodiment of an aortic occlusion device.
Figure 16B:
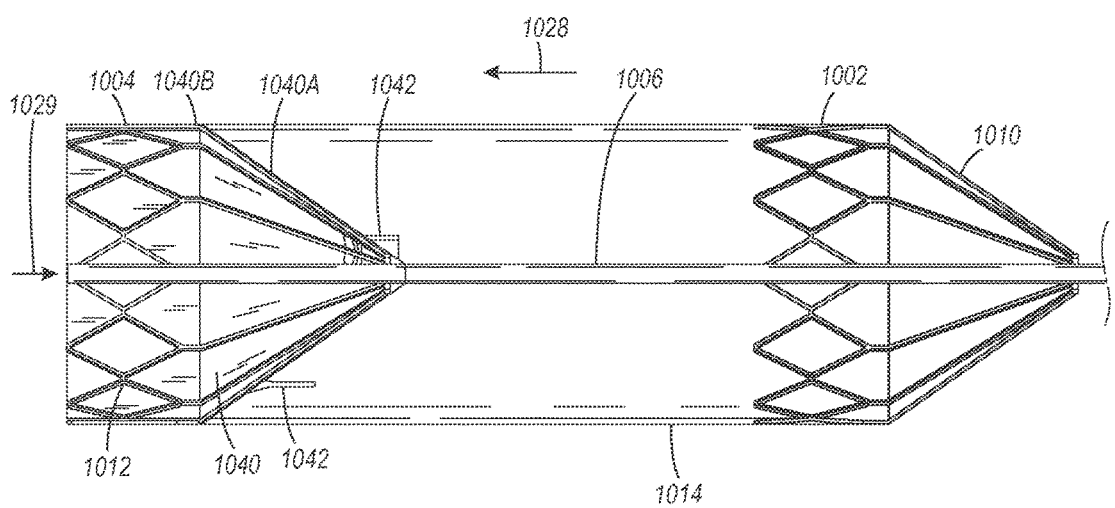
FIG. 16B is a cross-sectional view of the embodiment of FIG. 16A.
Figure 16C:
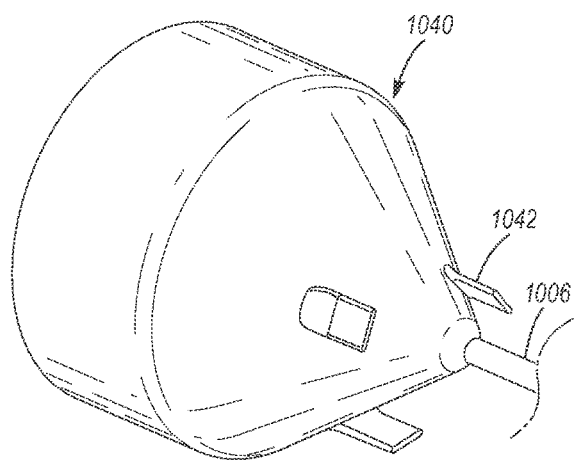
FIG. 16C is a partial perspective view of the embodiment of FIG. 16A.
Figure 16D:
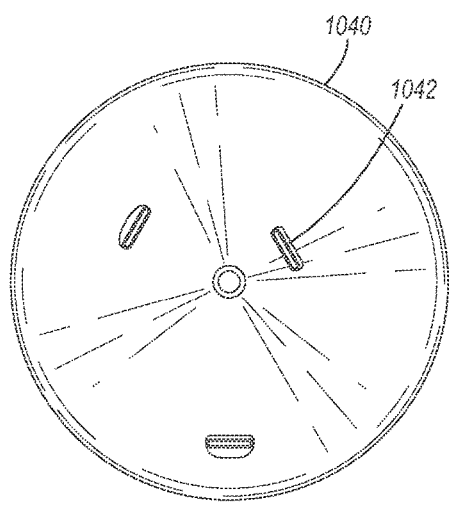
FIG. 16D is a rear view of the embodiment of FIG. 16A.

Referring now to FIGS. 15A-15C, there is shown another embodiment of an aortic occlusion device 900 comprising a generally tubular body 901 having a proximal end portion 902, a distal end portion 904, and a porous covering 914 extending therebetween. The proximal and distal end portions 902, 904 can comprise radially expandable frames or stents 910, 912, respectively, formed from a plurality of struts 916 similar to the frames of FIGS. 8A-8D described above. The device can comprise a catheter 906 extending through the distal end portion 904 through the proximal end portion 902 and out of the body through, for example, the femoral artery.

The distal end portion 904 can comprise a flexible liner 930, which can have a substantially conical portion 930A and a substantially cylindrical portion 930B similar to the liner 630. The conical portion 930A of the liner 930 can define a plurality of openings 932 disposed between the struts 916 of the frame 912, as best shown in FIGS. 15A and 15C. The openings 932 can be covered by a flexible sealing member 940, which can be overlaid on the flexible liner 930, with both the sealing member 940 and the liner 930 positioned underneath the struts 916 of the frame 912, as best illustrated in the cross-sectional view of FIG. 15B. The individual strut members 916 of the frame 912 can extend between openings 932 and over the sealing member 940, as shown in FIG. 15C.

The sealing member 940 can comprise a plurality of leaflets or flaps 942, with each leaflet corresponding to a respective one of the openings 932 in the liner 930. In some embodiments, the flaps 942 can be formed by cutting circumferentially extending slits in the sealing member 940. In this manner, the sealing member 940 can be configured such that blood flowing in the retrograde direction indicated by arrow 928 (see FIG. 15A) causes the leaflets 942 to lie flush against the liner 930 so as to cover the respective openings 932, preventing blood from flowing out of the distal end portion 904 of the device 900. When cardiac flow is reversed, the relatively higher blood pressure within the distal end portion 904 can cause the leaflets 942 of the sealing member 940 to billow open radially outwardly and lift away from the liner 930, as shown in FIG. 15C, thereby allowing antegrade blood flow through the openings 932 in the direction indicated by arrow 929.

Referring now to FIGS. 16A-16D, there is shown another embodiment of an aortic occlusion device 1000 comprising a generally tubular body 1001 having a proximal end portion 1002, a distal end portion 1004, and a porous covering 1014 extending therebetween. The proximal and distal end portions 1002, 1004 can comprise radially expandable frames or stents 1010, 1012, respectively, formed from a plurality of angled struts 1019 similar to the frames of FIGS. 8A-8D described above. The device can comprise a catheter 1006 extending through the distal end portion 1004 through the proximal end portion 1002 and out of the body through, for example, the femoral artery.

The distal end portion 1004 can comprise a flexible liner 1040, which can have a substantially conical portion 1040A and a substantially cylindrical portion 1040B similar to the liner 630. In some embodiments, the conical portion 1040A of the liner 1040 can have one or more one-way valves 1042, such as duckbill valves, as shown in FIGS. 16A-16D. The one-way valves 1042 can comprise, for example, flattened tubular pieces of flexible (e.g., elastomeric) material that are attached to, or integrally formed with, the conical portion 1040A of the liner 1040. The one-way valves 1042 can be configured such that blood flow in the direction indicated by arrow 1028 in the cross-sectional view of FIG. 16B causes the one-way valves 1042 to collapse, thereby preventing retrograde blood flow into the distal end portion 1004 and into the heart. However, when cardiac flow is reversed, the relatively higher blood pressure within the distal end portion 1004 can cause the one-way valves 1042 to open, taking an expanded tubular configuration, and allowing blood to flow through the valves in the antegrade direction indicated by arrow 1029. In some embodiments, the device 1000 can include one, two, three, or more one-way valves 1042. Plural one-way valves 1042 can be staggered in radial, circumferential, and/or axial position to provide a smaller collapsed diameter of the device 1000 during delivery and removal.

Figure 17:
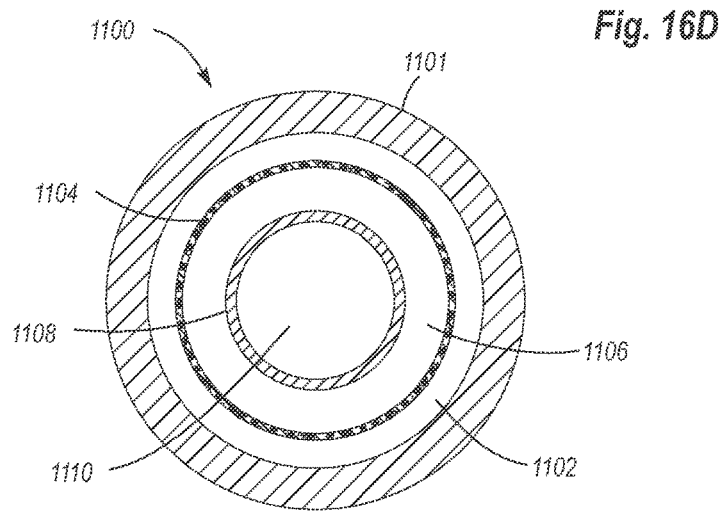
FIG. 17 is a cross-sectional view of a delivery catheter for an aortic occlusion device.

Referring now to FIG. 17, there is shown a cross-sectional view of an aortic occlusion device delivery catheter 1100 illustrating a sheath 1101, a stent 1102, a porous covering 1104, a space 1106 in which to compact the porous covering 1104, a ferrule 1108, and a lumen 1110 shown in delivery configuration from which the stent 1102 can be deployed and radially expanded. It should be understood that the delivery catheter 1100 can be used in combination with any of the aortic occlusion devices disclosed herein.

Figure 18A:
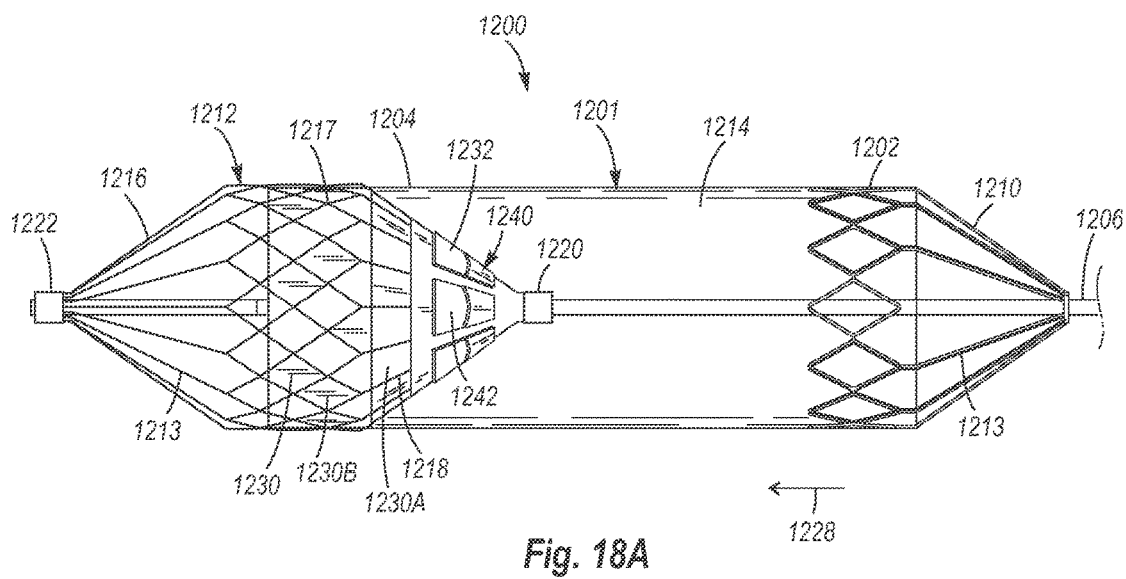
FIG. 18A is a perspective view of another embodiment of an aortic occlusion device.
Figure 18B:
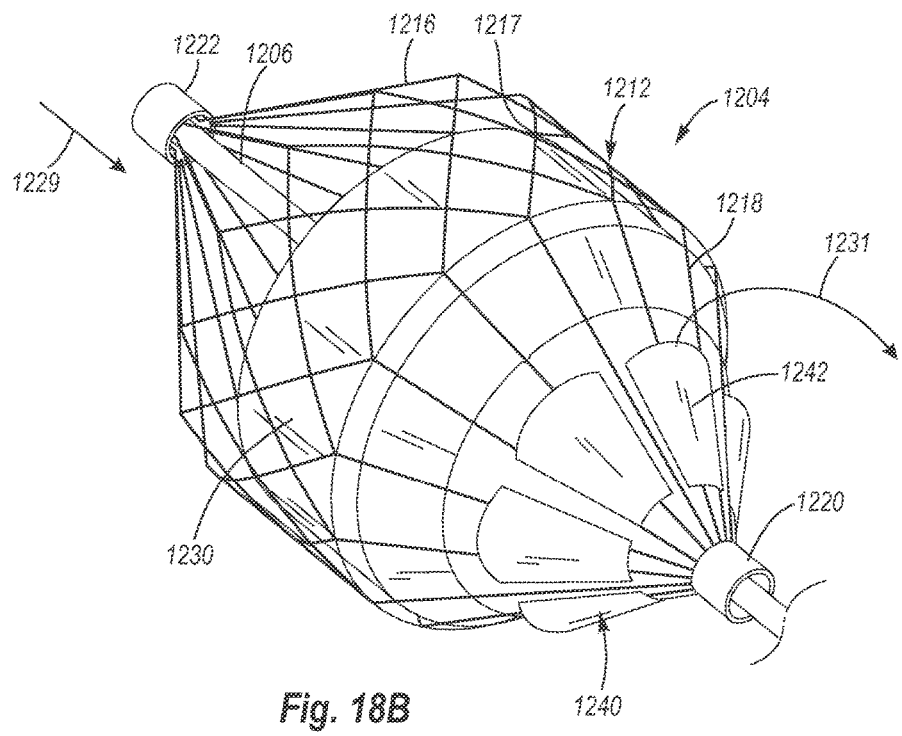
FIG. 18B is a partial perspective view of the embodiment of FIG. 18A.

Referring now to FIGS. 18A-18B, there is shown another embodiment of an aortic occlusion device 1200 comprising a generally tubular body 1201 having a proximal end portion 1202, a distal end portion 1204, and a porous covering 1214 extending therebetween. The proximal and distal end portions 1202, 1204 can comprise radially expandable frames or stents 1210, 1212, respectively, formed from a plurality of angled struts 1213. In some embodiments, the distal frame 1212 can comprise a first conical portion 1216 and a second conical portion 1218, the first and second conical portions 1216, 1218 being separated by a cylindrical portion 1217. The struts 1213 of the conical portions 1216, 1218 can be retained by respective collars 1222, 1220, which can be slidably disposed around a catheter 1206. The catheter 1206 can extend through the distal end portion 1204, through the proximal end portion 1202, and out of the body through, for example, the femoral artery.

The distal end portion 1204 can comprise a flexible liner 1230, which can have a substantially conical portion 1230A secured to the second conical portion 1218 of the distal frame 1212, and a substantially cylindrical portion 1230B secured to the cylindrical portion 1217 of the distal frame 1212. In some embodiments, the conical portion 1230A of the liner 1230 can define a plurality of openings 1232, as shown in FIG. 18A. The openings 1232 can be covered by a flexible sealing member 1240, which can be overlaid on the flexible liner 1230 and positioned underneath the frame 1212. As shown in FIG. 18B, which illustrates the distal end portion 1204 with the porous covering 1214 removed, the sealing member 1240 can comprise a plurality of leaflets 1242. Each leaflet 1242 can correspond to a respective opening 1232 in the liner 1230.

The leaflets 1242 can be disposed over one or more struts of the frame 1212, as the number of struts can be large and the spaces between the struts can be narrow. The leaflets 1242 can have an open distal end that is free to billow open away from the rest of the sealing member 1240 to uncover the openings 1232 during antegrade blood flow through the openings 1232. The sealing member 1240 can be configured such that blood flowing in the retrograde direction of arrow 1228 (see FIG. 18A) causes the leaflets 1242 to lie flush against the sealing member 1240 and the struts so as to cover the openings 1232. In this manner, blood is prevented from flowing into the distal end portion 1204 of the device. When cardiac flow is reversed, the relatively higher blood pressure causes the leaflets 1242 of the sealing member 1240 to lift away from the sealing member, thereby allowing blood to flow in the antegrade direction through the openings 1232, as indicated by arrows 1229 and 1231 of FIG. 18B.

Figure 19A:
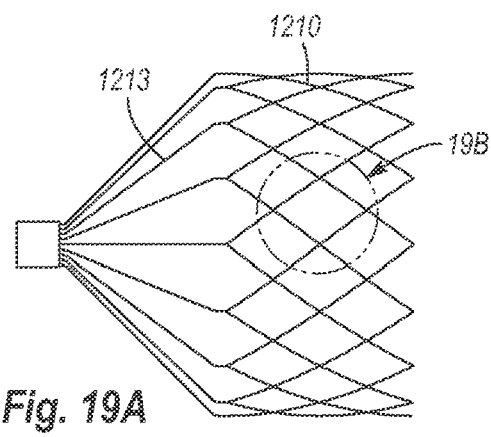
FIG. 19A is a side elevation view of an embodiment of a frame.
Figure 19B:
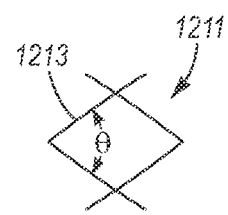
FIG. 19B is an enlarged view of a diamond unit cell of the embodiment of FIG. 19A.
Figure 19C:
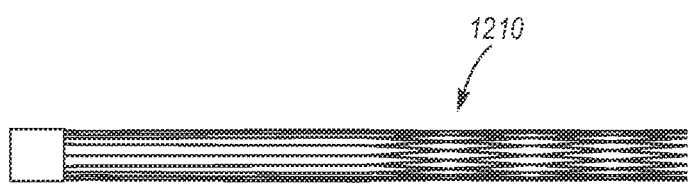
FIG. 19C is a side elevation view of the embodiment of FIG. 19A in a radially collapsed state.

Referring now to FIGS. 19A-19C, there is shown an embodiment of the frame 1210 having a plurality of struts 1213 that make up a conical portion. In some embodiments, the struts 1213 can be arranged so as to form a diamond-shaped unit cell pattern, such as representative unit cell 1211 shown in FIG. 19B. The unit cells such as representative unit cell 1211 can have an angle θ between struts 1213 at laterally opposed corners of the unit cells. In some embodiments, the angle θ can be about 72 degrees. In this manner, the frame 1210 can be configured to radially collapse into an elongated cylindrical shape for loading into a delivery catheter, as shown in FIG. 19C.

Figure 20A:
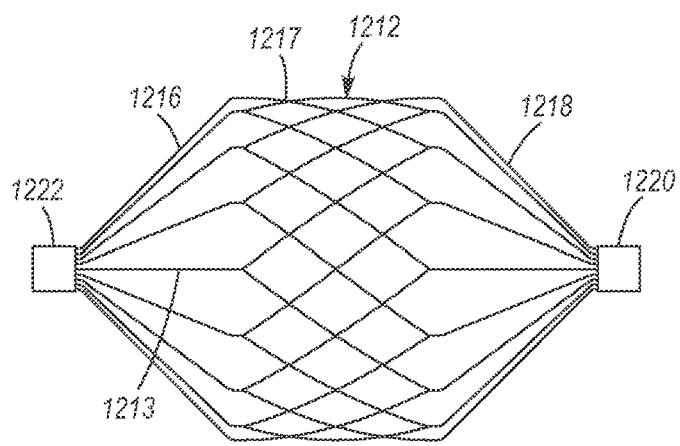
FIG. 20A is a side elevation view of another embodiment of a frame.
Figure 20B:
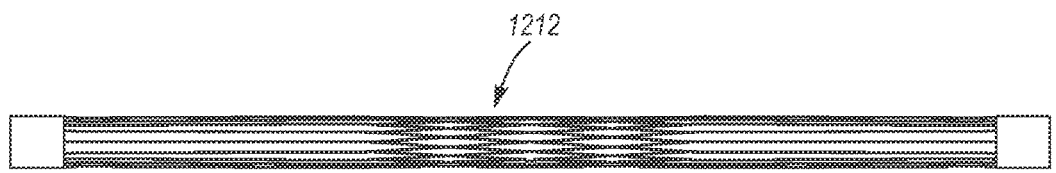
FIG. 20B is a side elevation view of the embodiment of FIG. 20A in a radially collapsed state.

FIGS. 20A-20B illustrate the frame 1212 including the first conical portion 1216, the second conical portion 1218, and the cylindrical portion 1217 disposed therebetween. In some embodiments, the struts 1213 of the cylindrical portion 1217 can have the same or substantially the same diamond-shaped unit cell pattern as the representative unit cell 1211 shown in FIG. 19B. In a similar manner, the frame 1212 can be configured to radially collapse into an elongated cylindrical shape for loading into a delivery catheter, as shown in FIG. 20B.

Figure 21A:
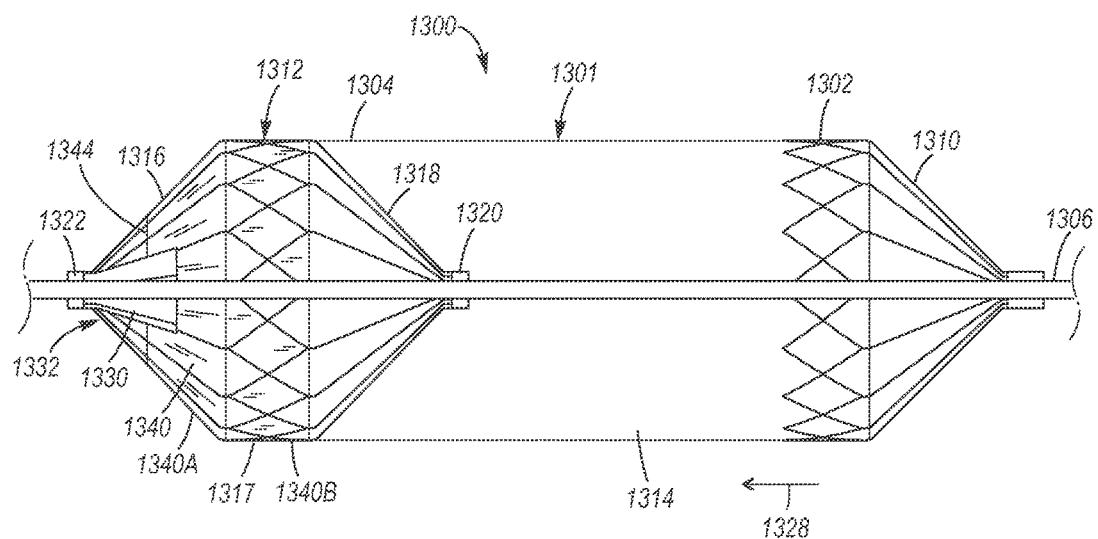
FIG. 21A is a cross-sectional side elevation view of another embodiment of an aortic occlusion device.
Figure 21B:
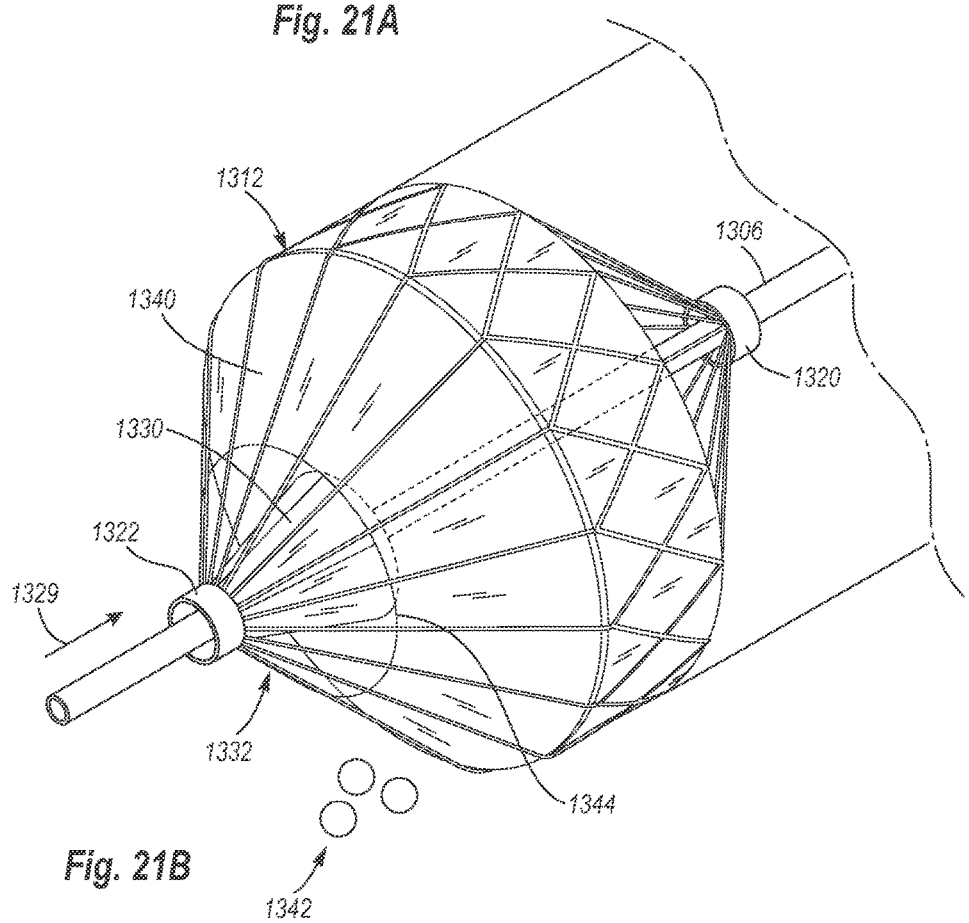
FIG. 21B is a partial perspective view of the embodiment of FIG. 21A.

Referring now to FIGS. 21A-21B, there is shown another embodiment of an aortic occlusion device 1300 comprising a generally tubular body 1301 having a proximal end portion 1302, a distal end portion 1304, and a porous covering 1314 extending therebetween. The proximal and distal end portions 1302, 1304 can comprise radially expandable frames or stents 1310, 1312, respectively, which can be formed by a plurality of angled struts 1319, as shown in the cross-sectional view of FIG. 21A. In some embodiments, the distal frame 1312 can comprise a first conical portion 1316 and a second conical portion 1318, the conical portions 1316, 1318 being separated by a cylindrical portion 1317. The struts 1319 of the conical portions 1316, 1318 can be retained by respective collars 1322, 1320, which can be slidably disposed around a catheter 1306. The catheter 1306 can extend through the distal end portion 1304, through the proximal end portion 1302, and out of the body through, for example, the femoral artery.

The distal end portion 1304 can comprise a flexible liner 1340, which can have a substantially conical portion 1340A secured to the first conical portion 1316 of the distal frame 1312. The liner 1340 can also include a substantially cylindrical portion 1340B secured to the cylindrical portion 1317 of the distal frame 1312. In some embodiments, the conical portion 1340A of the liner 1340 can have a distal edge 1344 that terminates a distance proximal to the distal collar 1322, thereby defining a distal opening 1332, as best shown in FIG. 21B. A flexible sealing member 1330 can be disposed around the catheter 1306 in the interior of the distal frame 1312, and can be movable between an open position and a closed position. In the open position, retrograde blood flow in the direction indicated by arrow 1328 (FIG. 21A) can cause the sealing member 1330 to flare radially and contact the interior surface of the liner 1340 around the periphery of the opening 1330, thereby preventing retrograde blood flow out of the distal end portion 1304 through the opening 1330. When cardiac flow is reversed, the relatively higher blood pressure can cause the sealing member 1330 to collapse radially toward the first catheter 1306 and away from the liner 1340, thereby allowing blood to flow in the antegrade direction through the opening 1332, as indicated by arrow 1329 in FIG. 21B. In some embodiments, the conical portion 1316 of the frame 1312 and the liner 1340 can act to trap emboli 1342 suspended in the antegrade bloodstream in the radial crevices adjacent to the aortic wall, as shown in FIG. 21B.

Figure 22A:
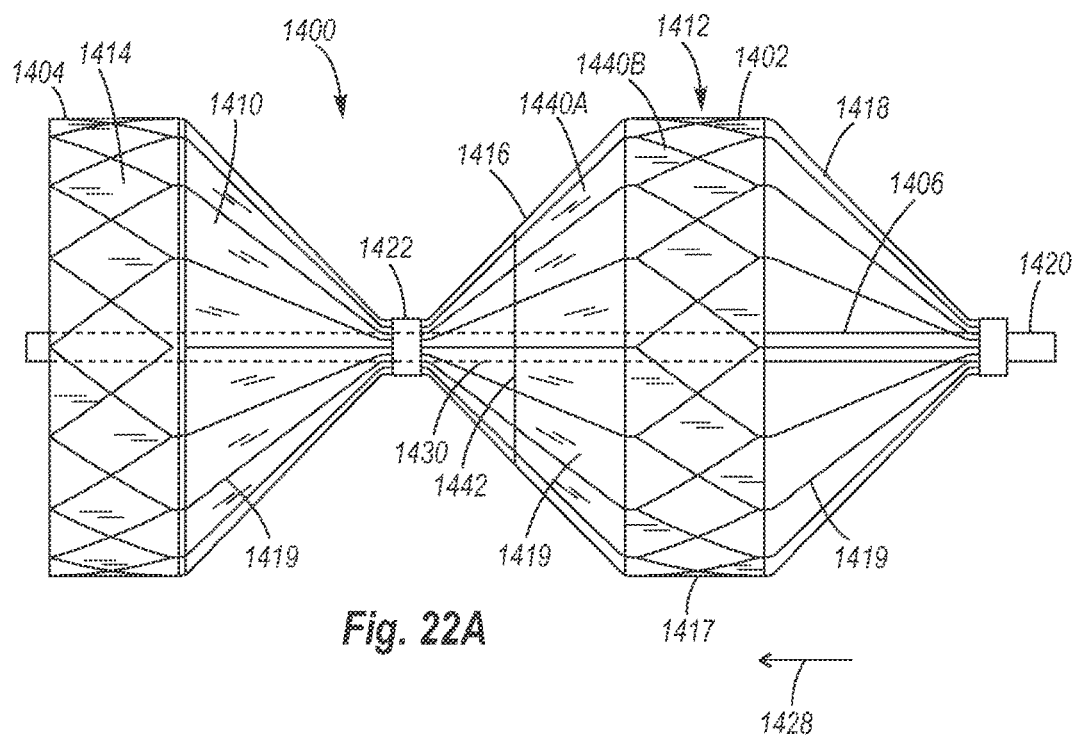
FIG. 22A is a side elevation view of another embodiment of an aortic occlusion device.
Figure 22B:
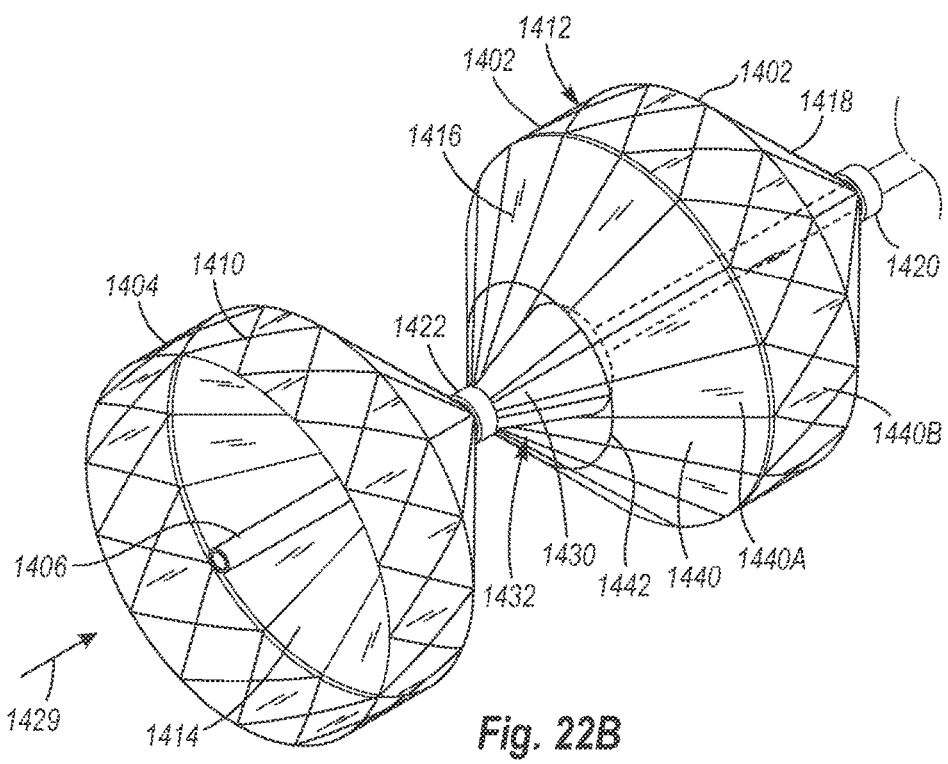
FIG. 22B is a perspective view of the embodiment of FIG. 22A showing a sealing member in the open position.
Figure 22C:
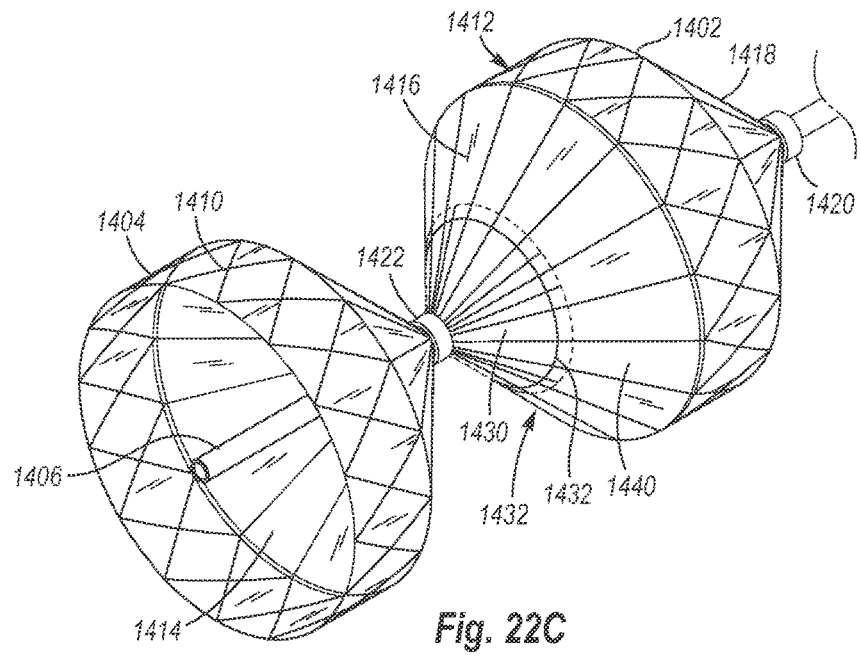
FIG. 22C is a perspective view of the embodiment of FIG. 22A showing a sealing member in the closed position.

Referring now to FIGS. 22A-22C, there is shown another embodiment of an aortic occlusion device 1400 having a proximal end portion 1402, and a distal end portion 1404. The proximal and distal end portions 1402, 1404 can comprise radially expandable frames or stents 1412, 1410, respectively, formed from a plurality of angled struts 1419. In some embodiments, the proximal frame 1412 can comprise a first conical portion 1416 and a second conical portion 1418, the conical portions 1416, 1418 being separated by a cylindrical portion 1417. The struts 1419 of the conical portions 1416, 1418 can be retained by respective collars 1422, 1420, at least one of which can be slidably disposed around a catheter 1406. The catheter 1406 can extend through the distal end portion 1404, through the proximal end portion 1402, and out of the body through, for example, the femoral artery.

Figure 23A:
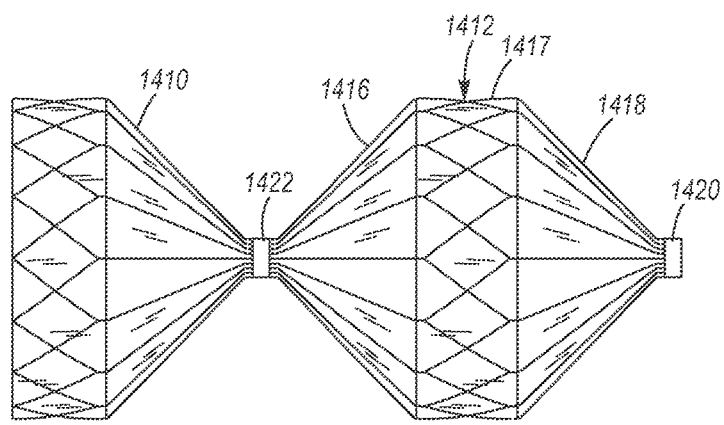
FIG. 23A is a side elevation view of the frame of FIG. 22A.
Figure 23B:
FIG. 23B is a side elevation view of the frame of FIG. 23A in a radially collapsed state.

The distal end portion 1404 can have a porous liner 1414 mounted on the distal frame 1410. The proximal end portion 1402 can comprise a flexible liner 1440, which can have a substantially conical portion 1440A and a substantially cylindrical portion 1440B (FIG. 22A). In some embodiments, the conical portion 1440A of the liner 1440 can have a distal edge 1442 that terminates a distance proximal to the collar 1422, thereby defining an opening 1432, as shown in FIG. 22B. A flexible sealing member 1430 can be disposed around the catheter 1406 in the interior of the frame 1412, and can be movable between an open position (FIG. 22B) and a closed position (FIGS. 22A and 22C). Retrograde blood flow in the direction indicated by arrow 1428 (FIG. 22A) can cause the sealing member 1430 to contact the interior surface of the liner 1440 around the periphery of the opening 1432, thereby preventing retrograde blood flow out of the proximal end portion 1402 through the opening 1432. When cardiac flow is reversed, the relatively higher blood pressure causes the sealing member 1430 to collapse radially toward the catheter 1406 and away from the liner 1440, thereby allowing blood to flow in the antegrade direction through the opening 1432 into the proximal end portion 1402, as indicated by arrow 1429 of FIG. 22B. In some embodiments, the frames 1410, 1412 can be configured to be radially collapsed from a fully expanded configuration shown in FIG. 23A to a substantially cylindrical shape shown in FIG. 23B for insertion into the patient's vasculature.

Figure 24A:
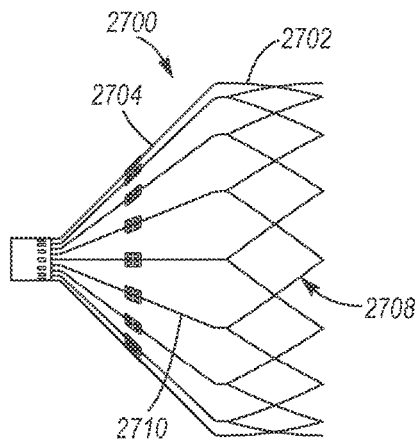
FIGS. 24A-24D are side elevation views of alternative embodiments of frames.
Figure 24B:
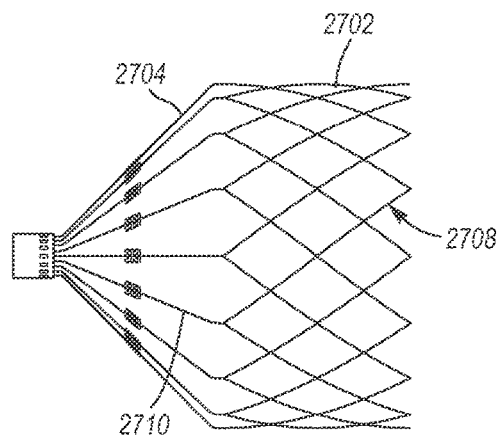
Figure 24C:
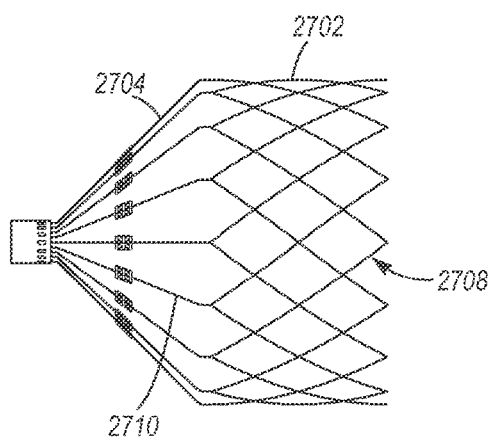
Figure 24D:
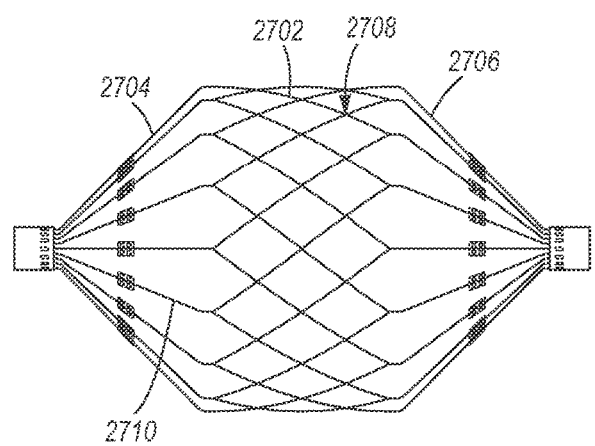

FIGS. 24A-24D illustrate a variety of embodiments of a frame 2700. The frame 2700 can have a cylindrical portion 2702 and a conical portion 2704, and can be formed from a plurality of angled struts 2710, as shown in FIG. 24A. The cylindrical portion 2702 can be configured such that the struts 2710 are arranged to form a plurality of diamond-shaped unit cells generally indicated at 2708. In the embodiment of FIG. 24A, the cylindrical portion 2702 includes a single row of unit cells 2708. In the embodiments of FIGS. 24B, 24C, and 24D, the cylindrical portion 2702 includes three adjacent rows of unit cells 2708. However, in alternative embodiments, the cylindrical portion 2702 can comprise any suitable number of rows of diamond-shaped unit cells. In some embodiments, the frame 2700 can comprise a first conical portion 2704, a second conical portion 2706, and a cylindrical portion 2702 extending therebetween, as shown in FIG. 24D, with the central conical portion having any suitable number of rows of closed unit cells 2708.

Figure 25:
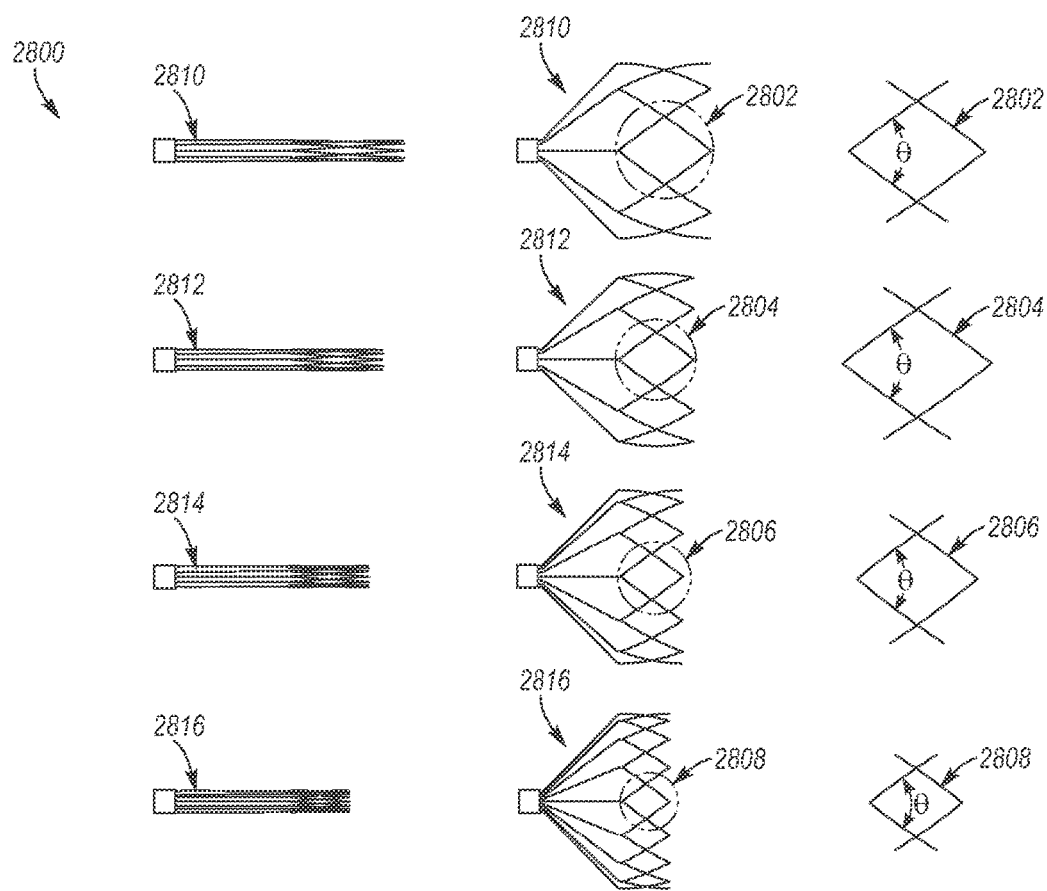
FIG. 25 is a schematic illustration of alternative embodiments of frames.

Referring now to FIG. 25, there is shown various embodiments of a frame 2800 illustrating various configurations of diamond-shaped unit cells 2802, 2804, 2806, 2808. In some embodiments, the cells can have an angle θ defined between struts at laterally opposed corners of the diamonds. In some embodiments, the angle θ can be about 72 degrees in an expanded state. In one representative embodiment indicated at 2810, the circumference of the frame 2810 can include eight or more diamond unit cells 2802. Each diamond unit cell 2802 can have sides with a length of about 12 mm, which can allow the frame 2810 to collapse into a cylindrical shape having a diameter of about 5 mm and a length of about 60 mm.

In another representative embodiment indicated at 2812, the circumference of the frame 2812 can include 10 or more diamond unit cells 2804. In some embodiments, each diamond unit cell 2804 can have sides with a length of about 10 mm, which can allow the frame 2812 to collapse into a cylindrical shape having a diameter of about 5 mm and a length of about 54 mm.

In another representative embodiment indicated at 2814, the circumference of the frame 2814 can include twelve or more diamond unit cells 2806. In some embodiments, each diamond unit cell 2806 can have sides with a length of about 8 mm, which can allow the frame 2814 to collapse into a cylindrical shape having a diameter of about 5 mm and a length of about 50 mm.

In another representative embodiment indicated at 2816, the circumference of the frame 2816 can include sixteen or more diamond unit cells 2808. In some embodiments, each diamond unit cell 2808 can have sides with a length of about 6 mm, which can allow the frame 2816 to collapse into a cylindrical shape having a diameter of about 5 mm and a length of about 46 mm.

Figure 26:
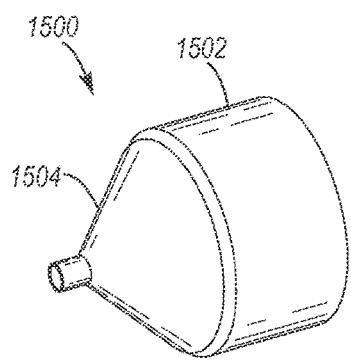
FIG. 26 is a perspective view of an alternative embodiment of a liner.
Figure 27:
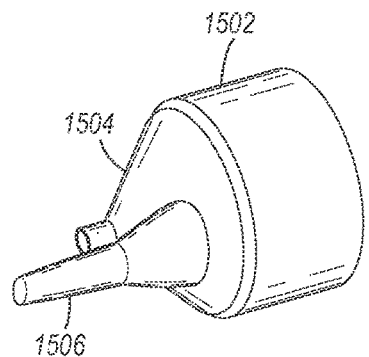
FIG. 27 is a side elevation view of another embodiment of a liner.
Figure 28:
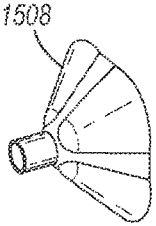
FIG. 28 is a side elevation view of another embodiment of a liner.

FIGS. 26-28 illustrate various embodiments of a liner 1500 that can be used with a structural frame to control blood flow. As shown in FIG. 26, the liner 1500 can comprise a substantially cylindrical portion 1502 and a substantially conical portion 1504, and can be fabricated from a polymeric material. In some embodiments, the liner 1500 can comprise one or more valves, such as the duckbill or flapper valve 1506 shown in FIG. 27. In other embodiments, the liner 1500 can comprise a substantially pyramidal portion 1508 having rounded corners, as illustrated in FIG. 28. In some embodiments, the liner 1500 can be dip-molded and trimmed to the appropriate size.

Referring now to FIGS. 29A-29D, there is shown another embodiment of an aortic occlusion device 1600 comprising a generally tubular body 1601 having a proximal end portion 1602, a distal end portion 1604, and a porous covering 1614 extending therebetween. The proximal and distal end portions 1602, 1604 can comprise radially expandable frames or stents 1610, 1612, respectively, formed from a plurality of angled struts 1619. In some embodiments, the frame 1612 can comprise a first conical portion 1616 and a second conical portion 1618, the conical portions 1616, 1618 being separated by a cylindrical portion 1617. The struts 1619 of the conical portions 1616, 1618 can be retained in respective collars 1622, 1620, which can be slidably disposed around a catheter 1606. The catheter 1606 can extend through the distal end portion 1604, through the proximal end portion 1602, and out of the body through, for example, the femoral artery. In some embodiments, the catheter 1606 can project a distance distal from distal end portion 1604. However, in alternative embodiments, the catheter 1606 can terminate at any suitable distance adjacent the distal end portion 1604 of the device.

Figure 29A:
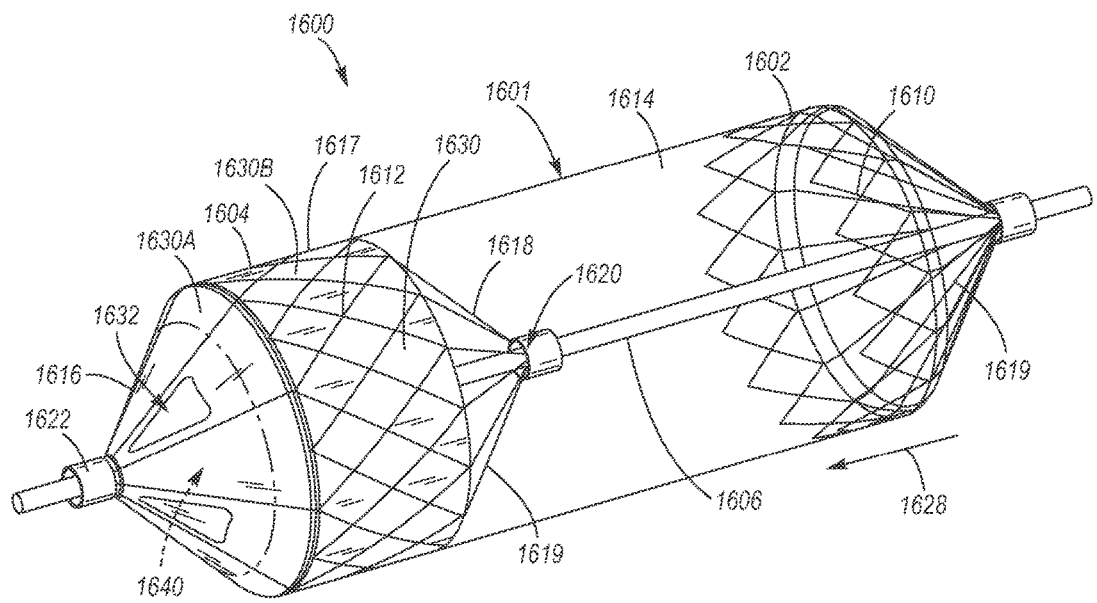
FIG. 29A is a perspective view of another embodiment of an aortic occlusion device.
Figure 29B:
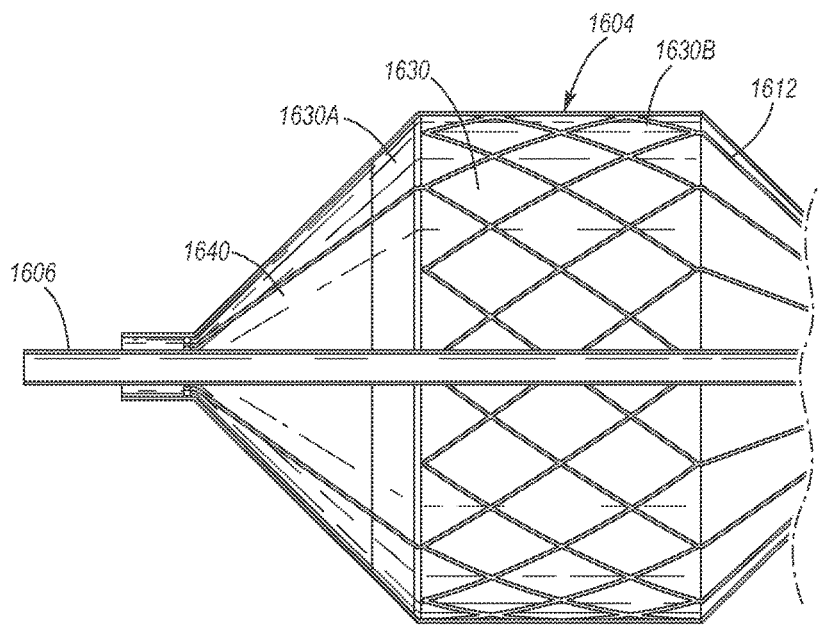
FIG. 29B is a partial cross-sectional view of the embodiment of FIG. 29A.
Figure 29C:
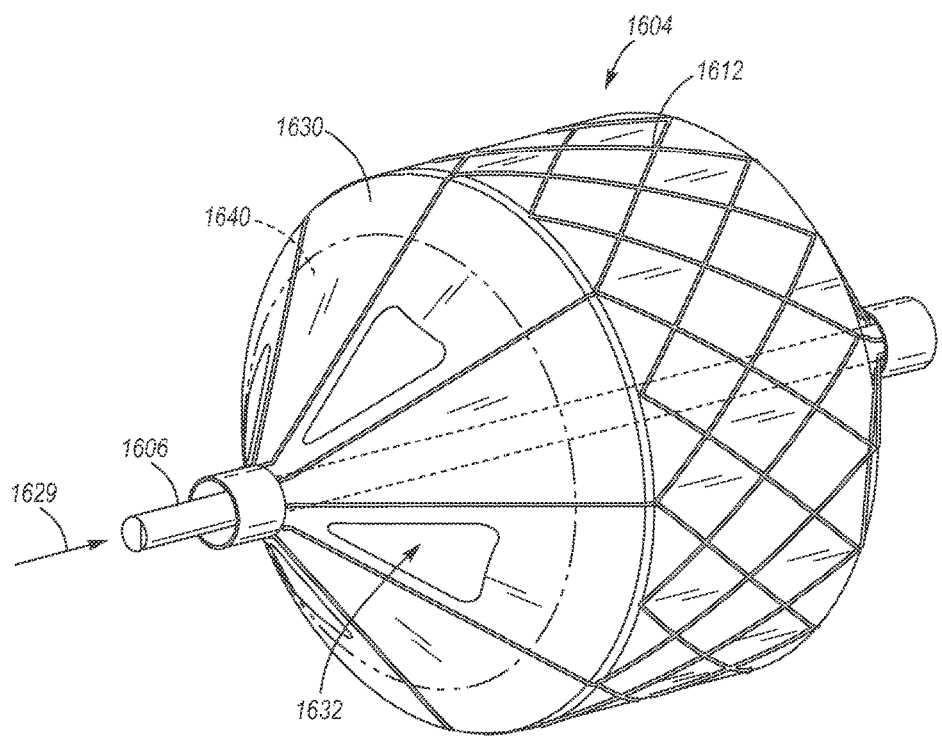
FIG. 29C is a partial perspective view of the embodiment of FIG. 29A.
Figure 29D:
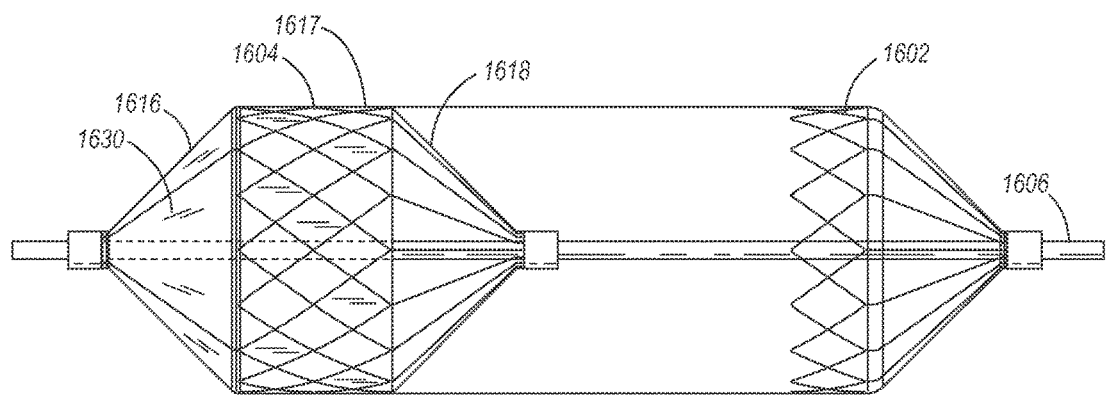
FIG. 29D is a cross-sectional side elevation view of the embodiment of FIG. 29A.

The distal end portion 1604 can comprise a liner 1630, which can have a substantially conical portion 1630A and a substantially cylindrical portion 1630B, as shown in FIG. 29B. In some embodiments, the conical portion 1630A of the liner 1630 can define a plurality of openings 1632, as shown in FIGS. 29A and 29C. The openings 1632 can be covered by a flexible sealing member 1640, which can be disposed adjacent an interior surface of the conical portion 1630A of the liner 1630. In this manner, the sealing member 1640 can be configured such that retrograde blood flow in the direction of arrow 1628 (see FIG. 29A) causes the sealing member 1640 to lie flush against the liner 1630 so as to cover the openings 1632. In this manner, blood is prevented from flowing out of the distal end portion 1604 of the device and into the heart. When cardiac flow is reversed, the relatively higher blood pressure can cause the sealing member 1640 to collapse radially away from the liner 1630, thereby allowing blood to flow in the antegrade direction through the openings 1632, as indicated by arrow 1629 in FIG. 29C.

Figure 30A:
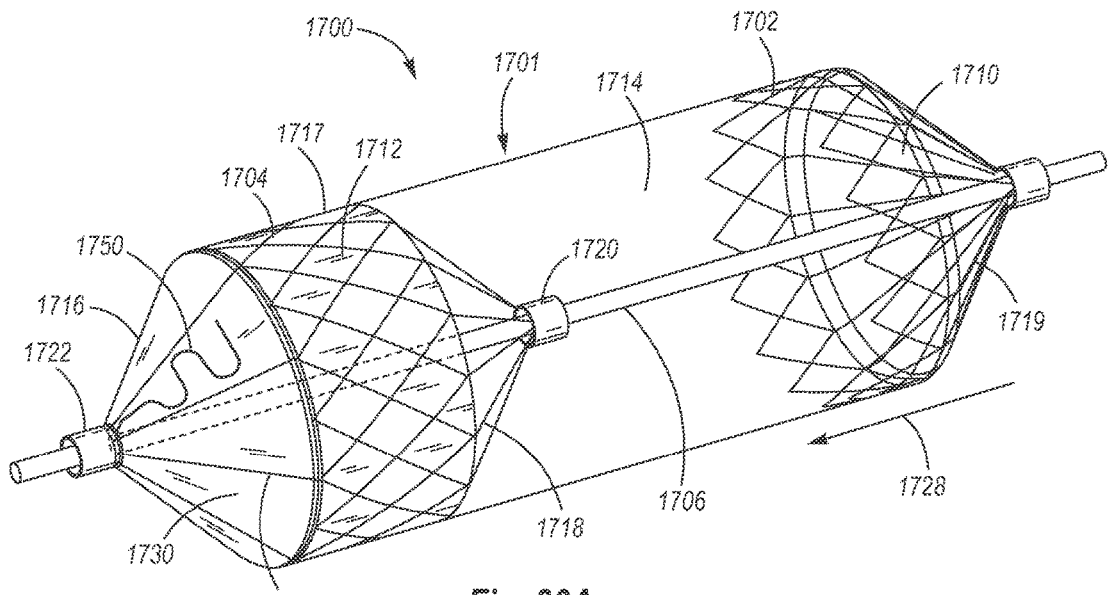
FIG. 30A is a perspective view of another embodiment of an aortic occlusion device.
Figure 30B:
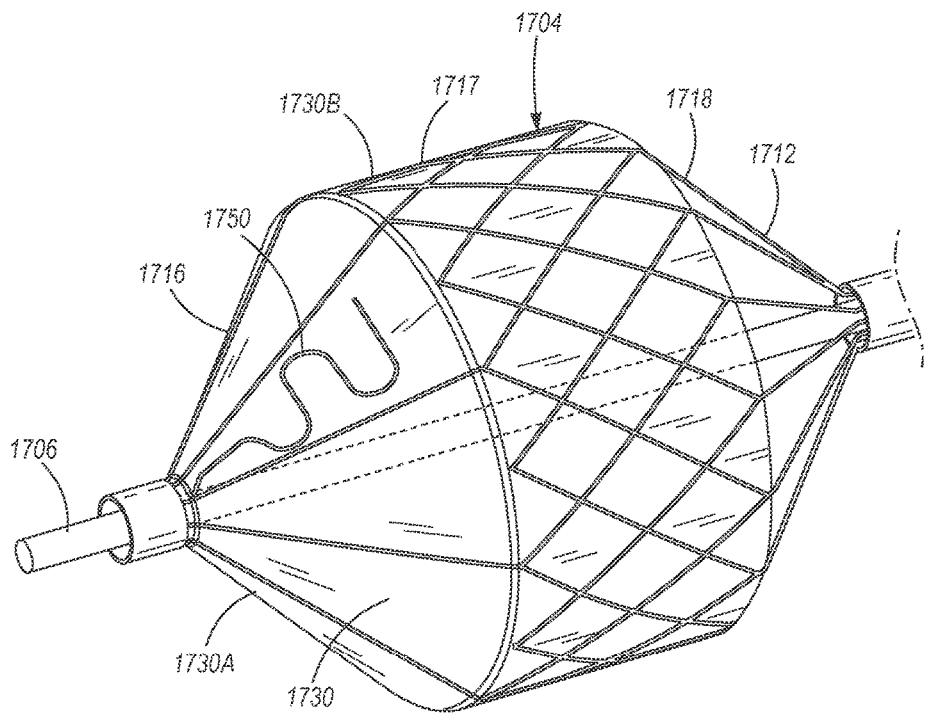
FIG. 30B is a partial perspective view of the embodiment of FIG. 30A.

Referring now to FIGS. 30A-30B, there is shown another embodiment of an aortic occlusion device 1700 comprising a generally tubular body 1701 having a proximal end portion 1702, a distal end portion 1704, and a porous covering 1714 extending therebetween. The proximal and distal end portions 1702, 1704 can comprise radially expandable frames or stents 1710, 1712, respectively, formed from a plurality of angled struts 1719. In some embodiments, the frame 1712 can comprise a first conical portion 1716 and a second conical portion 1718, the conical portions 1716, 1718 being separated by a cylindrical portion 1717. The struts 1719 of the conical portions 1716, 1718 can be retained in respective collars 1722, 1720, which can be slidably disposed around a catheter 1706. The catheter 1706 can extend through the distal end portion 1704, through the proximal end portion 1702, and out of the body through, for example, the femoral artery. In some embodiments, the catheter 1706 can project a distance distal from distal end portion 1704. However, in alternative embodiments, the catheter 1706 can terminate at any suitable distance adjacent the distal end portion 1704 of the device.

The distal end portion 1704 can comprise a liner 1730, which can have a substantially conical portion 1730A and a substantially cylindrical portion 1730B, as shown in FIG. 30B. The liner 1730 can prevent retrograde blood flow, indicated by arrow 1728, from flowing out of the distal end portion 1704 of the device. In some embodiments, the conical portion 1730A of the liner 1730 can comprise a string or wire 1750 incorporated into the liner 1730. When pulled by a user, the wire 1750 can tear or otherwise create an opening in the liner 1730. In this manner, when cardiac flow is reversed, the opening in liner 1730 created by the wire 1750 can allow blood to flow through the device in the antegrade direction. Pulling of the wire 1750 can be accomplished with a tether or pull wire that has a distal end connected to the wire 1750. The wire or tether can extend through or alongside catheter 1706 to a location outside the body where it can be accessed by a user. In alternative embodiments, the wire 1750 can be incorporated into the porous covering 1714, such that pulling the wire 1750 causes the wire to create an opening in the porous covering 1714, such as by tearing the porous covering 1714.

Figure 31A:
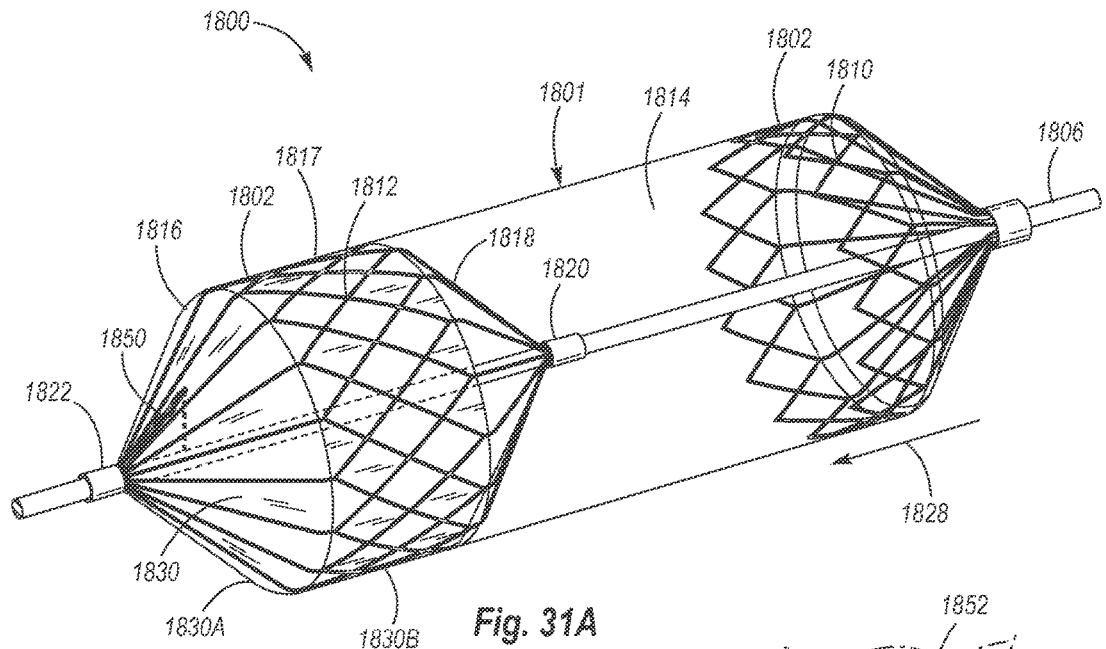
FIG. 31A is a perspective view of another embodiment of an aortic occlusion device.
Figure 31B:
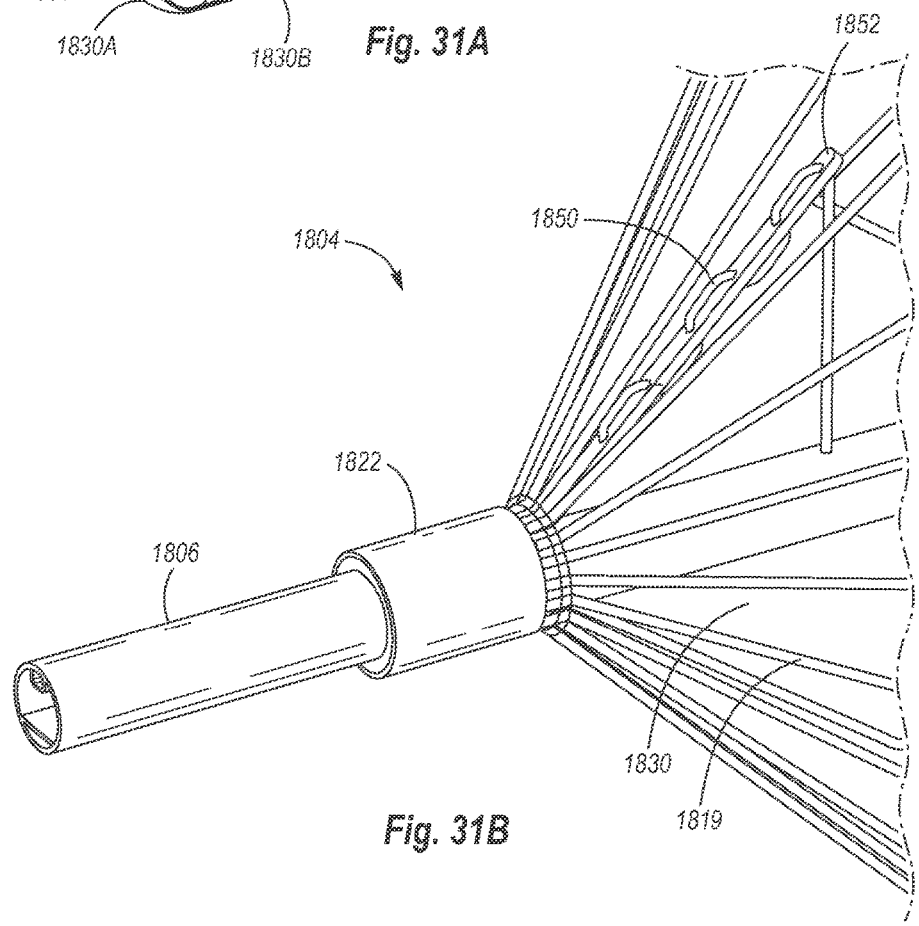
FIG. 31B is a partial perspective view of the embodiment of FIG. 31A.

Referring now to FIGS. 31A-31B, there is shown another embodiment of an aortic occlusion device 1800 comprising a generally tubular body 1801 having a proximal end portion 1802, a distal end portion 1804, and a porous covering 1814 extending therebetween. The proximal and distal end portions 1802, 1804 can comprise radially expandable frames or stents 1810, 1812, respectively, formed from a plurality of angled struts 1819. In some embodiments, the frame 1812 can comprise a first conical portion 1816 and a second conical portion 1818, the conical portions 1816, 1818 being separated by a cylindrical portion 1817. The struts 819 of the conical portions 1816, 1818 can be retained in respective collars 1822, 1820, which can be slidably disposed around a catheter 1806. The catheter 1806 can extend through the distal end portion 1804, through the proximal end portion 1802, and out of the body through, for example, the femoral artery.

The distal end portion 1804 can comprise a liner 1830, which can have a substantially conical portion 1830A and a substantially cylindrical portion 1830B, as shown in FIG. 31A. The liner 1830 can prevent retrograde blood flow, indicated by arrow 1828, from flowing out of the distal end portion 1804 of the device. In some embodiments, the conical portion 1830A of the liner 1830 can comprise a string or wire 1850 incorporated into the liner 1830. The wire 1850 can be stitched through, and retained by, a strut 1852 extending substantially proximally from the collar 1822. In some embodiments, the strut 1852 can comprise part of the frame 1812, and can terminate a distance distal of the cylindrical portion 1817 of the frame 1812. The wire 1850 can extend downwardly from the strut 1852 and into the catheter 1806, where it can be pulled or actuated from outside the body, as shown in FIG. 31B. When actuated by a user, the wire 1850 can tear or otherwise create an opening in the liner 1830, in a manner similar to the embodiment of FIGS. 30A-30B above. In this manner, when cardiac flow is reversed, the opening in liner 1830 created by the wire 1850 can allow blood to flow through the device in the antegrade direction. The distal end portion 1802 of the device 1800 is shown without the liner 1830 in FIG. 31B for purposes of illustration.

Figure 32:
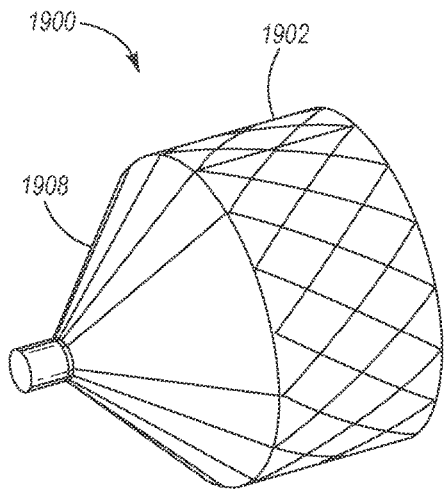
FIG. 32 is a perspective view of an alternative embodiment of a liner.
Figure 33A:
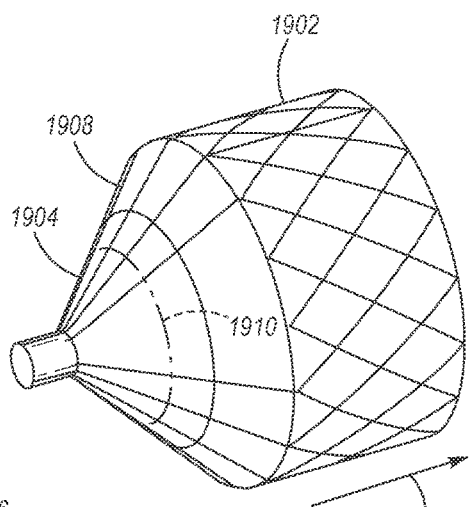
FIG. 33A is a perspective view of the liner of FIG. 32 having a sealing member in the closed position.
Figure 33B:
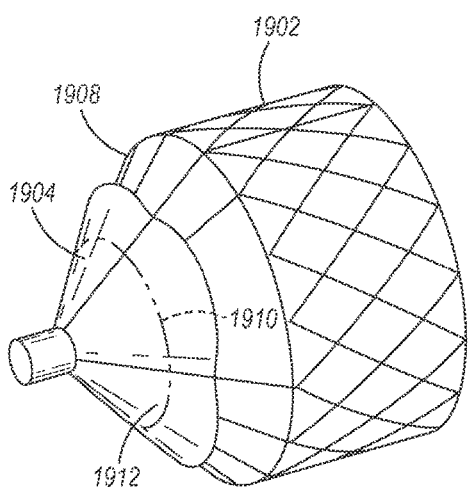
FIG. 33B is a perspective view of the liner of FIG. 33A illustrating the sealing member in an open position.
Figure 33C:
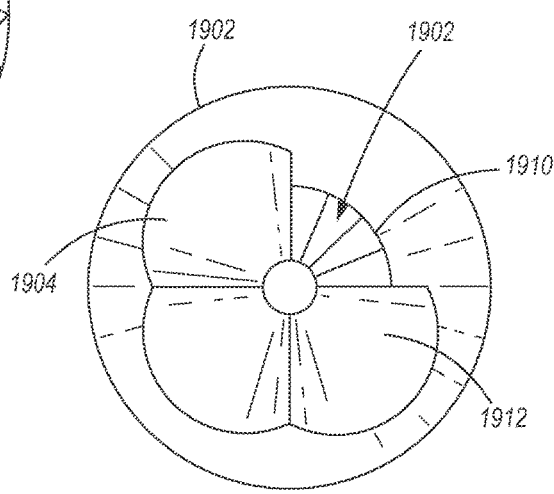
FIG. 33C is a front view of the liner of FIG. 33A.
Figure 33D:
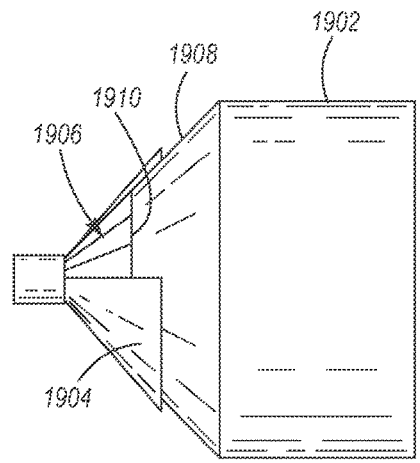
FIG. 33D is a side elevation view of the liner of FIG. 33A.

Referring now to FIGS. 32, and 33A-33D, there is shown another embodiment of a liner 1900 having a substantially cylindrical portion 1902 and a substantially conical portion 1908. As shown in FIG. 32, the liner 1900 can be configured to prevent blood flow through an aortic occlusion device and allow antegrade blood flow by other means, such as by being radially collapsed when cardiac flow is reversed. In alternative embodiments, the liner 1900 can be combined with a sealing member 1904, as shown in FIG. 33A. The conical portion 1908 can comprise a distal edge 1910 that can terminate a distance proximal to the distal end of the conical portion 1908 so as to define an opening 1906, as shown in FIGS. 33C and 33D with the sealing member 1904 partially cut away. In some embodiments, the sealing member 1904 can be overlaid on the conical portion 1908 and can be attached (e.g., by stitching, adhesive, etc.) to the conical portion 1908 at intervals so as to define leaflets or flaps 1912, as shown in FIGS. 33B-33C. In this manner, blood flow in the direction indicated by arrow 1914, such as retrograde blood flow, can cause the leaflets 1912 of the sealing member 1904 to lie flush against the liner 1902, thereby preventing blood flow through the opening 1906, as shown in FIG. 33A. However, blood flow in the direction indicated by arrow 1916, such as antegrade blood flow, can cause the leaflets 1912 to billow or lift away from the liner 1902, thereby allowing blood to flow through the opening 1906, as shown in FIGS. 33B-33C.

Figure 34A:
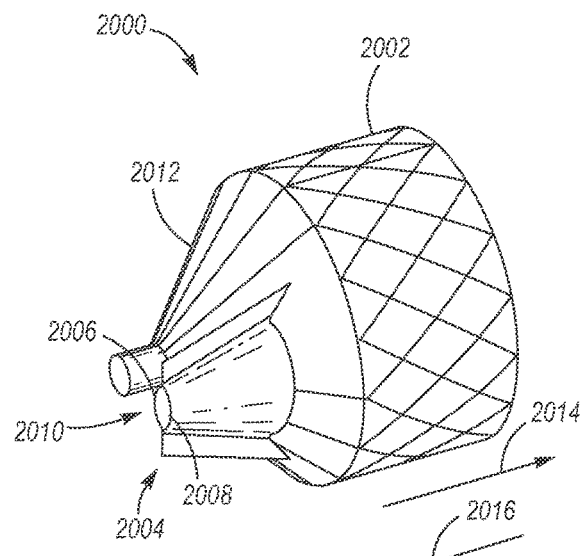
FIG. 34A is a perspective view of another embodiment of a liner.
Figure 34B:
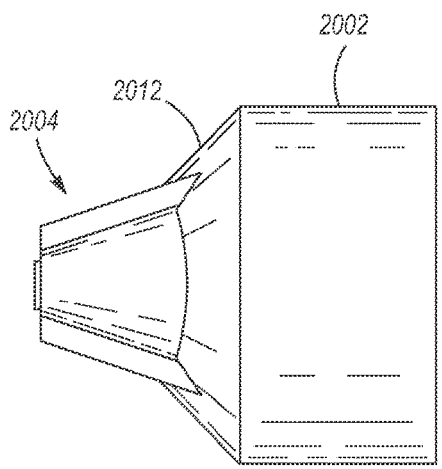
FIG. 34B is a side elevation view of the liner of FIG. 34A.
Figure 34C:
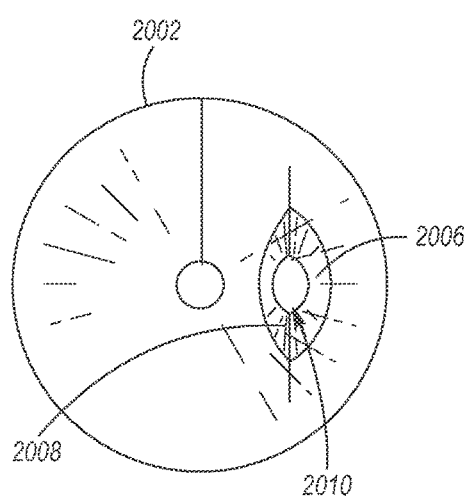
FIG. 34C is a front view of the liner of FIG. 34A.

Referring now to FIGS. 34A-34C, there is shown another embodiment of a liner 2000 having a substantially cylindrical portion 2002 and a substantially conical portion 2012. In some embodiments, the liner 2000 can be combined with a sealing member 2004. The sealing member 2004 can comprise a first portion 2006 and a second portion 2008 that are sealed together to form a tapered flapper valve, and can be positioned over an opening 2010 defined in the conical portion 2012 of the liner 2000. The sealing member 2004 can be configured such that blood flow in the direction indicated by arrow 2014, such as retrograde blood flow, causes the first and second portions 2006, 2008 of the sealing member 2004 to move together or close, thereby preventing blood flow through the opening 2010 of the liner 2000. However, the sealing member 2004 can be configured such that blood flow in the direction indicated by arrow 2016, such as antegrade blood flow, can cause the first and second portions 2006, 2008 of the sealing member 2004 to move apart, as shown in FIG. 34C, thereby allowing blood to flow through the opening 2010 of the liner 2000.

Figure 35A:
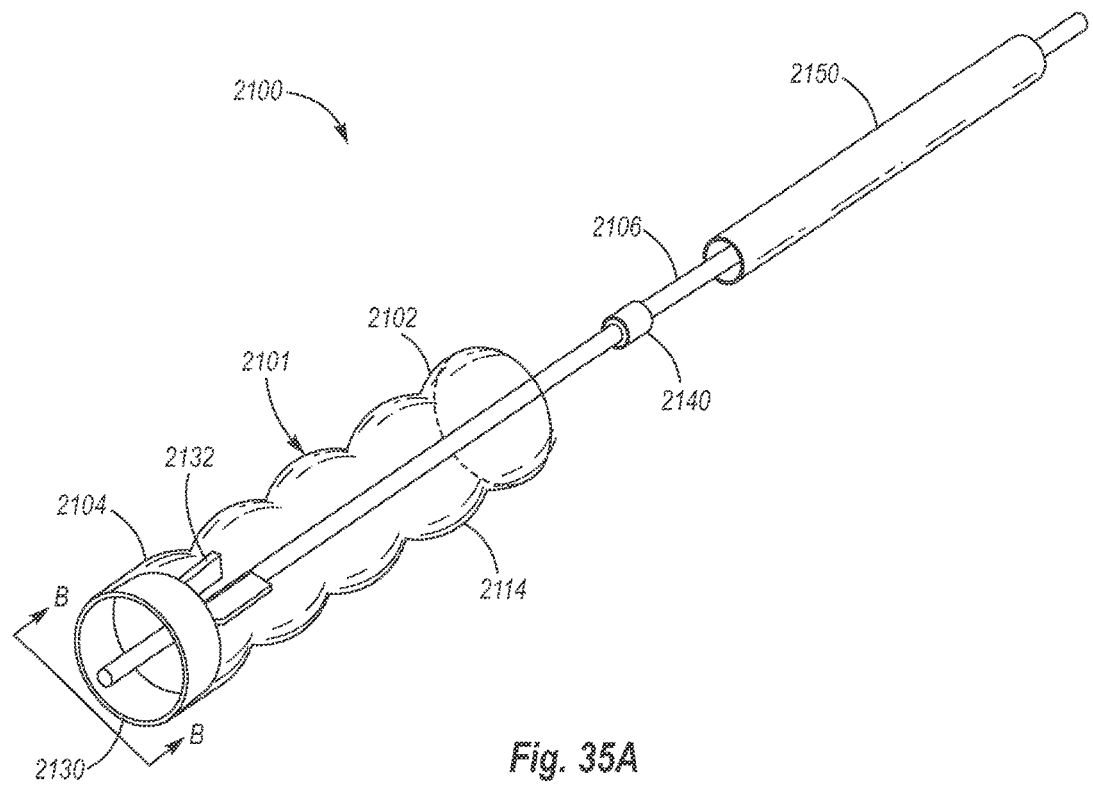
FIG. 35A is a perspective view of another embodiment of an aortic occlusion device.
Figure 35B:
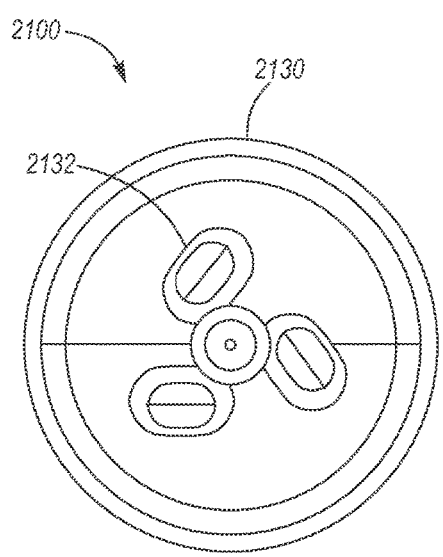
FIG. 35B is an end view of the embodiment of FIG. 35A taken along the line A-A of FIG. 35A.
Figure 35C:
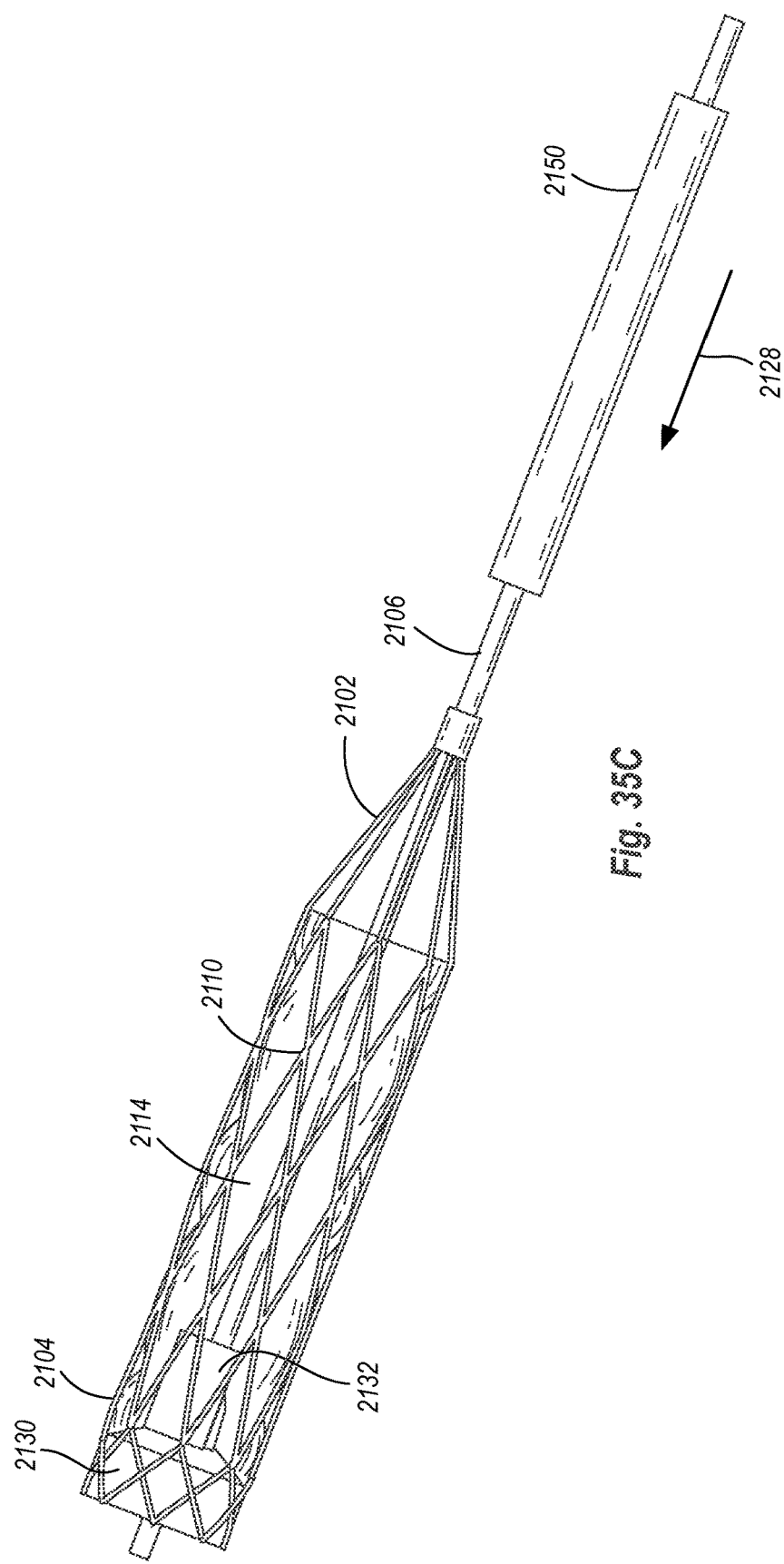

Referring now to FIGS. 35A-35C, there is shown another embodiment of an aortic occlusion device 2100 comprising a generally tubular body 2101 having a proximal end portion 2102, a distal end portion 2104, and a porous covering 2114 extending therebetween. The device 2100 can include a catheter 2106, which can extend through the distal end portion 2104 of the tubular body 2101, through the proximal end portion 2102, and out of the body through, for example, the femoral artery. The device can include a ferrule 2140 disposed around the catheter 2106, and a sheath 2150 disposed around the catheter 2106 and located proximally with respect to the tubular body 2101. In some embodiments, the tubular body 2101 can be configured to radially collapse such that it can be loaded into the sheath 2150 for insertion and removal from a patient's body.

The tubular body 2101 can include a liner 2130 located in the distal end portion 2104. The liner 2130 can include one or more valves, such as duckbill valves 2132 extending proximally from the liner 2130 and within the porous covering 2114. The duckbill valves 2132 can be configured to prevent retrograde blood flow, indicated by arrow 2128 (FIG. 35C), from passing through the distal end portion 2104. When cardiac flow is reversed, the relatively higher blood pressure exerted on the liner 2130 from the heart can cause the duckbill valves 2132 to open, thereby allowing antegrade blood flow through the valves 2132. FIG. 35B illustrates an end view through the device 2100 along the line B-B of FIG. 35A.

In alternative embodiments, the device 2100 can comprise a single frame 2110, as shown in FIG. 35C. The frame 2110 can be fabricated from a plurality of angled struts 2119, and can extend from the distal end portion 2104, and along the porous covering 2114. In some embodiments, the frame 2110 can comprise a tapered proximal end 2102 that allows the frame 2110, the sealing member 2130, and the porous covering 2114 to be retracted and recollapsed into the sheath 2150 after use.

Figure 36A:
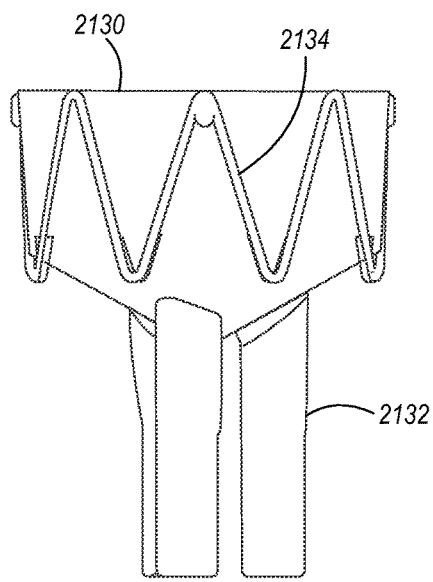
FIGS. 36A-36B are side elevation views of the liner of the embodiment of FIG. 35A.
Figure 36B:
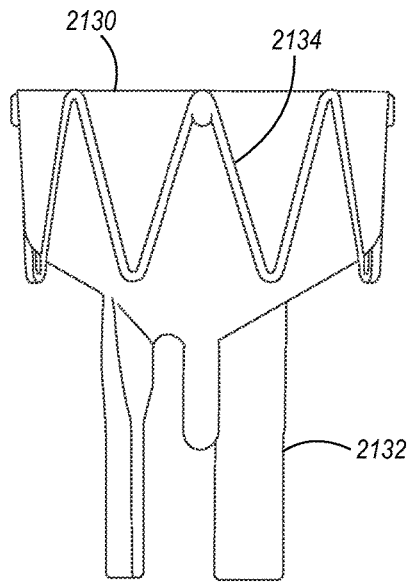
Figure 36C:
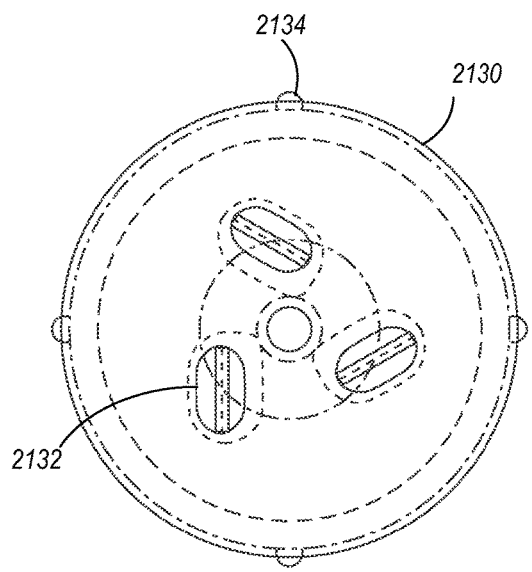
FIG. 36C is an end view of the liner of FIG. 36A.
Figure 36D:
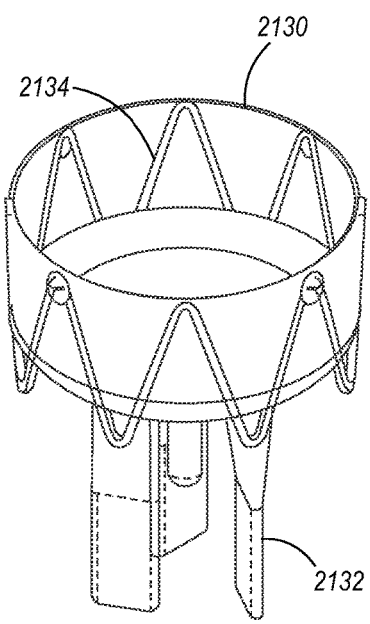
FIG. 36D is a perspective view of the liner of FIG. 36A.

In some embodiments, the liner 2130 can comprise three valves 2132, as shown in FIGS. 35B and 36A-36D. Alternatively, the liner 2130 can comprise two valves 2132, as shown in FIG. 36B. In further alternative embodiments, the liner 2130 may comprise any suitable number of valves. The valves 2132 can be integrally fabricated with the liner 2130, such as by dip coating, or can be attached to the liner after fabrication. In some embodiments, the liner 2132 can comprise a frame 2134. The frame 2134 can have a substantially sinusoidal shape and can extend around a circumference of the liner, as shown in FIGS. 36A, 36B, and 36D. In some embodiments, the liner 2130 can be fabricated from a polymeric material, such as a vinyl chloride monomer (e.g., Plastisol®).

Figure 37A:
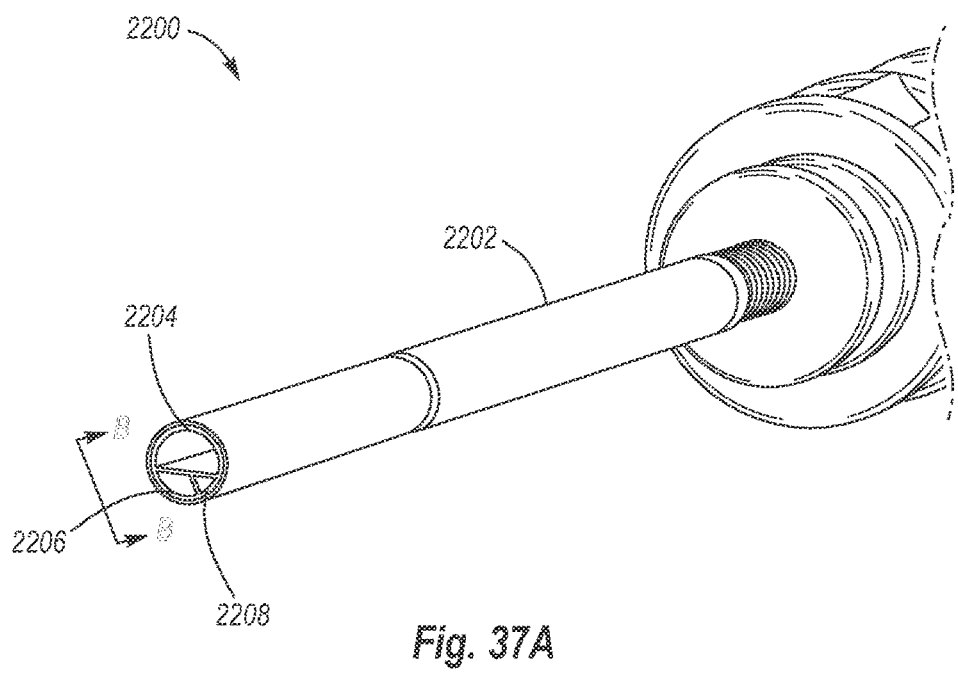
FIG. 37A is a perspective view of another of a delivery catheter.
Figure 37B:
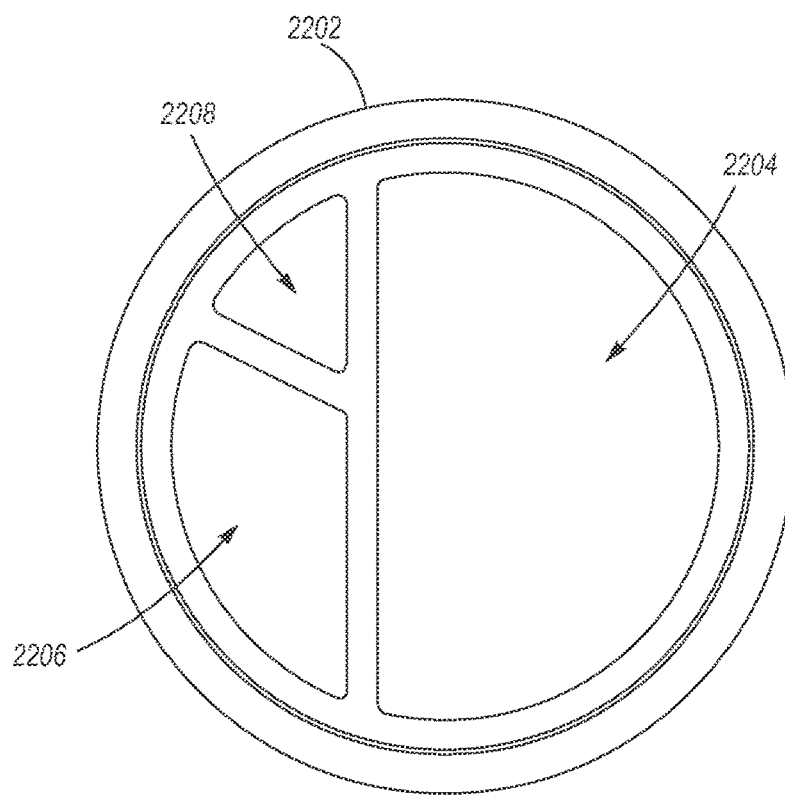
FIG. 37b is a cross-sectional view of the catheter of FIG. 37A.

Referring now to FIGS. 37A-37B, there is shown an embodiment of a catheter 2200 for an aortic occlusion device. The catheter 2200 can comprise a tubular member 2202 defining a first lumen 2204, a second lumen 2206, and a third lumen 2208. In some embodiments, the first lumen 2204 can comprise 50% or greater of the cross-sectional area of the catheter 2200, as shown in FIG. 38B. The lumens 2204, 2206, 2208 can be useful for, for example, delivery and removal of instruments, introducing cardioplegic fluid into the heart, conducting blood or other materials out of the body, conducting signals indicative of fluid pressure, temperature, or other parameters, conducting balloon inflation fluid, and/or other uses.

Figure 38A:
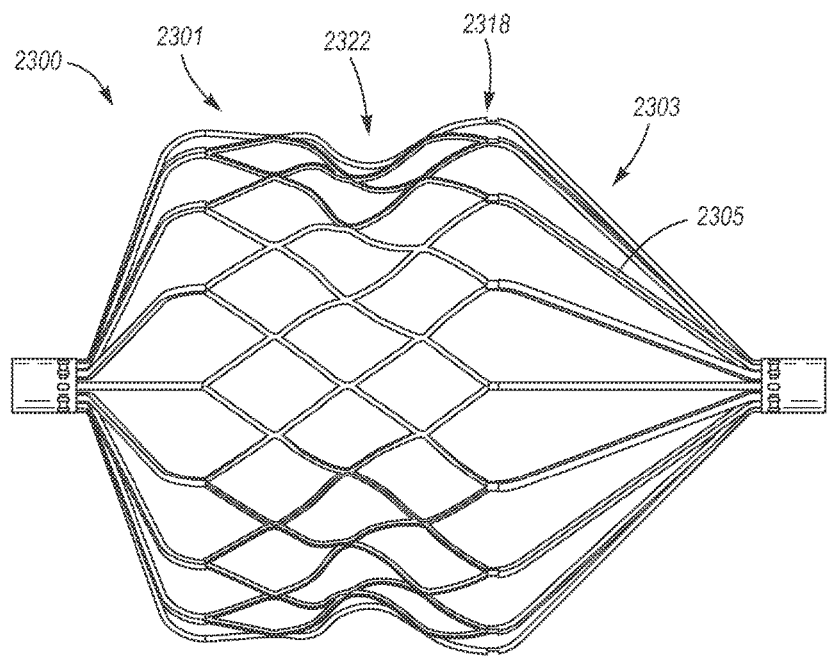
FIG. 38A is a side elevation view of another embodiment of a frame.
Figure 38B:
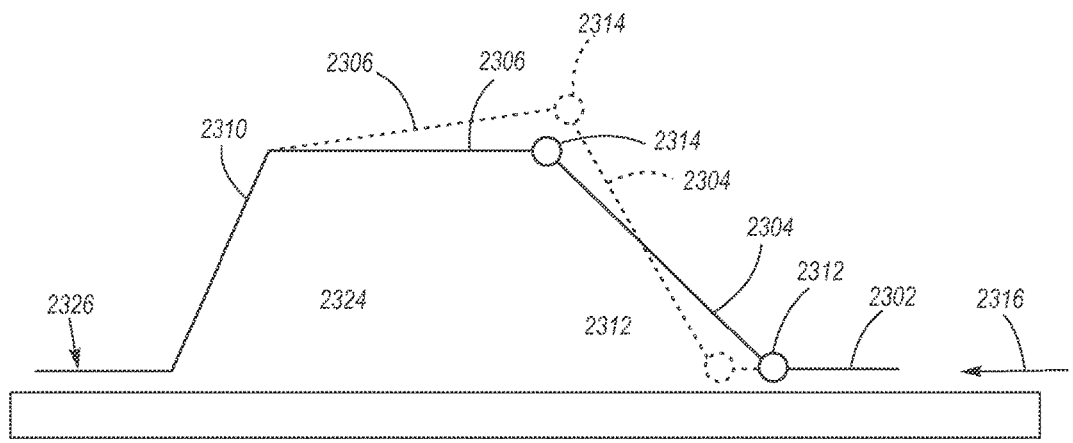
FIG. 38B is a schematic illustration of radial expansion of the frame of FIG. 38A.

Referring now to FIGS. 38A-38G, there is shown another embodiment of a frame 2300 formed from a plurality of angled struts 2305 for use in an aortic occlusion device. The frame 2300 can comprise a first portion 2301 and a second portion 2303, the first and second portions having a first diameter, and being interconnected by an intermediate portion 2322 having a second diameter. As shown in FIG. 38A, the diameter of the intermediate portion 2322 can be smaller than the diameter of the first and second portions 2301, 2303. In this manner, the intermediate portion 2322 can allow the frame 2300 to be movable between a radially expanded state and a radially collapsed state, as further explained below.

In some embodiments, the frame 2300 can be configured to operate as a collection of linkages when an axial force is applied. As shown in FIG. 38B, a representative linkage of the frame 2300 can comprise a first rigid member 2302 interconnected with a second rigid member 2304 by a first pinned joint 2312. The second rigid member 2304 can be interconnected with a third rigid member 2306 by a second pinned joint 2314, and the third rigid member 2306 can be interconnected with a fourth rigid member 2310. In this manner, when the linkage of the frame 2300 is affixed to a catheter 2324 at a point indicated at 2326, and a force is applied to the linkage in the direction indicated by arrow 2316, certain portions of the frame 2300 can act as a rigid linkage with pinned joints that rotate without taking moments. In this manner, rigid members 2304 and 2306 can be moved into the respective positions shown in phantom in FIG. 38B, and the frame 2300 can be radially collapsed into a substantially cylindrical shape, as shown in FIG. 38C.

Figure 38C:
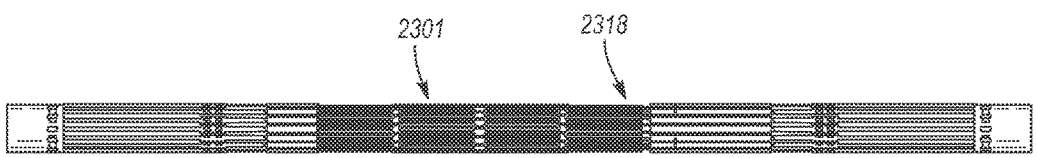
FIG. 38C is a side elevation view of the frame of 38A in a radially collapsed state.
Figure 38D:
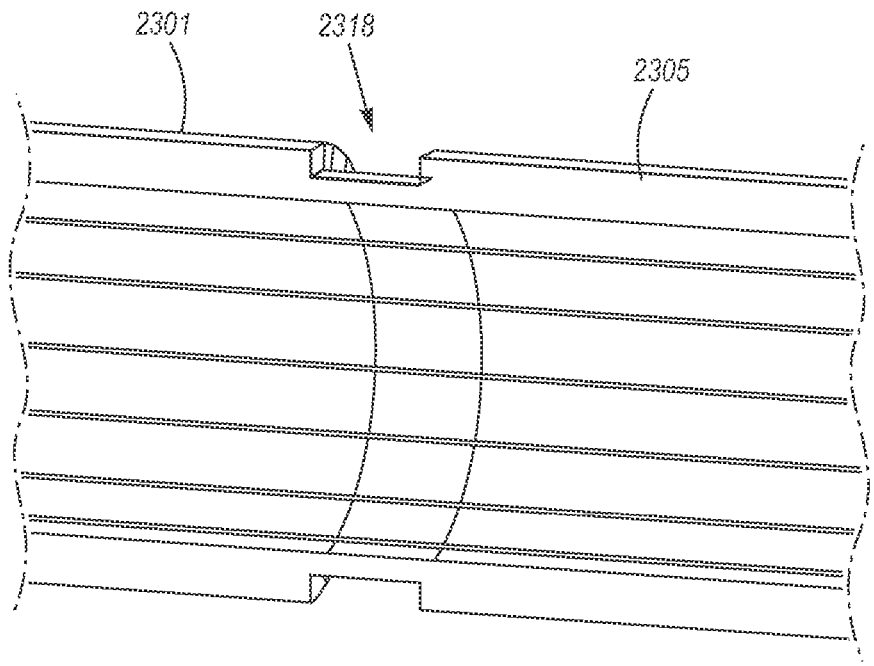
FIG. 38D is an enlarged view of a groove of the frame of FIG. 38A in a radially collapsed state.
Figure 38E:
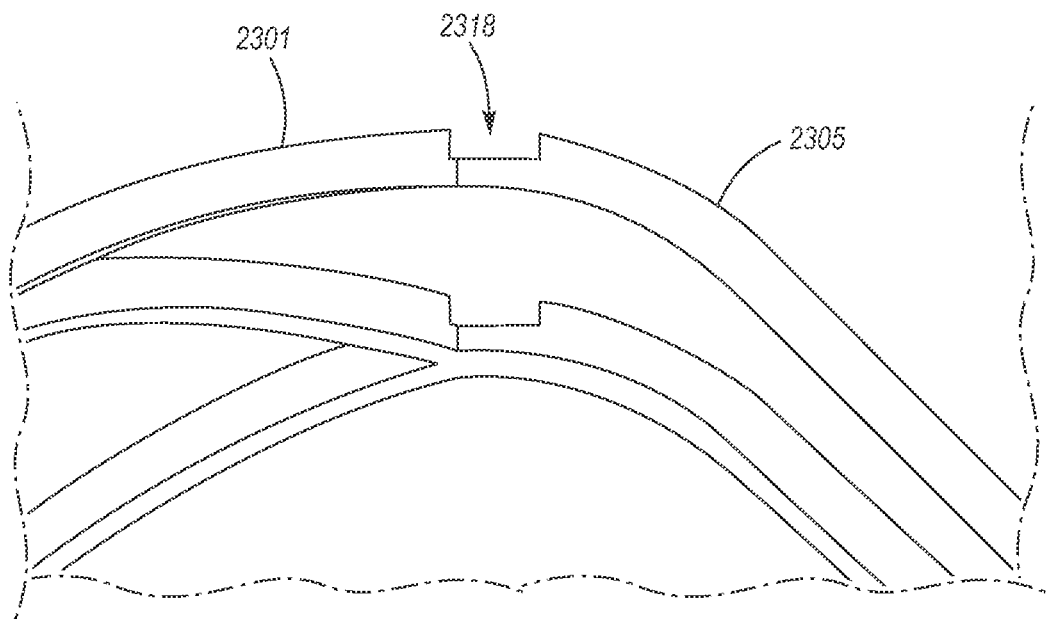
FIG. 38E is an enlarged view of the groove of the frame of FIG. 38D in a radially expanded state.

In some embodiments, pinned joints, such as the pinned joints 2312 and 2314 of FIG. 38B, can be created by, for example, machining a groove 2318 into the individual struts 2305 of the frame 2300, as shown in FIGS. 38A, 38C, and 38D. In this manner, the application of force in the direction indicated by arrow 2316 of FIG. 38B can induce rotation of the members about groove 2318 by plastically deforming the material.

Figure 38F:
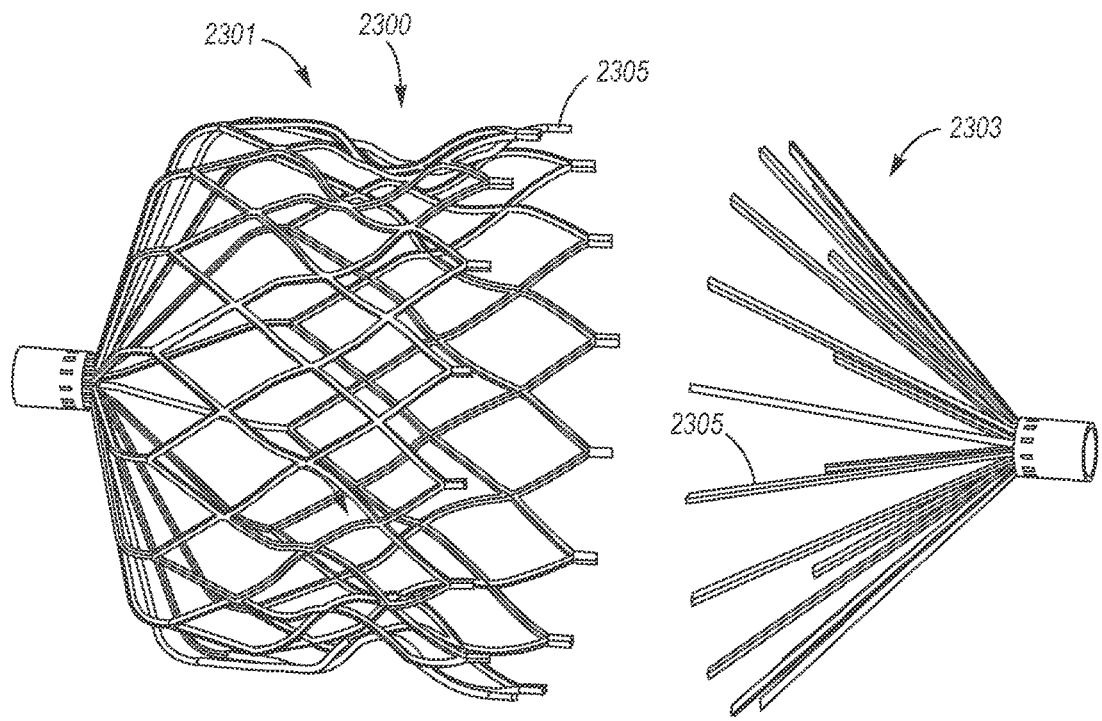
FIG. 38F is a side elevation view of an alternative embodiment of the frame of FIG. 38A.

In some embodiments, the second portion 2303 of the frame 2300 can be affixed to the first portion 2301 by, for example, laser welding. In some embodiments, the elongated struts 2305 of the second portion 2303 can be thicker than the struts of the first portion 2301, as shown in FIG. 38F, owing to the fact that additional components of the aortic occlusion device, such as the liner and/or porous covering, need only fit under the first portion 2301 of the frame 2300 when in a collapsed state and not under the second portion 2303.

Figure 39:
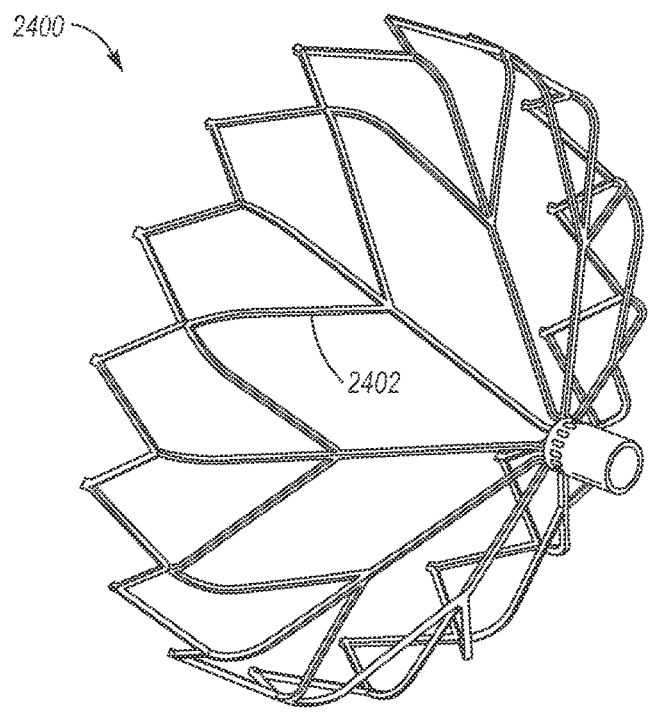
FIG. 39 is a perspective view of another embodiment of a frame of FIG. 38A.

Referring now to FIG. 39, there is shown another embodiment of a frame 2400 for use in an aortic occlusion device. The frame can comprise a plurality of struts 2402 arranged in a webbing arrangement. When combined with, for example, the first portion 2301 of the frame of FIG. 38A, the webbing arrangement can reduce the axial length of the struts 2402, which can improve transmission of axial force applied in the manner of FIG. 38B. This can result in less deflection of the struts 2402 and better transmission of axial force to radial force when expanding the frame 2400 from a collapsed state.

Figure 40C:
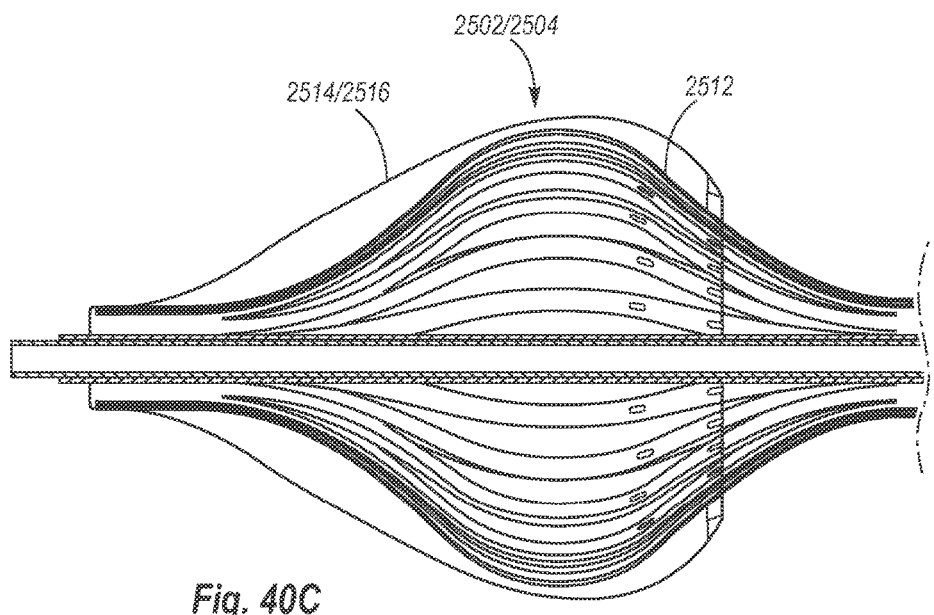
FIG. 40C is a side elevation view of a representative embodiment of an enclosure of the device of FIG. 40A in an open position.
Figure 40D:
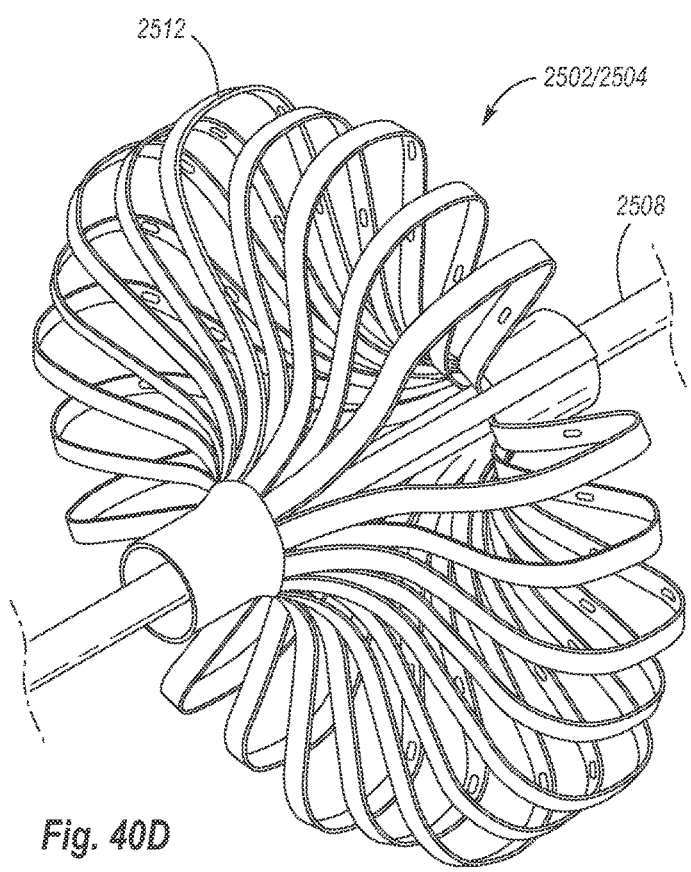
FIG. 40D is a perspective view of a representative embodiment of an enclosure of the device of FIG. 40A in an open position.
Figure 40E:
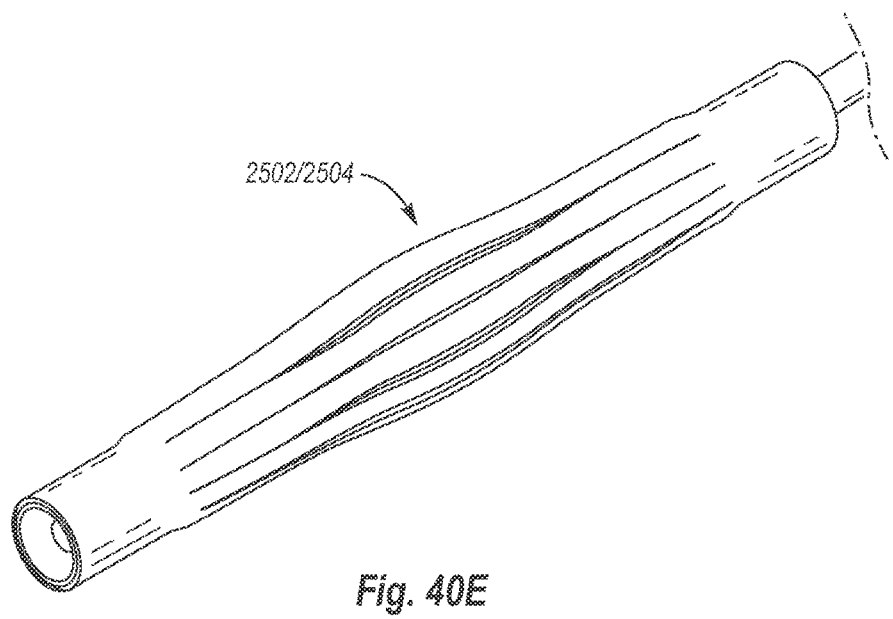
FIG. 40E is a perspective view of a representative embodiment of an enclosure of the device of FIG. 40A in a closed position.
Figure 40F:
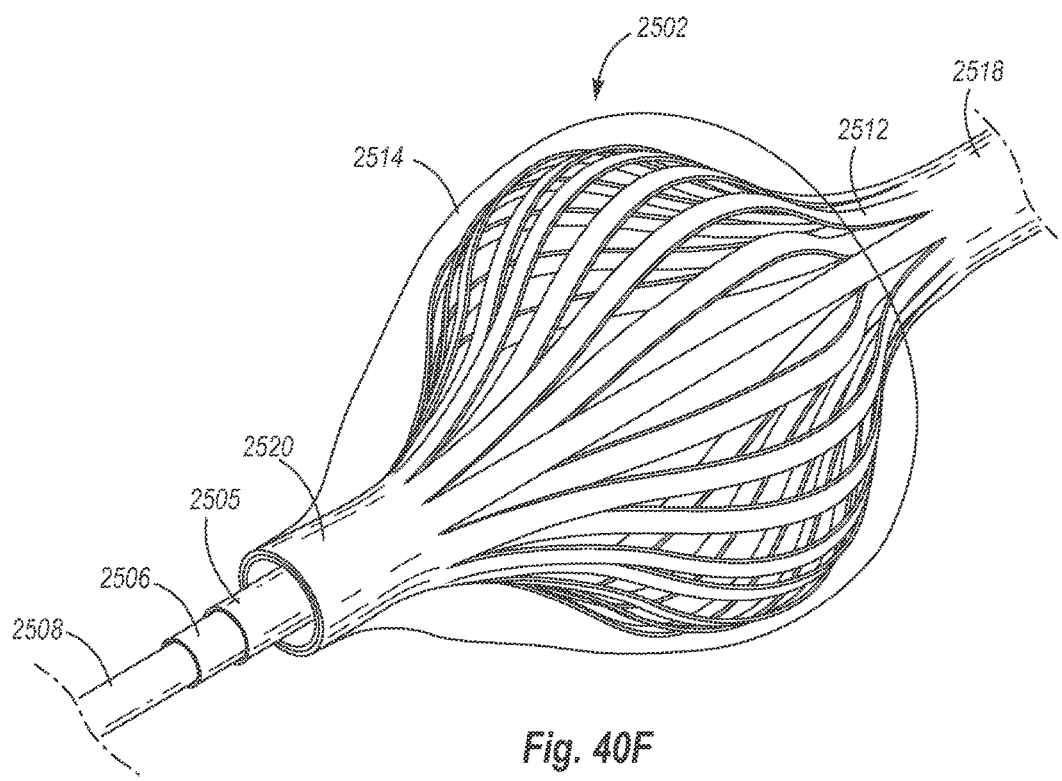
FIG. 40F is a perspective view of a first enclosure of the embodiment of FIG. 40A.
Figure 40G:
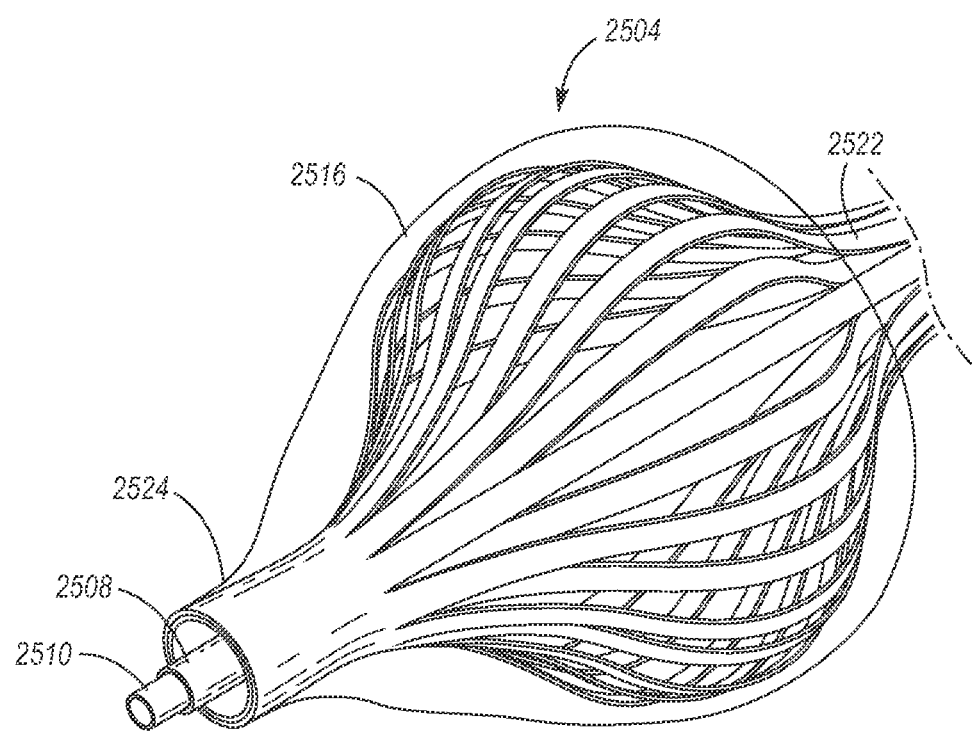

Referring now to FIGS. 40A-40G, there is shown another embodiment of an aortic occlusion device 2500. The aortic occlusion device 2500 can comprise a first expandable enclosure 2502 and a second expandable enclosure 2504 disposed around a plurality of coaxial catheters 2505, 2506, 2508, and 2510. The first and second enclosures 2502, 2504 can comprise a plurality of radially disposed elongated members 2512 movable between a collapsed position (FIG. 40E) and an expanded position (FIGS. 40F and 40G). The elongated members 2512 of the first enclosure 2502 can extend between first and second collars 2518 and 2520, as shown in FIG. 40B. In this manner, the movement of the collars 2518, 2520 toward one another can cause the elongated members 2512 to bow and expand radially outward when in the open position, as shown in FIG. 40G. Similarly, the elongated members 2512 of the second enclosure 2504 can be disposed between first and second collars 2522 and 2524, such that when the collars 2522, 2524 are moved toward one another in the open position, the elongated members bow radially outward, as shown in FIG. 40F.

Figure 41A:
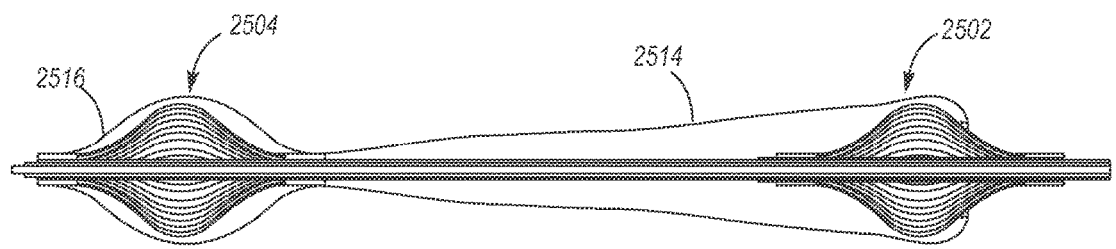
FIGS. 41A-41B are side elevation views of an alternative embodiment of the aortic occlusion device of FIG. 40A.
Figure 41B:
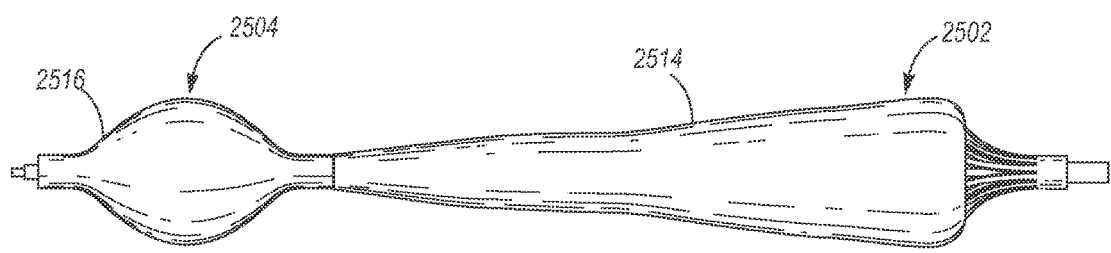

The first enclosure 2502 can be covered with a porous covering 2514 similar to the porous covering of the embodiment of FIGS. 8A-8D. In this manner, the first enclosure 2502 can remove emboli from retrograde blood flow in the direction of arrow 2528 during cardiopulmonary bypass (see FIG. 40B). In some embodiments, the porous covering 2514 can extend from the second collar 2520 of the first enclosure 2502 to a distance distal of the first collar 2518, as shown in FIGS. 40B and 40F. In alternative embodiments, the covering 2514 can extend substantially from the second collar 2520 to the first collar 2518 of the first enclosure 2502. In some embodiments, the porous covering 2514 can extend substantially from the first enclosure 2502 to the first collar 2522 of the second enclosure 2504, as shown in FIGS. 41A-41B.

Similarly, the second enclosure 2504 can be covered with a substantially non-porous covering 2516, so as to prevent retrograde blood flow past the second enclosure 2504 when the second enclosure 2504 is in the open position. In some embodiments, the covering 2516 can extend from the second collar 2524 of the second enclosure 2504 to a distance distal of the first collar 2522, as shown in FIGS. 40B and 40G. In alternative embodiments, the covering 2516 can extend substantially from the second collar 2524 to the first collar 2522 of the second enclosure 2504.

The first and second enclosures 2502, 2504 can be actuated between their respective open and closed positions by the catheters 2505, 2506, 2508, and 2510. In an exemplary embodiment shown in FIG. 40B, the first collar 2518 of the first enclosure 2502 is secured to the outermost catheter 2505 while the second collar 2520 is secured to the catheter 2506, which can be disposed coaxially through the lumen of the catheter 2505. In this manner, longitudinal movement of the catheters 2505, 2506 with respect to one another can cause the first enclosure 2502 to be actuated between the open position and the closed position. Similarly, the first collar 2522 of the second enclosure 2504 can be secured to the catheter 2508 while the second collar 2524 can be secured to the catheter 2510. The catheter 2508 can be disposed coaxially through the lumen of the catheter 2506, and the catheter 2510 can be disposed coaxially through the lumen of the catheter 2508. In this manner, longitudinal movement of the catheters 2508, 2510 with respect to one another can cause the second enclosure 2504 to be actuated between the open position and the closed position independently of the first enclosure 2502. In some embodiments, the first and second enclosures 2503, 2504 can be configured such that actuation of the catheters 2505, 2506, 2508, 2510 can expand the enclosures to a diameter about equal to, and/or substantially greater than, the natural inner diameter of the aorta in order to hold the device in place within the aorta, as shown in FIG. 40D.

Figure 42A:
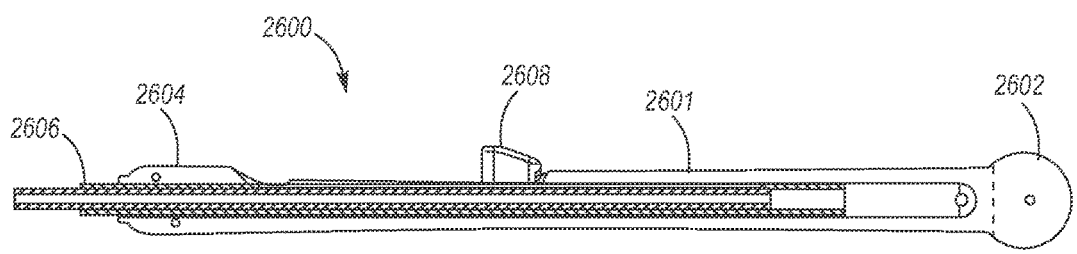
FIGS. 42A-42B are side elevation views of an exemplary embodiment of a catheter actuator.
Figure 42B:
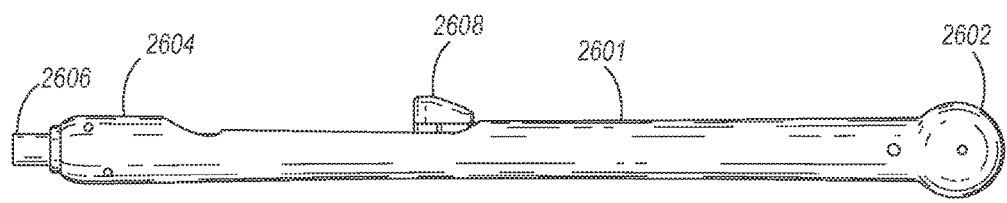
Figure 43A:
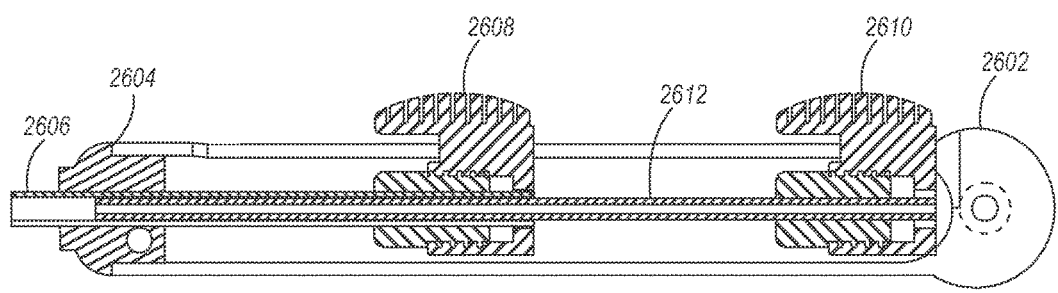
FIGS. 43A-43B are side elevation views of an alternative embodiment of the catheter actuator of FIG. 42A.
Figure 43B:
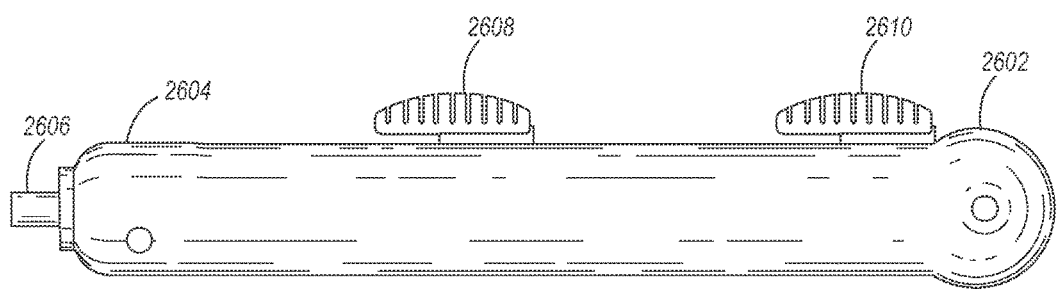

Referring now to FIGS. 42A-42B, there is shown an exemplary embodiment of a catheter actuator 2600. The catheter actuator 2600 can comprise a generally tubular housing 2601 having a proximal end portion 2602 and a distal end portion 2604. The actuator 2600 can include a slider 2608 movable between a first position and a second position. The slider 2608 can be coupled to a catheter 2606 disposed through the housing 2601 of the actuator such that movement of the slider 2608 between the first and second positions causes longitudinal movement of the catheter 2606 relative to the distal end portion 2604. In this manner, catheters, such as the catheters 2505-2510 of the embodiment of FIGS. 40A-40G, can be actuated by a user from outside the patient's body. In alternative embodiments, the actuator 2600 can include a second slider 2610 coupled to a second catheter 2612, as shown in FIGS. 43A-43B. The second catheter 2612 can be coaxially disposed through the lumen of the first catheter 2606 such that movement of the second slider 2610 causes the second catheter 2612 to travel axially with respect to the first catheter 2606. Alternative embodiments of the actuator 2600 can include any suitable number of sliders or equivalent mechanisms coupled to a respective number of catheters to effect movement of the catheters.

Unless described otherwise, the various components of the systems and devices of the present disclosure can be formed of conventional materials using conventional manufacturing techniques. The dimensions of the various components are selected so that they perform their intended functions in their intended environment, but are not intended to limit the scope of the present disclosure unless expressly claimed.

For purposes of this description, certain aspects, advantages, and novel features of the embodiments of this disclosure are described herein. The disclosed embodiments should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

What is claimed is:

1. An aortic occlusion device, comprising:
a radially expandable and collapsible proximal end portion and a radially expandable and collapsible distal end portion, wherein the distal end portion comprises a substantially conical portion, and the proximal and distal end portions are configured to radially expand within an aorta to secure the device within the aorta;
a catheter extending axially between the distal end portion and the proximal end portion;
a porous covering positioned around the catheter and between the proximal end portion and the distal end portion; and
a one-way valve positioned between the substantially conical portion of the distal end portion and the proximal end portion of the device and configured to restrict retrograde blood flow through the device toward the heart.

2. The aortic occlusion device of claim 1, wherein the device is configured to be positioned in the aortic arch.

3. The aortic occlusion device of claim 2, wherein the distal end portion is configured to be positioned in the ascending aorta.

4. The aortic occlusion device of claim 2, wherein the proximal end portion is configured to be positioned in the descending aorta.

5. The aortic occlusion device of claim 1, wherein the device is radially self-expandable from a collapsed configuration to an expanded configuration within the aorta.

6. The aortic occlusion device of claim 1, wherein the proximal end portion and the distal end portion each comprise discrete radially expandable frames.

7. The aortic occlusion device of claim 6, wherein the radially expandable frames comprise self-expandable stents.

8. The aortic occlusion device of claim 6, wherein the radially expandable frames comprise balloon-expandable stents.

9. The aortic occlusion device of claim 1, wherein the device is configured to be inserted and removed from a patient's body percutaneously using a delivery catheter.

10. A system including
the aortic occlusion device of claim 1,
a cardiopulmonary bypass system configured to provide a flow of oxygenated blood to the aortic occlusion device in a retrograde flow direction, and
a source of cardioplegia fluid in fluid communication with the catheter.

11. An aortic occlusion device, comprising:
a radially expandable and collapsible proximal end portion and a radially expandable and collapsible distal end portion, the proximal and distal end portions configured to radially expand within an aorta to secure the device within the aorta, wherein the distal end portion comprises a substantially conical portion;

a catheter extending axially between the distal end portion and the proximal end portion;

a porous covering positioned around the catheter and between the proximal end portion and the distal end portion; and a valve between the conical portion of the distal end portion and the proximal end portion of the device, wherein the valve is configured to restrict retrograde blood flow through the device toward the heart, wherein the valve comprises a cylindrical valve housing with radial openings therein, and the valve further comprises a movable valve element configured to selectively cover and uncover the radial openings.

12. The aortic occlusion device of claim 11, wherein the movable valve element comprises a flexible sealing member movable between an open position wherein free portions of the flexible sealing member flare radially away from the cylindrical valve housing, and a closed position wherein the free portions of the flexible sealing member engages against the cylindrical valve housing.

13. The aortic occlusion device of claim 12, wherein the flexible sealing member comprises a plurality of leaflets having free ends configured to open radially away from the cylindrical valve housing and to close inwardly against the cylindrical valve housing.

14. The aortic occlusion device of claim 11, wherein the valve moves from an open configuration to a closed configuration responsive to fluid flow.

15. The aortic occlusion device of claim 11, wherein the distal end portion is configured to be positioned and expanded in the ascending aorta, and the proximal end portion is configured to be positioned and expanded in the descending aorta.

* * * * *